(12) United States Patent
Boveja et al.

(10) Patent No.: US 7,444,184 B2
(45) Date of Patent: Oct. 28, 2008

(54) METHOD AND SYSTEM FOR PROVIDING THERAPY FOR BULIMIA/EATING DISORDERS BY PROVIDING ELECTRICAL PULSES TO VAGUS NERVE(S)

(75) Inventors: Birinder R. Boveja, Milwaukee, WI (US); Angely Widhany, Milwaukee, WI (US)

(73) Assignee: Neuro and Cardial Technologies, LLC

( * ) Notice: Subject to any disclaimer, the term of this patent is extended or adjusted under 35 U.S.C. 154(b) by 239 days.

(21) Appl. No.: 11/120,125

(22) Filed: May 2, 2005

(65) Prior Publication Data

US 2005/0192644 A1 Sep. 1, 2005

Related U.S. Application Data

(63) Continuation of application No. 10/436,017, filed on May 11, 2003, now Pat. No. 7,191,012.

(51) Int. Cl.
*A61N 1/00* (2006.01)

(52) U.S. Cl. .............................. 607/40; 607/60; 607/61; 607/118

(58) Field of Classification Search .................. 607/40, 607/60, 61, 118, 33
See application file for complete search history.

(56) References Cited

U.S. PATENT DOCUMENTS

| | | | | |
|---|---|---|---|---|
| 3,796,221 A | | 3/1974 | Hagfors et al. ............... 128/421 |
| 4,014,346 A | * | 3/1977 | Brownlee et al. ............. 607/33 |
| 4,702,254 A | | 10/1987 | Zabara et al. ................ 128/421 |
| 4,867,164 A | | 9/1989 | Zabara et al. ................ 128/421 |
| 5,025,807 A | | 6/1991 | Zabara et al. ................ 128/421 |
| 5,188,104 A | * | 2/1993 | Wernicke et al. ............. 607/40 |
| 5,193,539 A | | 3/1993 | Schulman et al. ......... 128/419 R |
| 5,299,569 A | | 4/1994 | Wernicke et al. ............ 607/118 |
| 5,405,367 A | | 4/1995 | Schulman et al. ............. 607/61 |
| 5,733,313 A | * | 3/1998 | Barreras et al. ............... 607/33 |
| 5,769,877 A | * | 6/1998 | Barreras, Sr. ................. 607/61 |
| 5,928,272 A | | 7/1999 | Adkins et al. ................. 607/45 |

(Continued)

OTHER PUBLICATIONS

Ira J. Ungar et al. Generation of unidirectionally propagating action potentials using a monopolar electrode cuff, *Annals of Biomedical Engineering*, vol. 14, pp. 437-450.

(Continued)

*Primary Examiner*—Mark W Bockelman

(57) ABSTRACT

A method and system to provide pre-determined electrical pulses for neuromodulating vagus nerve(s) or its branches to provide therapy for bulimia/eating disorders, comprises implantable and external components. The electrical pulses to vagus nerve(s) may be stimulating and/or blocking. The pulsed electrical stimulation/blocking to vagus nerve(s) may be provided using one of the following stimulation systems, such as: a) an implanted stimulus-receiver with an external stimulator; b) an implanted stimulus-receiver comprising a high value capacitor for storing charge, used in conjunction with an external stimulator; c) a programmer-less implantable pulse generator (IPG) which is operable with a magnet; d) a microstimulator; e) a programmable implantable pulse generator; f) a combination implantable device comprising both a stimulus-receiver and a programmable implantable pulse generator (IPG); and g) an implantable pulse generator (IPG) comprising a rechargeable battery. In one embodiment, the external components such as the programmer or external stimulator may comprise a telemetry circuit for networking. The telemetry circuit therefore allows for interrogation or programming of implanted device, from a remote location over a wide area network.

14 Claims, 80 Drawing Sheets

U.S. PATENT DOCUMENTS

| | | | |
|---|---|---|---|
| 6,205,359 B1 | 3/2001 | Boveja | 607/45 |
| 6,356,788 B2 | 3/2002 | Boveja | 607/45 |
| 6,363,282 B1 * | 3/2002 | Nichols et al. | 607/30 |
| 6,449,512 B1 * | 9/2002 | Boveja | 607/41 |
| 6,505,077 B1 | 1/2003 | Kast et al. | 607/61 |
| 6,516,227 B1 | 2/2003 | Meadows et al. | 607/43 |
| 6,553,263 B1 | 4/2003 | Meadows et al. | 607/61 |
| 6,591,137 B1 * | 7/2003 | Fischell et al. | 607/40 |
| 6,609,025 B2 | 8/2003 | Barrett et al. | 607/2 |
| 6,622,041 B2 | 9/2003 | Terry et al. | 607/9 |
| 6,684,105 B2 * | 1/2004 | Cohen et al. | 607/63 |
| 6,708,064 B2 | 3/2004 | Rezai | 607/45 |
| 6,735,475 B1 * | 5/2004 | Whitehurst et al. | 607/46 |
| 6,895,280 B2 | 5/2005 | Meadows et al. | 607/46 |
| 6,941,171 B2 | 9/2005 | Mann et al. | 607/39 |
| 7,212,110 B1 * | 5/2007 | Martin et al. | 340/539.12 |
| 2005/0102006 A1 | 5/2005 | Whitehurst et al. | 607/46 |

OTHER PUBLICATIONS

James D. Sweeney, et al. An asymmetric two electrode cuff for generation of unidirectionally propagated action potentials, *IEEE Transactions on Biomedical Engineering*, vol. BME-33, No. 6, Jun. 1986.

Gregory G. Naples. et al. A spiral nerve cuff electrode for peripheral nerve stimulation, *IEEE Transactions on Biomedical Engineering*, vol. 35, No. 11, Nov. 1988.

James D. Sweeney, et al. A nerve cuff technique for selective excitation of peripheral nerve trunk regions, *IEEE Transactions on Biomedical Engineering*, vol. 37, No. 7, Jul. 1990.

Van Den Honert et al. "A technique for collision block of peripheral nerve: Frequency dependence" *IEEE Transactions on Biomedical Engineering*, MP-12, vol. 28, pp. 379-382, 1981.

D.M Fitzpatrick et al. A nerve cuff design for the selective activation and blocking of myelinated nerve fibers *Ann. Conf. of the IEEE Engineering in Medicine and Biology Soc.*, vol. 13, No. 2, p. 906, 1991.

Rijkhof, et al. Orderly recruitment of motoneurons in an acute rabbit model", " *Ann. Conf. of the IEEE Engineering in Medicine and Biology Soc.*, 20, No. 5, p. 2564, 1998.

R. Bratta. Orderly stimulation of skeletal muscle motor units with tripolar nerve cuff electrode, *IEEE Transactions on Biomedical Engineering*, 36, No. 8, pp. 836, 1989.

Ed. M.A. Arbib, M. Devor "Pain Networks", Handbook of Brand Theory and Neural Networks, MIT Press, p. 698, 1998.

* cited by examiner

| Axons from skin | A α | Aβ | Aδ | C |
|---|---|---|---|---|
| Axons from muscles | Group I | II | III | IV |
| Diameter (μm) | 13-20 | 6-12 | 1-5 | 0.2-1.5 |
| Speed (m/sec) | 80-120 | 35-75 | 5-30 | 0.5-2 |
| Sensory receptors | Proprioceptors of skeletal muscle | Mechano-receptors of skin | Pain temperature | Temperature, pain, itch |

FIG. 2

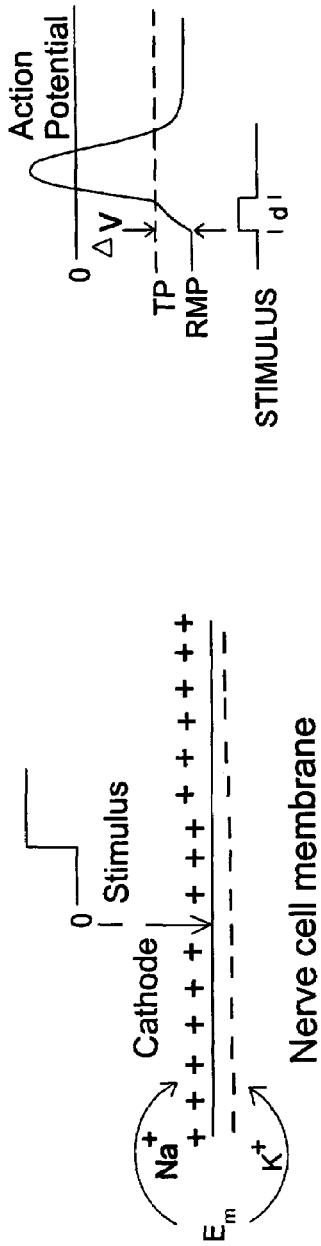
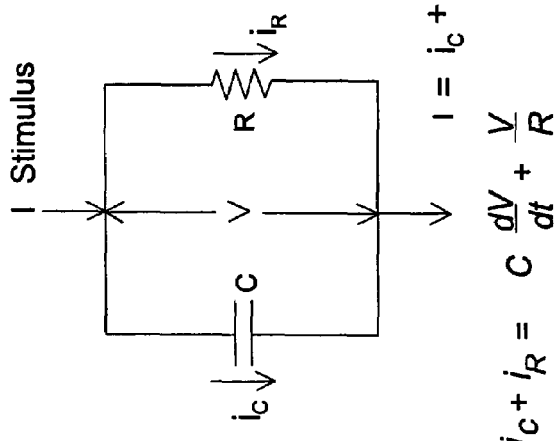
FIG. 5B
FIG. 5C
FIG. 5A
$I = i_C + i_R = C\dfrac{dV}{dt} + \dfrac{V}{R}$

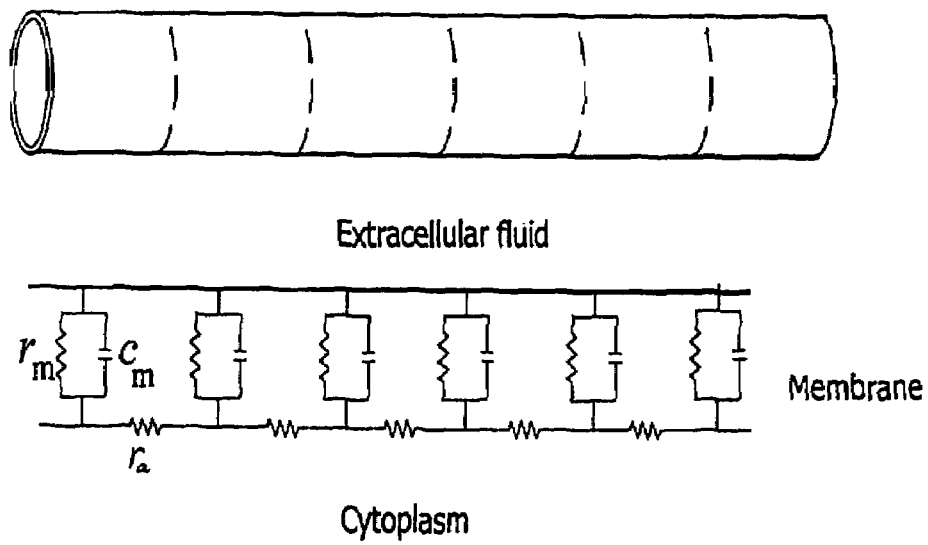
FIG. 6
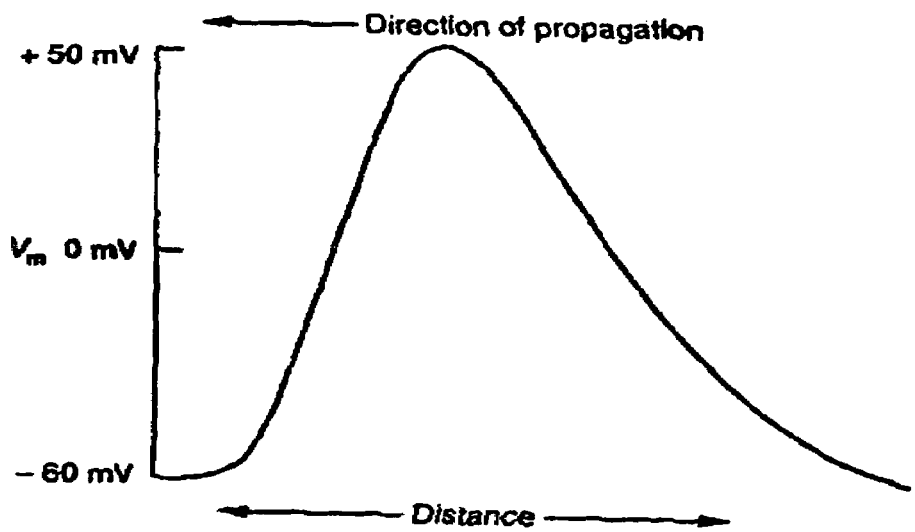
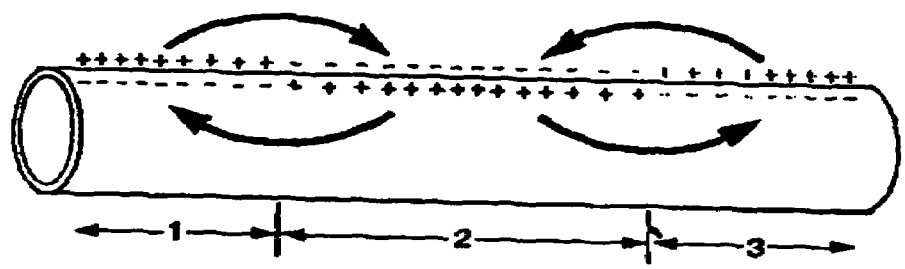
FIG. 7

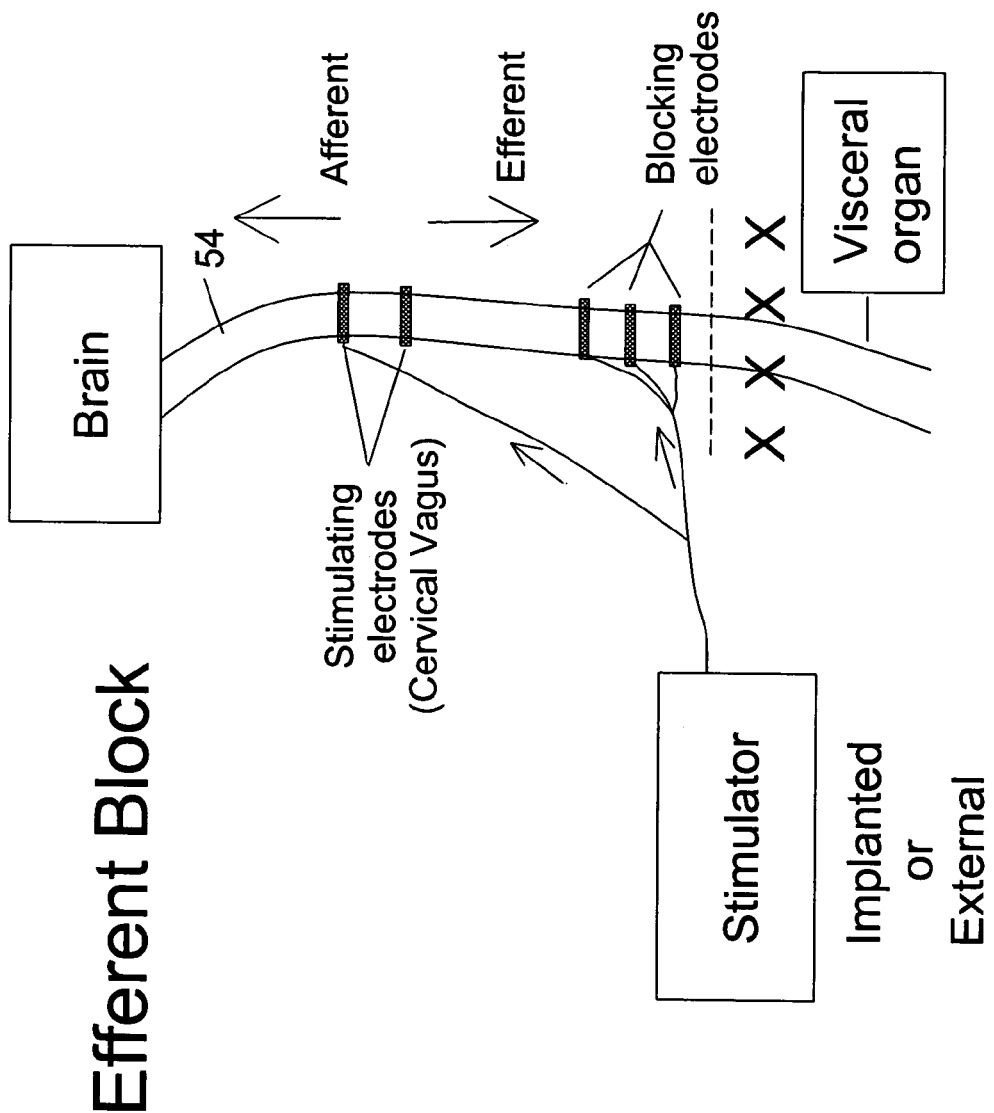

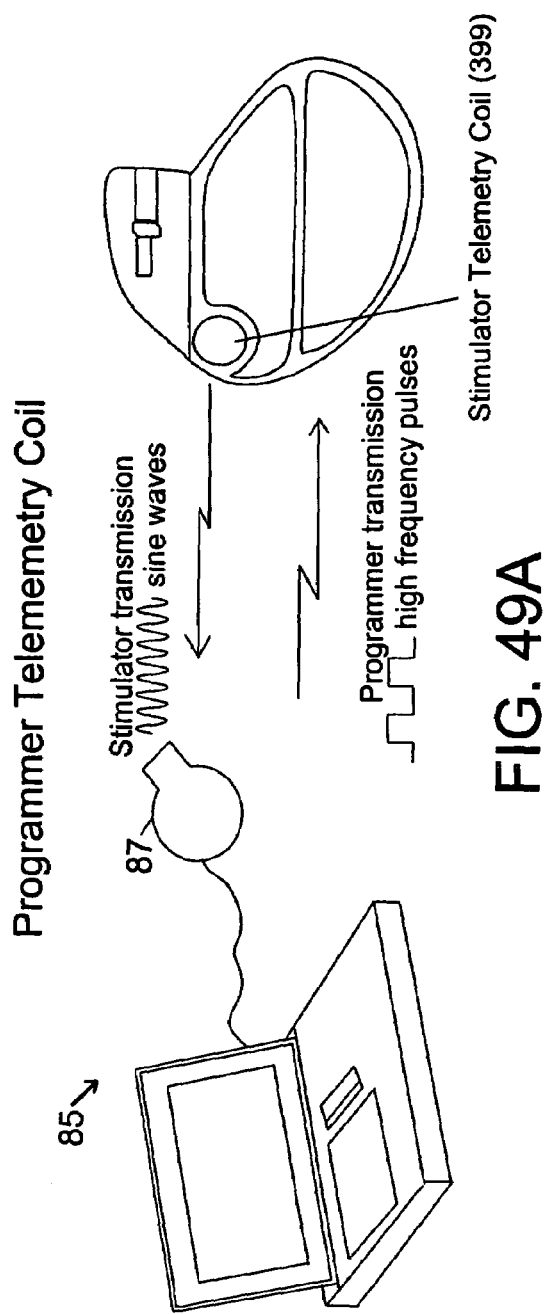
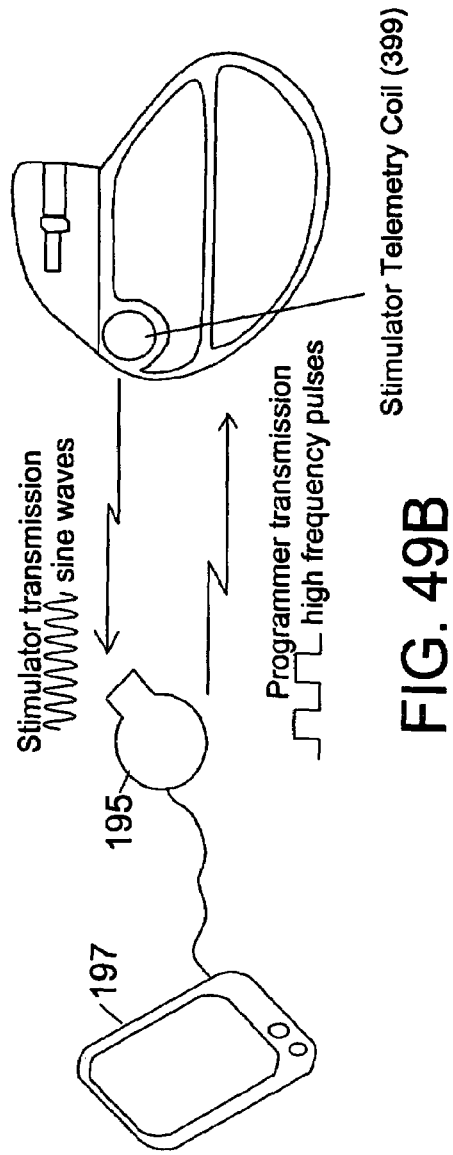
FIG. 49A
FIG. 49B

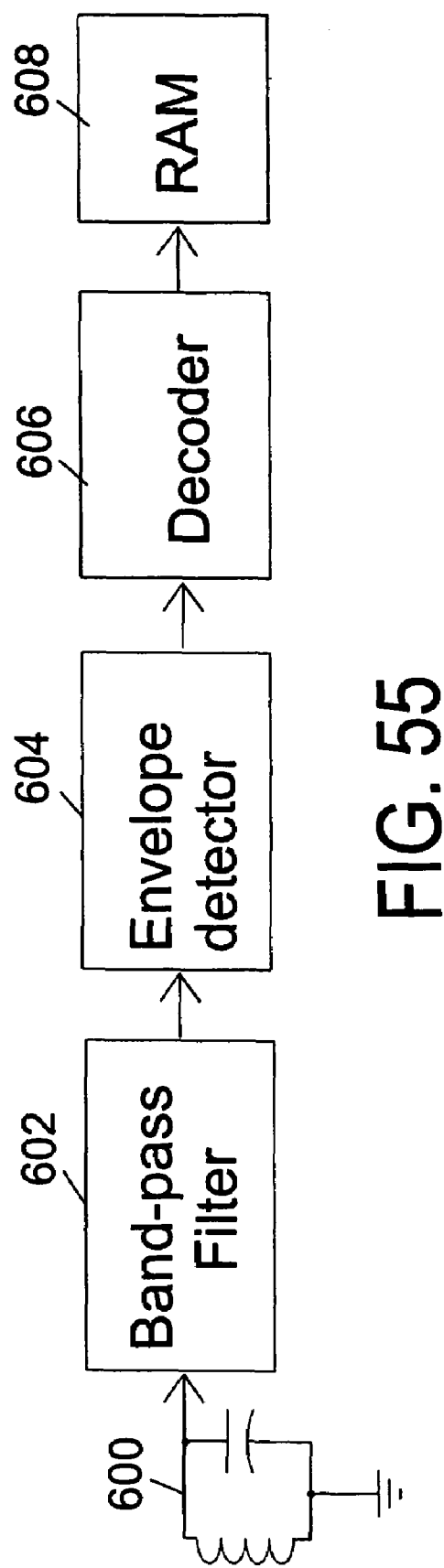
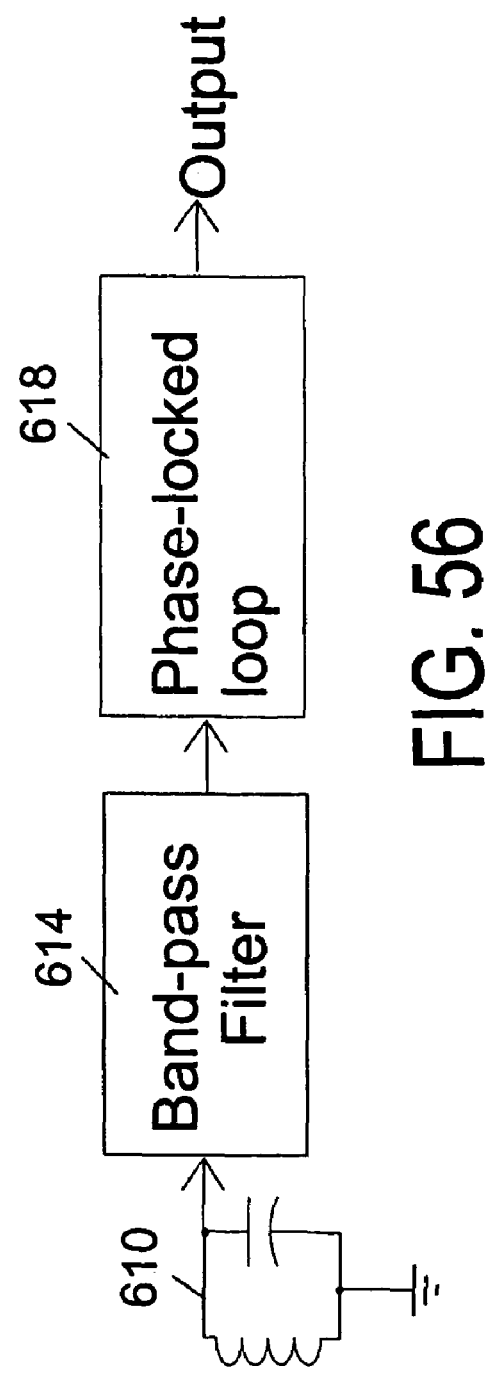

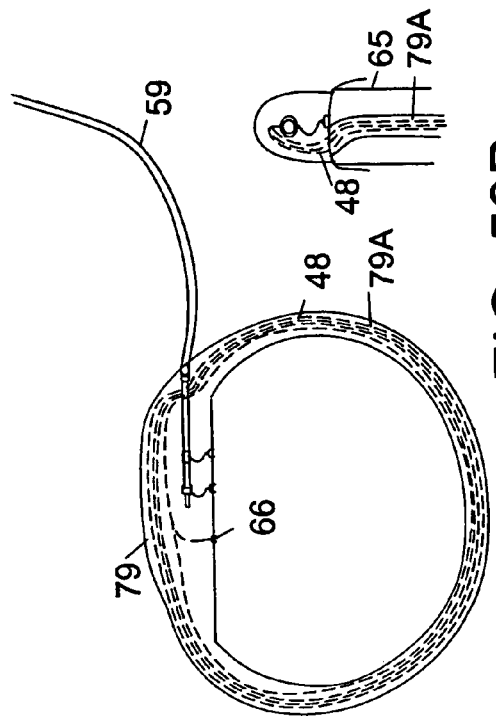
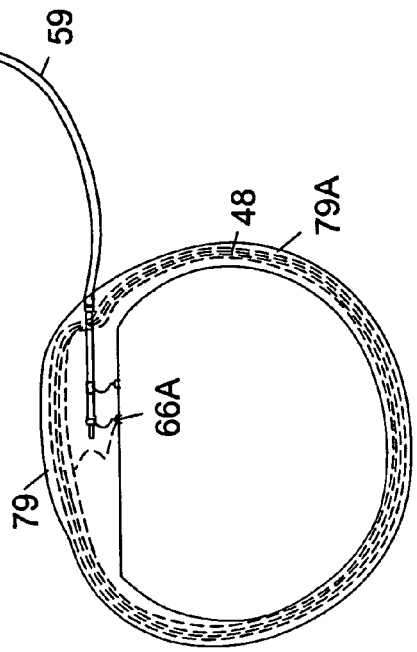
FIG. 59A
FIG. 59B
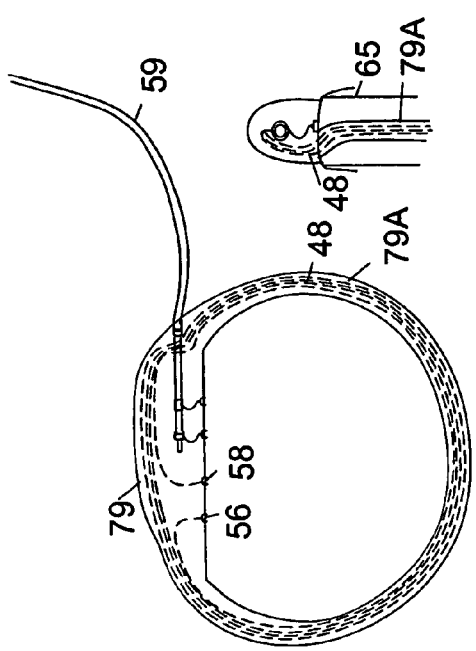
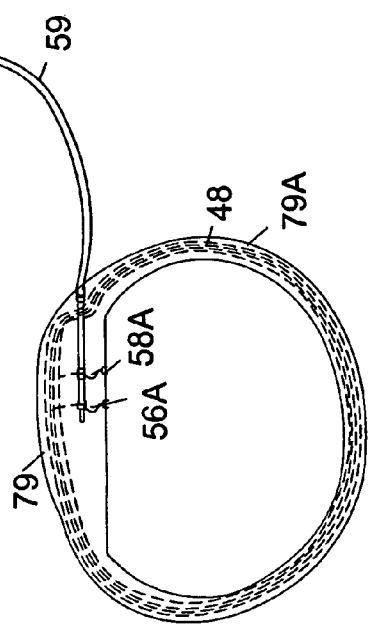
FIG. 59C
FIG. 59D

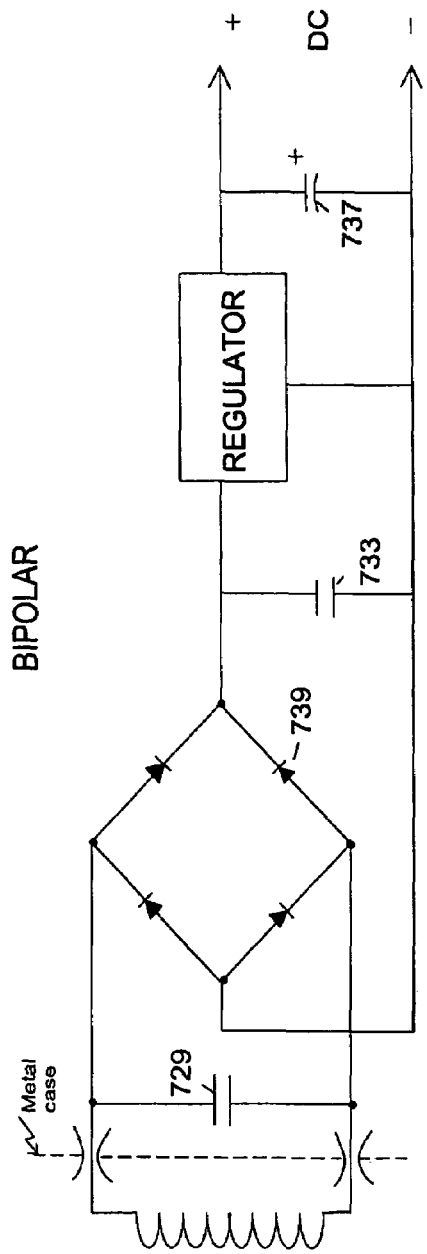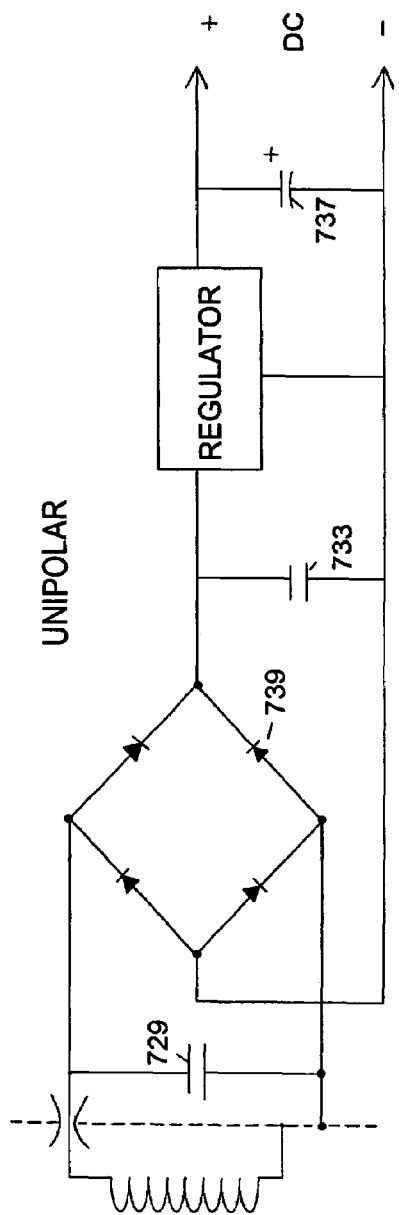

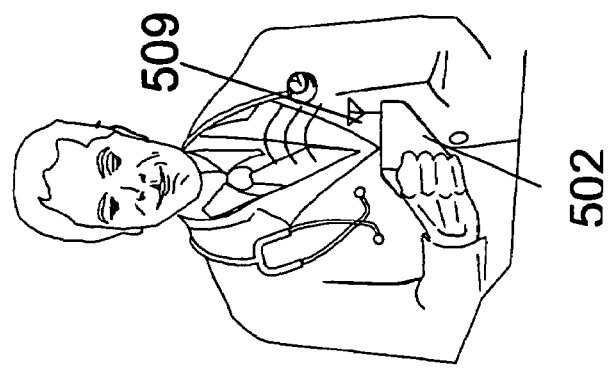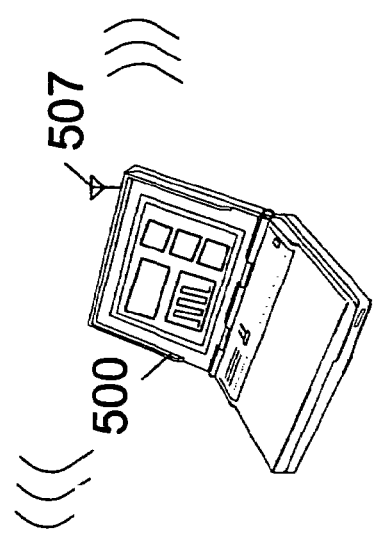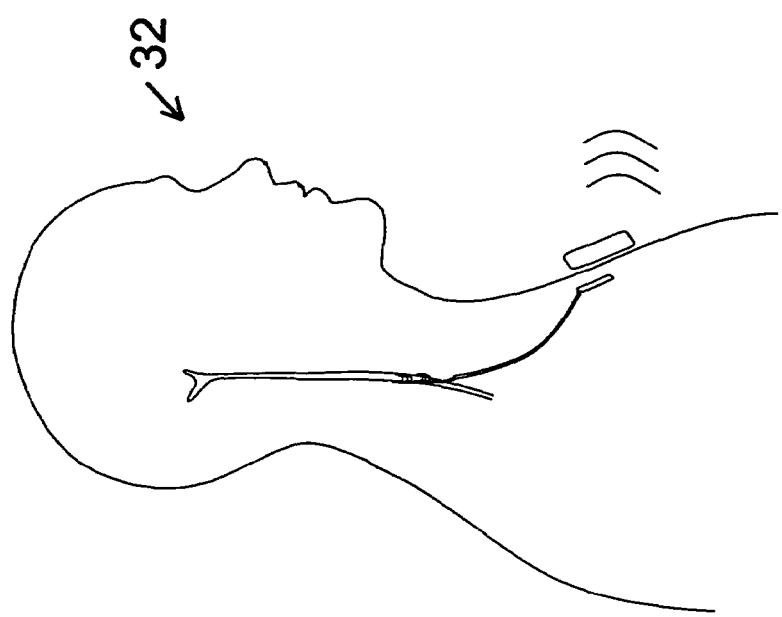
FIG. 72

METHOD AND SYSTEM FOR PROVIDING THERAPY FOR BULIMIA/EATING DISORDERS BY PROVIDING ELECTRICAL PULSES TO VAGUS NERVE(S)

This application is a continuation of application Ser. No. 10/436,017 filed May 11, 2003 now U.S. Pat. No. 7,191,012, entitled "METHOD AND SYSTEM FOR PROVIDING PULSED ELECTRICAL STIMULATION TO A CRANIAL NERVE OF A PATIENT TO PROVIDE THERAPY FOR NEUROLOGICAL AND NEUROPSYCHIATRIC DISORDERS". The prior application being incorporated herein in its entirety by reference, and priority is claimed from the above application.

FIELD OF INVENTION

The present invention relates to neuromodulation, more specifically to provide therapy for bulimia/eating disorders by neuromodulating vagus nerve(s) with pulsed electrical stimulation and/or blocking.

BACKGROUND

Bulimia is a term that means "binge eating". This behavior has become a common practice among female students in universities and, more recently, in high schools. Not all persons who engage in binge eating require a psychiatric diagnosis. Bulimia can also occur in a normal weight condition associated with psychological symptomatology.

Bulimia nervosa is a disorder in which the behavior of bulimia or binge eating is the predominant behavior. Binge eating is defined as an episodic, uncontrolled, rapid ingestion of large quantities of food over a short period. Abdominal pain or discomfort, self-induced vomiting, sleep, or social interruption terminates the bulimic episode. Feelings of guilt, depression, or self-disgust follow. Bulimic patients often use cathartics for weight control and have an eating pattern of alternate binges and fasts. Bulimic patients have a fear of not being able to stop eating voluntarily. The food consumed during a binge usually has a highly dense calorie content and a texture that facilitates rapid eating. Frequent weight fluctuations occur but without the severity of weight loss present in anorexia nervosa.

In a recent study at the university of Minnesota's Neuroscience Research Center, six patients were studied to evaluate if supplying pulses to the vagus nerve(s) reduces the episodes of binging and vomiting that are the hallmark of bulimia by reversing the physiological changes that occur in the function of the vagus nerve. All patients reported significant reductions in episodes of binging/vomiting. Even more impressive was that the women taking part in the study had severe bulimia and had not responded to numerous traditional treatments.

This patent application is directed to providing electrical pulses to vagal nerve(s) for selective stimulation and/or blocking, to provide therapy or to alleviate the symptoms of bulimia/eating disorders. The method and system to provide electrical pulses may comprise both implantable and external components.

Background of Bulimia/Eating Disorders

Bulimia nervosa usually begins after a period of dieting of a few weeks to a year or longer. The dieting may or may not have been successful in achieving weight loss. Most binge eating episodes are followed by self-induced vomiting. Episodes are less frequently followed by use of laxatives. A minority of bulimic patients use diuretics for weight control. The average length of a bingeing episode is about 1 hour. Most patients learn to vomit by sticking their fingers down their throat, and after a short time they learn to vomit on a reflex basis. Most bulimic patients do not eat regular meals and have difficulty feeling satiety at the end of a normal meal. Bulimic patients usually prefer to eat alone and at their homes. About one-fourth to one-third of patients with bulimia nervosa have had previous history of anorexia nervosa.

The majority of bulimic patients have depressive signs and symptoms. They have problems with interpersonal relationships, self-concept, and impulsive behaviors and show high levels of anxiety and compulsivity.

Patients with bulimia nervosa who engage in self-induced vomiting and abuse purgatives or diuretics are susceptible to hypokalemic alkalosis. These patients have electrolyte abnormalities including elevated serum bicarbonate levels, hypochloremia, hypokalemia, and in a few cases, low serum bicarbonate levels, indicating a metabolic acidosis. The latter is particularly true among individuals who abuse laxatives.

Treatment studies of bulimia nervosa have proliferated in the past 15 years, in contrast to the relatively few treatment studies of anorexia nervosa. Multiple controlled drug treatment studies have also been conducted in the past decade. Often a variety of therapy techniques such as cognitive therapy, behavior therapy, and drug treatment may be used together in either individual or group therapy. For treatment resistant cases, modulation of vagus nerve(s) with pulsed electrical stimulation appears to be a promising adjunct therapy.

Background of Vagus Nerve(s)

The 10th cranial nerve or the vagus nerve plays a role in mediating afferent information from visceral organs to the brain. The vagus nerve arises directly from the brain, but unlike the other cranial nerves extends well beyond the head. At its farthest extension it reaches the lower parts of the intestines. The vagus nerve provides an easily accessible, peripheral route to modulate central nervous system (CNS) function. Observations on the profound effect of electrical stimulation of the vagus nerve on central nervous system (CNS) activity extends back to the 1930's. The present invention is primarily directed to selective electrical stimulation or neuromodulation of vagus nerve, for providing adjunct therapy for bulimia/eating disorders.

In the human body there are two vagal nerves (VN), the right VN and the left VN. Each vagus nerve is encased in the carotid sheath along with the carotid artery and jugular vein. The innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is known that stimulation of the left vagus nerve does not cause substantial slowing of the heart rate or cause any other significant deleterious side effects.

Background of Neuromodulation

One of the fundamental features of the nervous system is its ability to generate and conduct electrical impulses. Most nerves in the human body are composed of thousands of fibers of different sizes. This is shown schematically in FIG. 1. The different sizes of nerve fibers, which carry signals to and from the brain, are designated by groups A, B, and C. The vagus nerve, for example, may have approximately 100,000 fibers of the three different types, each carrying signals. Each axon or fiber of that nerve conducts only in one direction, in normal circumstances. In the vagus nerve sensory fibers (afferent) outnumber parasympathetic fibers four to one.

In a cross section of peripheral nerve it is seen that the diameter of individual fibers vary substantially, as is also shown schematically in FIG. 2. The largest nerve fibers are approximately 20 μm in diameter and are heavily myelinated (i.e., have a myelin sheath, constituting a substance largely composed of fat), whereas the smallest nerve fibers are less than 1 μm in diameter and are unmyelinated.

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially in the form of the action potential, are taken into consideration when defining the groups. The smallest fibers (group C) are unmyelinated and have the slowest conduction rate, whereas the myelinated fibers of group B and group A exhibit rates of conduction that progressively increase with diameter.

Nerve cells have membranes that are composed of lipids and proteins (shown schematically in FIGS. 3A and 3B), and have unique properties of excitability such that an adequate disturbance of the cell's resting potential can trigger a sudden change in the membrane conductance. Under resting conditions, the inside of the nerve cell is approximately −90 mV relative to the outside. The electrical signaling capabilities of neurons are based on ionic concentration gradients between the intracellular and extracellular compartments. The cell membrane is a complex of a bilayer of lipid molecules with an assortment of protein molecules embedded in it (FIG. 3A), separating these two compartments. Electrical balance is provided by concentration gradients which are maintained by a combination of selective permeability characteristics and active pumping mechanism.

The lipid component of the membrane is a double sheet of phospholipids, elongated molecules with polar groups at one end and the fatty acid chains at the other. The ions that carry the currents used for neuronal signaling are among these water-soluble substances, so the lipid bilayer is also an insulator, across which membrane potentials develop. In biophysical terms, the lipid bilayer is not permeable to ions. In electrical terms, it functions as a capacitor, able to store charges of opposite sign that are attracted to each other but unable to cross the membrane. Embedded in the lipid bilayer is a large assortment of proteins. These are proteins that regulate the passage of ions into or out of the cell. Certain membrane-spanning proteins allow selected ions to flow down electrical or concentration gradients or by pumping them across.

These membrane-spanning proteins consist of several subunits surrounding a central aqueous pore (shown in FIG. 3B). Ions whose size and charge "fit" the pore can diffuse through it, allowing these proteins to serve as ion channels. Hence, unlike the lipid bilayer, ion channels have an appreciable permeability (or conductance) to at least some ions. In electrical terms, they function as resistors, allowing a predicable amount of current flow in response to a voltage across them.

A nerve cell can be excited by increasing the electrical charge within the neuron, thus increasing the membrane potential inside the nerve with respect to the surrounding extracellular fluid. As shown in FIG. 4, stimuli 4 and 5 are subthreshold, and do not induce a response. Stimulus 6 exceeds a threshold value and induces an action potential (AP) 17 which will be propagated. The threshold stimulus intensity is defined as that value at which the net inward current (which is largely determined by Sodium ions) is just greater than the net outward current (which is largely carried by Potassium ions), and is typically around −55 mV inside the nerve cell relative to the outside (critical firing threshold). If however, the threshold is not reached, the graded depolarization will not generate an action potential and the signal will not be propagated along the axon. This fundamental feature of the nervous system i.e., its ability to generate and conduct electrical impulses, can take the form of action potentials 17, which are defined as a single electrical impulse passing down an axon. This action potential 17 (nerve impulse or spike) is an "all or nothing" phenomenon, that is to say once the threshold stimulus intensity is reached, an action potential will be generated.

FIG. 5A illustrates a segment of the surface of the membrane of an excitable cell. Metabolic activity maintains ionic gradients across the membrane, resulting in a high concentration of potassium ($K^+$) ions inside the cell and a high concentration of sodium ($Na^+$) ions in the extracellular environment. The net result of the ionic gradient is a transmembrane potential that is largely dependent on the $K^+$ gradient. Typically in nerve cells, the resting membrane potential (RMP) is slightly less than 90 mV, with the outside being positive with respect to inside.

To stimulate an excitable cell, it is only necessary to reduce the transmembrane potential by a critical amount. When the membrane potential is reduced by an amount $\Delta V$, reaching the critical or threshold potential (TP); Which is shown in FIG. 5B. When the threshold potential (TP) is reached, a regenerative process takes place: sodium ions enter the cell, potassium ions exit the cell, and the transmembrane potential falls to zero (depolarizes), reverses slightly, and then recovers or repolarizes to the resting membrane potential (RMP).

For a stimulus to be effective in producing an excitation, it must have an abrupt onset, be intense enough, and last long enough. These facts can be drawn together by considering the delivery of a suddenly rising cathodal constant-current stimulus of duration d to the cell membrane as shown in FIG. 5B.

Cell membranes can be reasonably well represented by a capacitance C, shunted by a resistance R as shown by a simplified electrical model in diagram 5C, and shown in a more realistic electrical model in FIG. 6, where neuronal process is divided into unit lengths, which is represented in an electrical equivalent circuit. Each unit length of the process is a circuit with its own membrane resistance ($r_m$), membrane capacitance ($c_m$), and axonal resistance ($r_a$).

When the stimulation pulse is strong enough, an action potential will be generated and propagated. As shown in FIG. 7, the action potential is traveling from right to left. Immediately after the spike of the action potential there is a refractory period when the neuron is either unexcitable (absolute refractory period) or only activated to sub-maximal responses by supra-threshold stimuli (relative refractory period). The absolute refractory period occurs at the time of maximal Sodium channel inactivation while the relative refractory period occurs at a later time when most of the $Na^+$ channels have returned to their resting state by the voltage activated $K^+$ current. The refractory period has two important implications for action potential generation and conduction. First, action potentials can be conducted only in one direction, away from the site of its generation, and secondly, they can be generated only up to certain limiting frequencies.

A single electrical impulse passing down an axon is shown schematically in FIG. 8. The top portion of the figure (A) shows conduction over mylinated axon (fiber) and the bottom portion (B) shows conduction over nonmylinated axon (fiber). These electrical signals will travel along the nerve fibers.

The information in the nervous system is coded by frequency of firing rather than the size of the action potential. This is shown schematically in FIG. 9. The bottom portion of the figure shows a train of action potentials 17.

In terms of electrical conduction, myelinated fibers conduct faster, are typically larger, have very low stimulation thresholds, and exhibit a particular strength-duration curve or respond to a specific pulse width versus amplitude for stimulation, compared to unmyelinated fibers. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300-1,000 μs) and a higher amplitude for activation. Because of their very slow conduction, C fibers would not be highly responsive to rapid stimulation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

As shown in FIG. 10A, when the distal part of a nerve is electrically stimulated, a compound action potential is recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories as shown in the Table one below,

TABLE 1

| Fiber Type | Conduction Velocity (m/sec) | Fiber Diameter (μm) | Myelination |
| --- | --- | --- | --- |
| A Fibers | | | |
| Alpha | 70-120 | 12-20 | Yes |
| Beta | 40-70 | 5-12 | Yes |
| Gamma | 10-50 | 3-6 | Yes |
| Delta | 6-30 | 2-5 | Yes |
| B Fibers | 5-15 | <3 | Yes |
| C Fibers | 0.5-2.0 | 0.4-1.2 | No |

FIG. 10B further clarifies the differences in action potential conduction velocities between the Aδ-fibers and the C-fibers. For many of the application of current patent application, it is the slow conduction C-fibers that are stimulated by the pulse generator.

The modulation of nerve in the periphery, as done by the body, in response to different types of pain is illustrated schematically in FIGS. 11 and 12. As shown schematically in FIG. 11, the electrical impulses in response to acute pain sensations are transmitted to brain through peripheral nerve and the spinal cord. The first-order peripheral neurons at the point of injury transmit a signal along A-type nerve fibers to the dorsal horns of the spinal cord. Here the second-order neurons take over, transfer the signal to the other side of the spinal cord, and pass it through the spinothalamic tracts to thalamus of the brain. As shown in FIG. 12, duller and more persistent pain travel by another-slower route using unmyelinated C-fibers. This route made up from a chain of interconnected neurons, which run up the spinal cord to connect with the brainstem, the thalamus and finally the cerebral cortex.

The autonomic nervous system also senses pain and transmits signals to the brain using a similar route to that for dull pain.

Vagus nerve stimulation, as performed by the system and method of the current patent application, is a means of directly affecting central function. FIG. 13 shows cranial nerves have both afferent pathway 19 (inward conducting nerve fibers which convey impulses toward the brain) and efferent pathway 21 (outward conducting nerve fibers which convey impulses to an effector). Vagus nerve is composed of approximately 80% afferent sensory fibers carrying information to the brain from the head, neck, thorax, and abdomen. The sensory afferent cell bodies of the vagus reside in the nodose ganglion and relay information to the nucleus tractus solitarius (NTS).

The vagus nerve is composed of somatic and visceral afferents and efferents. Usually, nerve stimulation activates signals in both directions (bi-directionally). It is possible however, through the use of special electrodes and waveforms, to selectively stimulate a nerve in one direction only (unidirectionally), as described later in this disclosure. The vast majority of vagus nerve fibers are C fibers, and a majority are visceral afferents having cell bodies lying in masses or ganglia in the skull.

In considering the anatomy, the vagus nerve spans from the brain stem all the way to the splenic flexure of the colon. Not only is the vagus the parasympathetic nerve to the thoracic and abdominal viscera, it also the largest visceral sensory (afferent) nerve. Sensory fibers outnumber parasympathetic fibers four to one. In the medulla, the vagal fibers are connected to the nucleus of the tractus solitarius (viceral sensory), and three other nuclei. The central projections terminate largely in the nucleus of the solitary tract, which sends fibers to various regions of the brain (e.g., the thalamus, hypothalamus and amygdala).

As shown in FIG. 14, the vagus nerve emerges from the medulla of the brain stem dorsal to the olive as eight to ten rootlets. These rootlets converge into a flat cord that exits the skull through the jugular foramen. Exiting the Jugular foramen, the vagus nerve enlarges into a second swelling, the inferior ganglion.

In the neck, the vagus lies in a groove between the internal jugular vein and the internal carotid artery. It descends vertically within the carotid sheath, giving off branches to the pharynx, larynx, and constrictor muscles. From the root of the neck downward, the vagus nerve takes a different path on each side of the body to reach the cardiac, pulmonary, and esophageal plexus (consisting of both sympathetic and parasympathetic axons). From the esophageal plexus, right and left gastric nerves arise to supply the abdominal viscera as far caudal as the splenic flexure.

In the body, the vagus nerve regulates viscera, swallowing, speech, and taste. It has sensory, motor, and parasympathetic components. Table two below outlines the innervation and function of these components.

TABLE 2

Vagus Nerve Components

| Component fibers | Structures innervated | Functions |
| --- | --- | --- |
| SENSORY | Pharynx. larynx, esophagus, external ear | General sensation |
| | Aortic bodies, aortic arch | Chemo- and baroreception |
| | Thoracic and abdominal viscera | |

TABLE 2-continued

Vagus Nerve Components

| Component fibers | Structures innervated | Functions |
| --- | --- | --- |
| MOTOR | Soft palate, pharynx, larynx, upper esophagus | Speech, swallowing |
| PARA-SYMPATHETIC | Thoracic and abdominal viscera | Control of cardiovascular system, respiratory and gastrointestinal tracts |

On the Afferent side, visceral sensation is carried in the visceral sensory component of the vagus nerve. As shown in FIGS. 15A and 15B, visceral sensory fibers from plexus around the abdominal viscera converge and join with the right and left gastric nerves of the vagus. These nerves pass upward through the esophageal hiatus (opening) of the diaphragm to merge with the plexus of nerves around the esophagus. Sensory fibers from plexus around the heart and lungs also converge with the esophageal plexus and continue up through the thorax in the right and left vagus nerves. As shown in FIG. 15B, the central process of the nerve cell bodies in the inferior vagal ganglion enter the medulla and descend in the tractus solitarius to enter the caudal part of the nucleus of the tractus solitarius. From the nucleus, bilateral connections important in the reflex control of cardiovascular, respiratory, and gastrointestinal functions are made with several areas of the reticular formation and the hypothalamus.

The afferent fibers project primarily to the nucleus of the solitary tract (shown schematically in FIGS. 16 and 17) which extends throughout the length of the medulla oblongata. A small number of fibers pass directly to the spinal trigeminal nucleus and the reticular formation. As shown in FIG. 16, the nucleus of the solitary tract has widespread projections to cerebral cortex, basal forebrain, thalamus, hypothalamus, amygdala, hippocampus, dorsal raphe, and cerebellum. Because of the widespread projections of the Nucleus of the Solitary Tract, neuromodulation of the vagal afferent nerve fibers provide therapy and alleviation of symptoms of bulimia/eating disorders.

Prior Art Teachings and Applicant's Methodology

The prior art teachings of Zabara and Wernicke in general relies on the fact, that in anesthetized animals stimulation of vagal nerve afferent fibers evokes detectable changes of the EEG in all of these regions, and that the nature and extent of these EEG changes depends oh the stimulation parameters. They postulated (Wernicke et al. 5,269,303) that synchronization of the EEG may be produced when high frequency (>70 Hz) weak stimuli activate only the myelinated (A and B) nerve fibers, and that desynchronization of the EEG occurs when intensity of the stimulus is increased to a level that activates the unmyelinated (C) nerve fibers.

The applicant's methodology is different, and among other things is based on cumulative effects of vagus nerve afferent stimulation, and does not rely on VNS-induced EEG changes. This is relevant since an intent of Zabara and Wernicke et al. teachings is to have a feedback system, wherein a sensor in the implantable system responds to EEG changes providing vagus nerve stimulation. Applicant's methodology is based on an open-loop system where the physician determines the parameters for vagus nerve stimulation (and blocking). If the selected parameters are uncomfortable or are not tolerated by the patient, the electrical parameters are re-programmed. Advantageously, according to this disclosure, some re-programming or parameter adjustment may be done from a remote location, over a wide area network. A method of remote communication for neuromodulation therapy system is disclosed in commonly assigned U.S. Pat. No. 6,662,052 B1 and applicant's co-pending application Ser. No. 10/730,513 (Boveja), now U.S. Pat. No. 7,369,897.

It is of interest that clinical investigation (in conscious humans) have not shown VNS-induced changes in the background EEGs of humans. A study, which used awake and freely moving animals, also showed no VNS-induced changes in background EEG activity. Taken together, the findings from animal study and human studies indicate that acute desynchronization of EEG activity is not a prominent feature of VNS when it is administered during physiologic wakefulness and sleep One of the advantages of applicant's open-loop methodology is that pre-determined programs may be used, utilizing an inexpensive implantable pulse generator as disclosed in applicant's commonly assigned U.S. Pat. No. 6,760,626 B1 referred to as Boveja '626 patent. Pre-determined programs define neuromodulation parameters such as pulse amplitude, pulse width, pulse frequency, on-time and off-time. Examples of pre-determined programs are disclosed in applicant's '626 patent, and in this disclosure for both implantable and external pulse generator means. If an activated pre-determined program is uncomfortable for the patient, a different pre-determined program may be activated or the program may be selectively modified.

Another advantage of applicant's methodology is that, at any given time a patient will receive the most aggressive therapy that is well tolerated. Since the therapy is cumulative the clinical benefits will be realized quicker In summary, applicant's invention is based on an open-loop pulse generator means utilizing pre-determined (pre-packaged programs), where the effects of the therapy and clinical benefits are cumulative effects, which occur over a period of time with selective stimulation. Prior art teachings (of vagal tuning) point away from using pre-determined (pre-packaged programs).

In the applicant's methodology, after the patient has recovered from surgery (approximately 2 weeks), and the stimulation/blocking is turned ON, nothing happens immediately. After a few weeks of intermittent stimulation, the effects start to become noticeable in some patients. Thereafter, the beneficial effects of pulsed electrical therapy accumulate up to a certain point, and are sustained over time, as the therapy is continued.

Prior Art

U.S. Pat. No. 6,708,064 B2 (Rezai) is generally directed to method for treating neurological conditions by stimulating and sensing in the brain especially in the intraminar nuclei (ILN), for affecting psychiatric disorders.

U.S. Pat. Nos. 4,702,254, 4,867,164 and 5,025,807 (Zabara) generally disclose animal research and experimentation related to epilepsy and the like. Applicant's method of neuromodulation is significantly different than that disclosed in Zabara '254, '164' and '807 patents.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy needs to be continuously sustained over a prolonged period of time. The methodology disclosed is focused on circuitry within the receiver, which would not be sufficient when the transmitting coil and receiving coil assume significantly different orientation, which is likely in the current application.

U.S. Pat. No. 5,299,569 (Wernicke et al.) is directed to the use of implantable pulse generator technology for treating and controlling neuropsychiatric disorders including schizophrenia, depression, and borderline personality disorder.

U.S. Pat. No. 6,205,359 B1 (Boveja) and U.S. Pat. No. 6,356,788 B2 (Boveja) are directed to adjunct therapy for neurological and neuropsychiatric disorders using an implanted lead-receiver and an external stimulator.

U.S. Pat. No. 5,193,539 (Schulman, et al) is generally directed to an addressable, implantable microstimulator that is of size and shape which is capable of being implanted by expulsion through a hypodermic needle. In the Schulman patent, up to 256 microstimulators may be implanted within a muscle and they can be used to stimulate in any order as each one is addressable, thereby providing therapy for muscle paralysis.

U.S. Pat. No. 5,405,367 (Schulman, et al) is generally directed to the structure and method of manufacture of an implantable microstimulator.

U.S. Pat. No. 6,622,041 B2 (Terry, Jr. et al.) is directed to treatment of congestive heart failure and autonomic cardiovascular drive disorders using implantable neurostimulator.

SUMMARY OF THE INVENTION

The method and system of the current invention provides afferent neuromodulation therapy for bulimia/eating disorders by providing electrical pulses to the vagus nerve(s). This may be in addition to any drug therapy. The method and system comprises both implantable and external components. The power source may also be external or implanted in the body.

Accordingly, in one aspect of the invention pre-determined electrical pulses are provided to vagus nerve(s) to provide therapy or to alleviate symptoms of bulimia/eating disorders. The pulse generator means is capable of providing stimulating and blocking pulses.

In another aspect of the invention, the electrical pulses are provided using an implanted stimulus-receiver adapted to work in conjunction with an external stimulator.

In another aspect of the invention, the electrical pulses are provided using an implanted stimulus-receiver which comprises a high value capacitor for storing charge, and is adapted to work in conjunction with an external stimulator.

In another aspect of the invention, the electrical pulses are provided using a programmer-less implantable pulse generator (IPG) which can be programmed with a magnet.

In another aspect of the invention, the electrical pulses are provided using a microstimulator.

In another aspect of the invention, the electrical pulses are provided using a programmable implantable pulse generator (IPG).

In another aspect of the invention, the electrical pulses are provided using a combination device which comprises both a stimulus-receiver and a programmable implantable pulse generator.

In another aspect of the invention, the electrical pulses are provided using an implantable pulse generator which comprises a re-chargeable battery.

In another aspect of the invention, the selective stimulation to vagus nerve(s) may be anywhere along the length of the nerve, such as at the cervical level or at a level near the diaphram.

In another aspect of the invention, stimulation and/or blocking pulses may be provided.

In another aspect of the invention, the blocking pulses may be at a single site, or at multiple sites.

In another aspect of the invention, the nerve blocking comprises at least one from a group consisting of: DC or anodal block, Wedenski block, and Collision block.

In another aspect of the invention, the external components such as the external stimulator or programmer comprise telemetry means adapted to be networked, for remote interrogation or remote programming of the device.

In another aspect of the invention, the lead may be bipolar, tripolar, or multipolar to provide stimulation and blocking pulses.

In yet another aspect of the invention, the implanted lead comprises at least one electrode selected from the group consisting of spiral electrodes, cuff electrodes, steroid eluting electrodes, wrap-around electrodes, and hydrogel electrodes.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 2 is a diagram showing different types of nerve fibers.

FIGS. 5A, 5B, 5C are schematic illustrations of the electrical properties of nerve cell membrane.

FIG. 6 is a schematic illustration of electrical circuit model of nerve cell membrane.

FIG. 7 is an illustration of propagation of action potential in nerve cell membrane.

FIG. 47E is a diagram depicting electrical stimulation with conduction in the afferent direction and selective organ blocking in the efferent direction.

FIGS. 49A and 49B are diagrams showing communication of programmer with the implanted stimulator.

FIG. 55 shows a diagram of receiving and decoding circuitry for programming data.

FIG. 56 shows a diagram of receiving and decoding circuitry for telemetry data.

FIG. 59A depicts coil around the titanium case with two feedthroughs for a bipolar configuration.

FIG. 59B depicts coil around the titanium case with one feedthrough for a unipolar configuration.

FIG. 59C depicts two feedthroughs for the external coil which are common with the feedthroughs for the lead terminal.

FIG. 59D depicts one feedthrough for the external coil which is common to the feedthrough for the lead terminal.

FIG. 63A depicts bipolar version of stimulus-receiver module.

FIG. 63B depicts unipolar version of stimulus-receiver module.

FIGS. 67A and 67B depict recharge coil on the titanium case with a magnetic shield in between.

FIG. 72 depicts remote monitoring of stimulation devices.

DETAILED DESCRIPTION OF THE INVENTION

Figure 1:
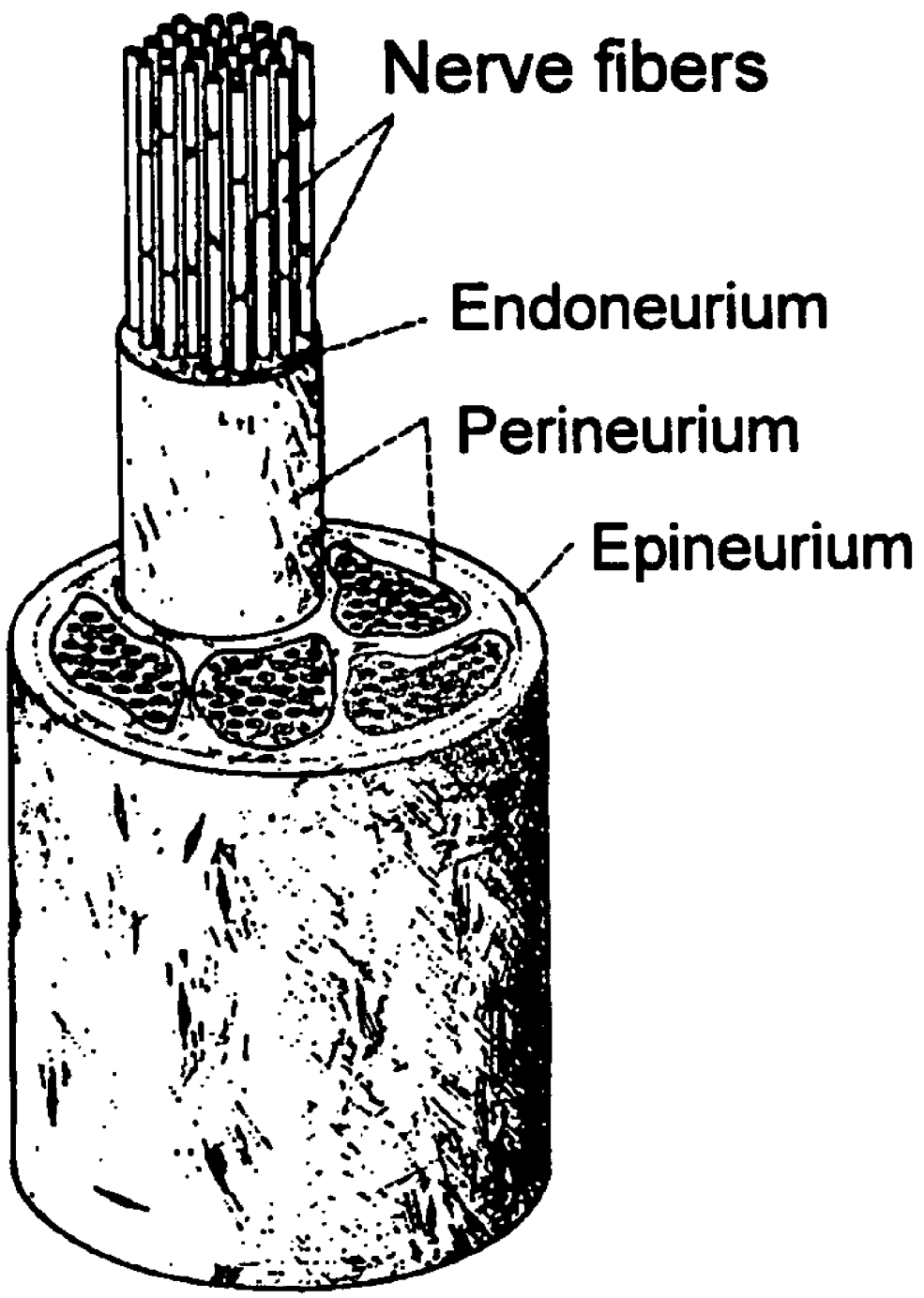
FIG. 1 is a diagram of the structure of a nerve.
Figure 3:
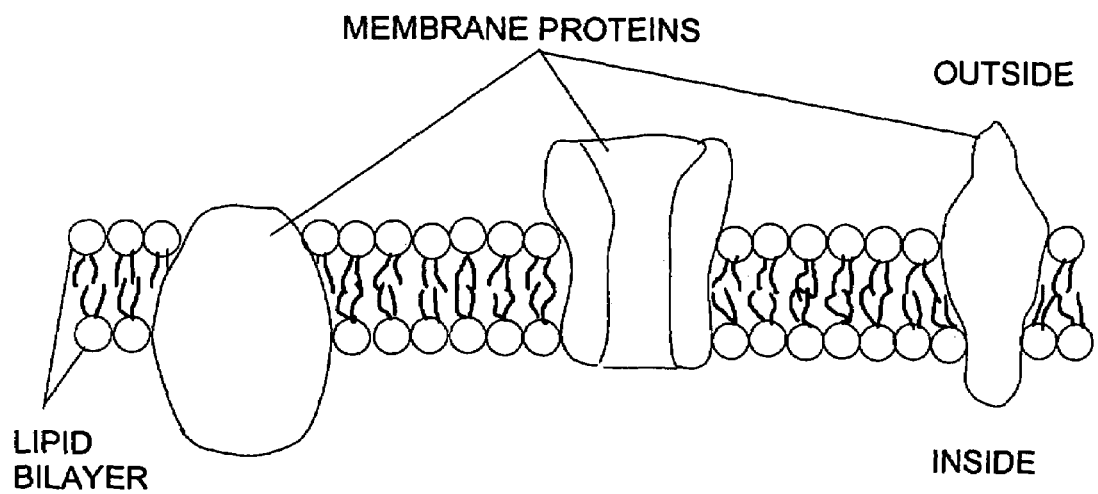
FIGS. 3A and 3B are schematic illustrations of the biochemical makeup of nerve cell membrane.
Figure 3:
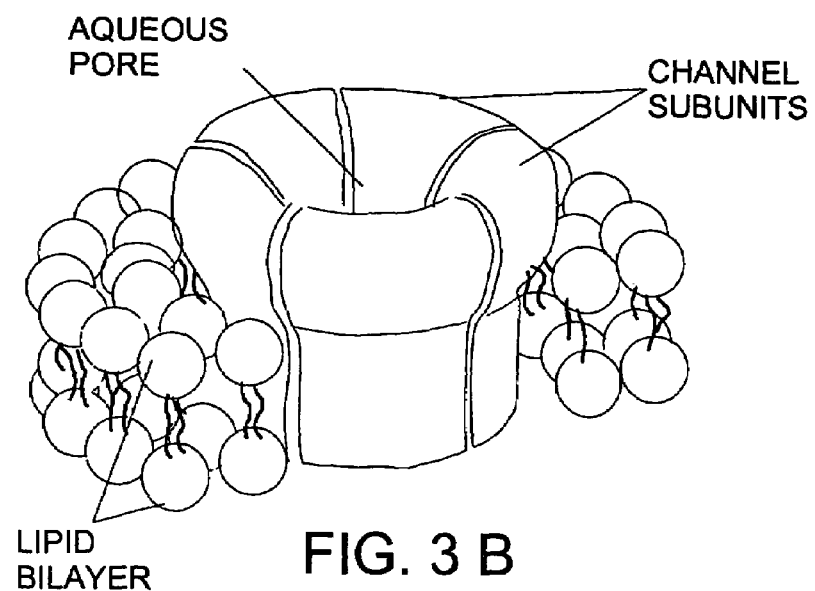
Figure 4:
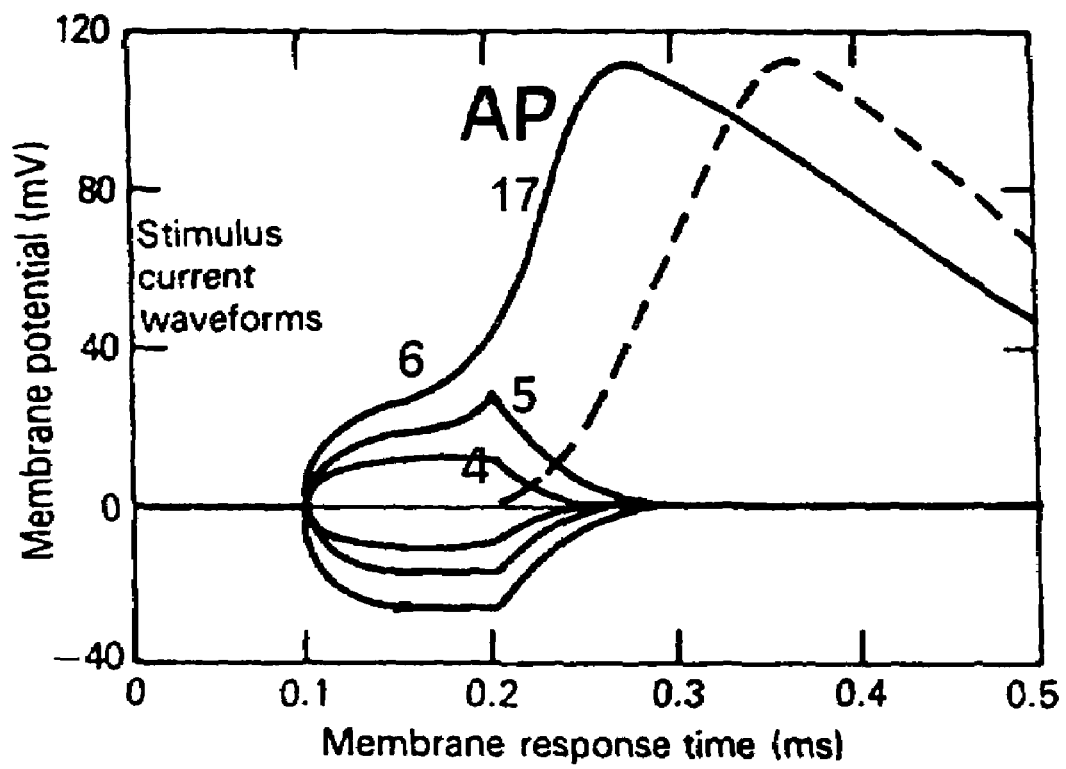
FIG. 4 is a figure demonstrating subthreshold and suprathreshold stimuli.
Figure 8:
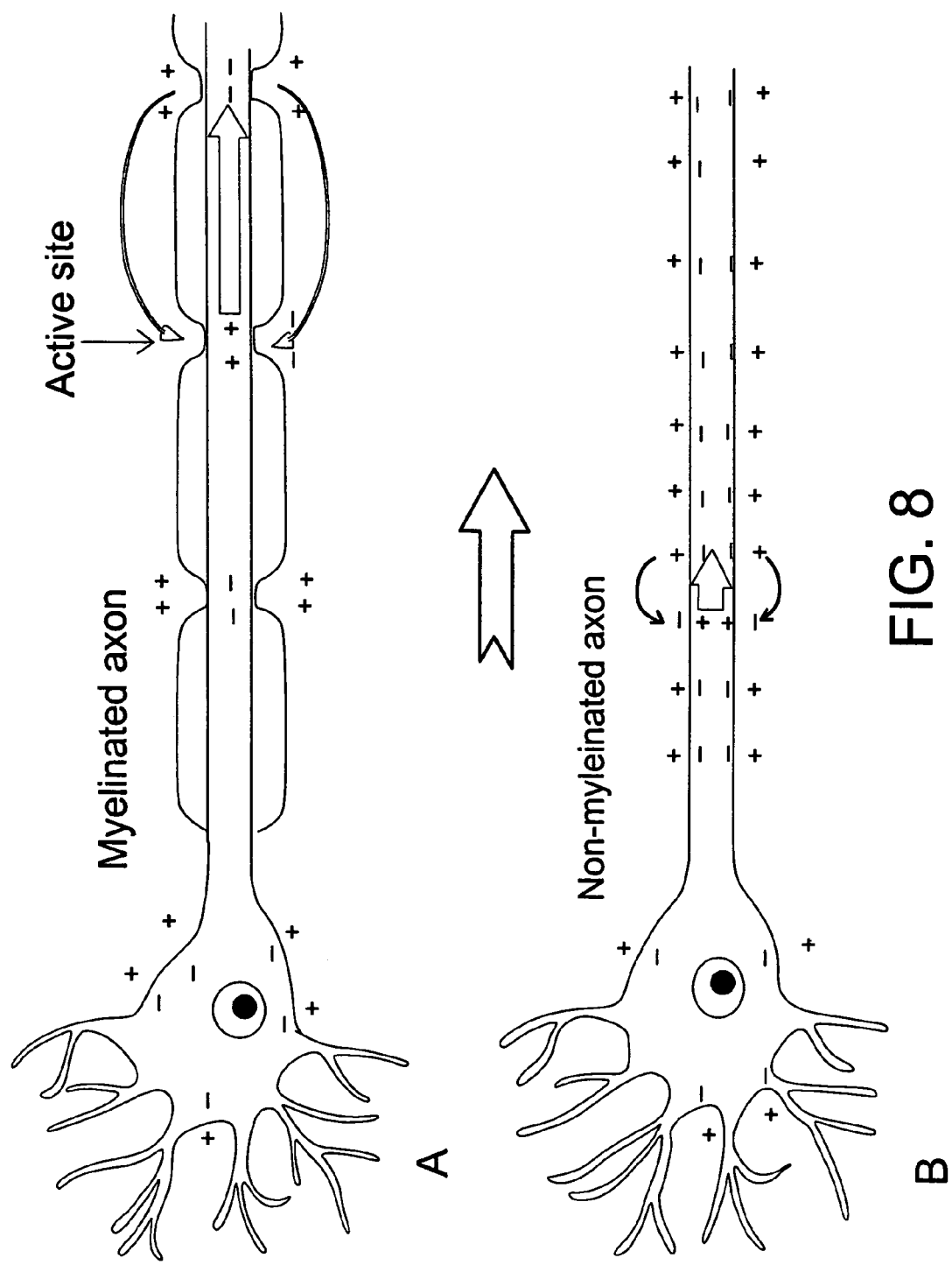
FIG. 8 is an illustration showing propagation of action potential along a myelinated axon and non-myelinated axon.
Figure 9:
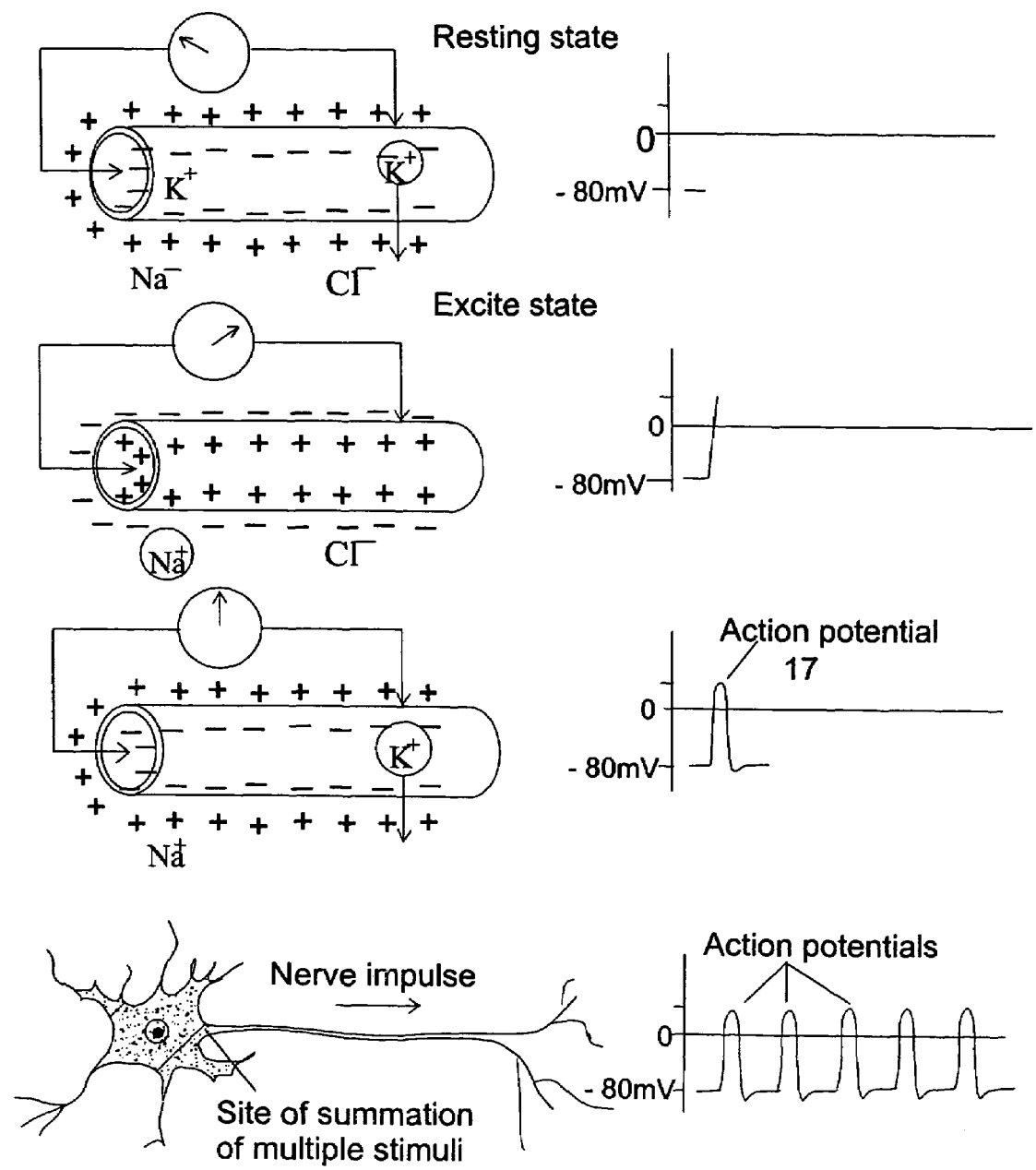
FIG. 9 is an illustration showing a train of action potentials.

The following description is of the best mode presently contemplated for carrying out the invention. This description is not to be taken in a limiting sense, but is made merely for the purpose of describing the general principles of the invention. The scope of the invention should be determined with reference to the claims.

Co-pending patent application Ser. No. 10/195,961, now U.S. Pat. No. 7,062,330, and Ser. No. 10/142,298, now abandoned, are directed to method and system for modulating a vagus nerve ($10^{th}$ Cranial Nerve in the body) using modulated electrical pulses with an inductively coupled stimulation system. In the disclosure of this patent application, the electrical stimulation system comprises both implanted and external components.

In the method and system of this application, selective pulsed electrical stimulation is applied to a vagus nerve(s) for afferent neuromodulation to provide therapy for bulimia/eating disorders. An implantable lead is surgically implanted in the patient. The vagus nerve(s) is/are surgically exposed and isolated. The electrodes on the distal end of the lead are wrapped around the vagus nerve(s), and the lead is tunneled subcutaneously. A pulse generator means is connected to the proximal end of the lead. The power source may be external, implantable, or a combination device.

Patient's with bulemia/eating disorders tend to be young. So many of the patients may end up with more than one type of pulse generator in their lifetime. In the methodology of this invention, an implanted lead has a terminal end which is compatible with different embodiments of pulse generators disclosed in this application. Once the lead is implanted in a patent, any embodiment of the pulse generator disclosed in this application, may be implanted in the patient. Furthermore, at replacement the same embodiment or a different embodiment may be implanted in the patient using the same lead. This may be repeated as long as the implanted lead is functional and maintains its integrity.

As one example, without limitation, an implanted stimulus-receiver in conjunction with an external stimulator may be used initially to test patient's response. At a later time, the pulse generator may be exchanged for a more elaborate implanted pulse generator (IPG) model, keeping the same lead. Some examples of stimulation and power sources that may be used for the practice of this invention, and disclosed in this Application, include:

a) an implanted stimulus-receiver with an external stimulator;

b) an implanted stimulus-receiver comprising a high value capacitor for storing charge, used in conjunction with an external stimulator;

c) a programmer-less implantable pulse generator (IPG) which is operable with a magnet;

d) a microstimulator;

e) a programmable implantable pulse generator;

f) a combination implantable device comprising both a stimulus-receiver and a programmable IPG; and g) an IPG comprising a rechargeable battery.

Implanted Stimulus-Receiver with an External Stimulator

For an external power source, a passive implanted stimulus-receiver may be used. Such a system is disclosed in the parent application Ser. No. 10/142,298, now abandoned and mentioned here for convenience.

Figure 18:
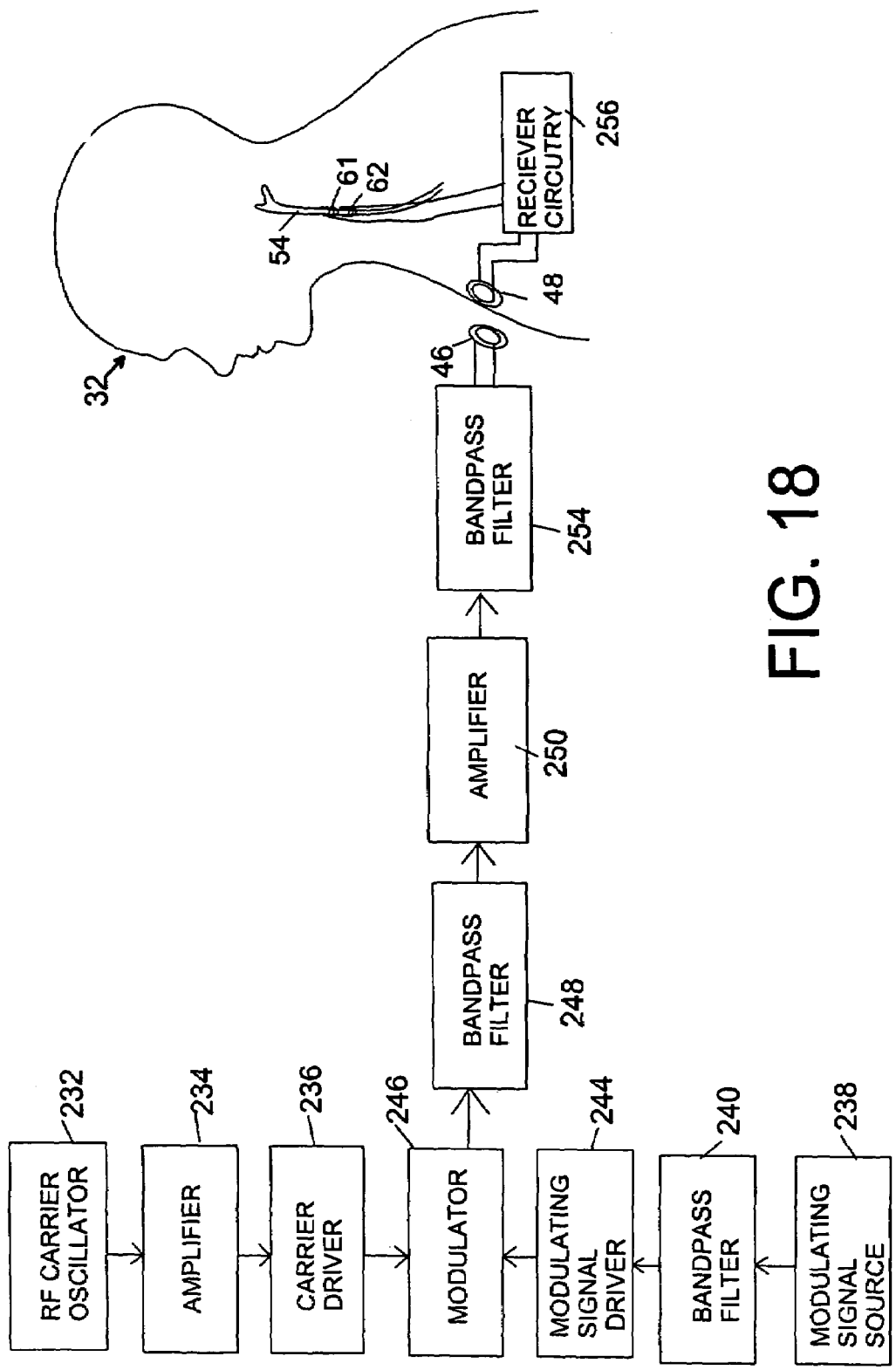
FIG. 18 is a simplified block diagram depicting supplying amplitude and pulse width modulated electromagnetic pulses to an implanted coil.

The selective stimulation of various nerve fibers of a cranial nerve such as the vagus nerve (or neuromodulation of the vagus nerve), as performed by one embodiment of the method and system of this invention is shown schematically in FIG. 18, as a block diagram. A modulator 246 receives analog (sine wave) high frequency "carrier" signal and modulating signal. The modulating signal can be multilevel digital, binary, or even an analog signal. In this embodiment, mostly multilevel digital type modulating signals are used. The modulated signal is amplified 250, conditioned 254, and transmitted via a primary coil 46 which is external to the body. A secondary coil 48 of an implanted stimulus receiver, receives, demodulates; and delivers these pulses to the vagus nerve 54 via electrodes 61 and 62. The receiver circuitry 256 is described later.

The carrier frequency is optimized. One preferred embodiment utilizes electrical signals of around 1 Mega-Hertz, even though other frequencies can be used. Low frequencies are generally not suitable because of energy requirements for longer wavelengths, whereas higher frequencies are absorbed by the tissues and are converted to heat, which again results in power losses.

Figure 19:
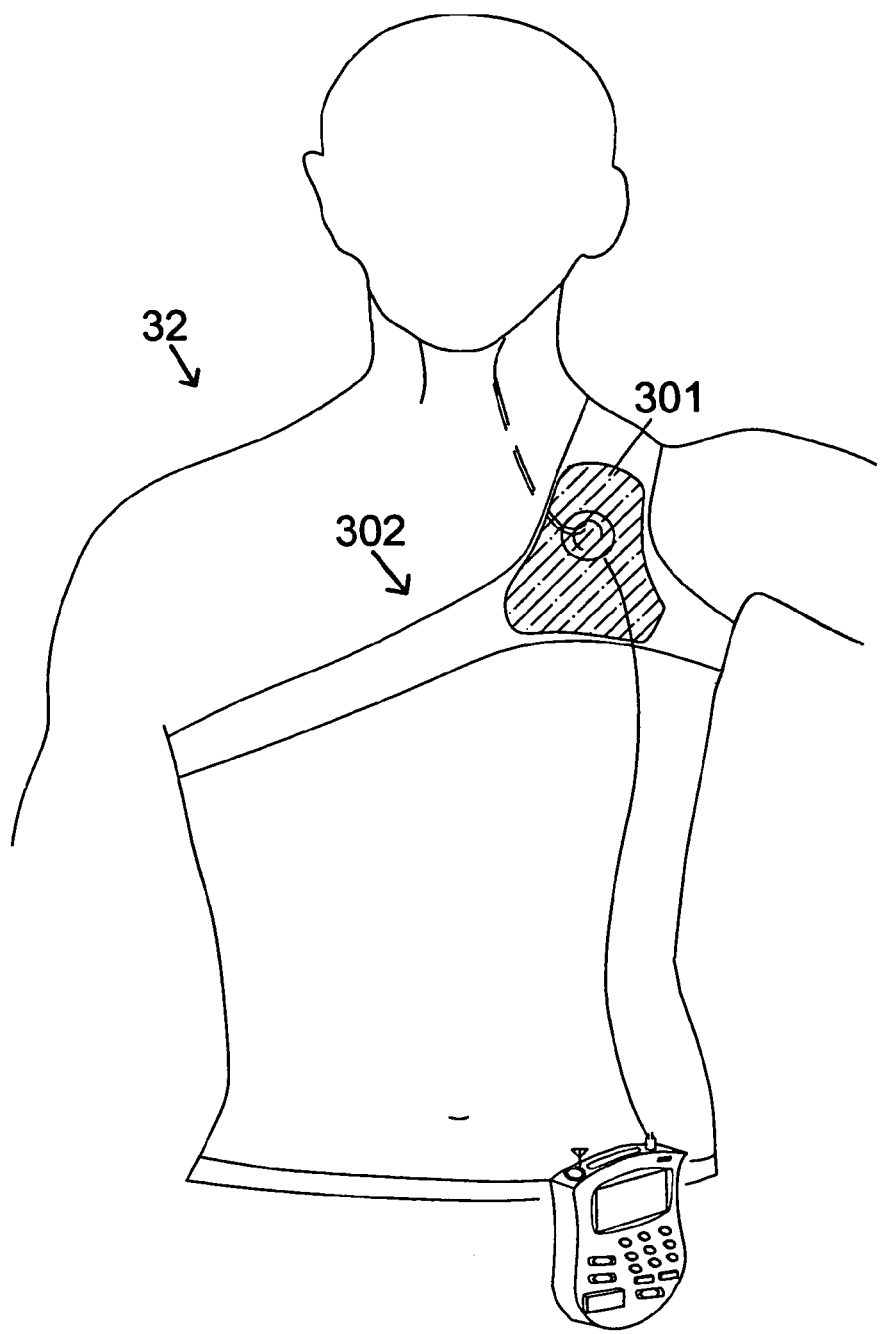
FIG. 19 depicts a customized garment for placing an external coil to be in close proximity to an implanted coil.

Shown in conjunction with FIG. 19, the coil for the external transmitter (primary coil 46) may be placed in the pocket 301 of a customized garment 302, for patient convenience.

Figure 20:
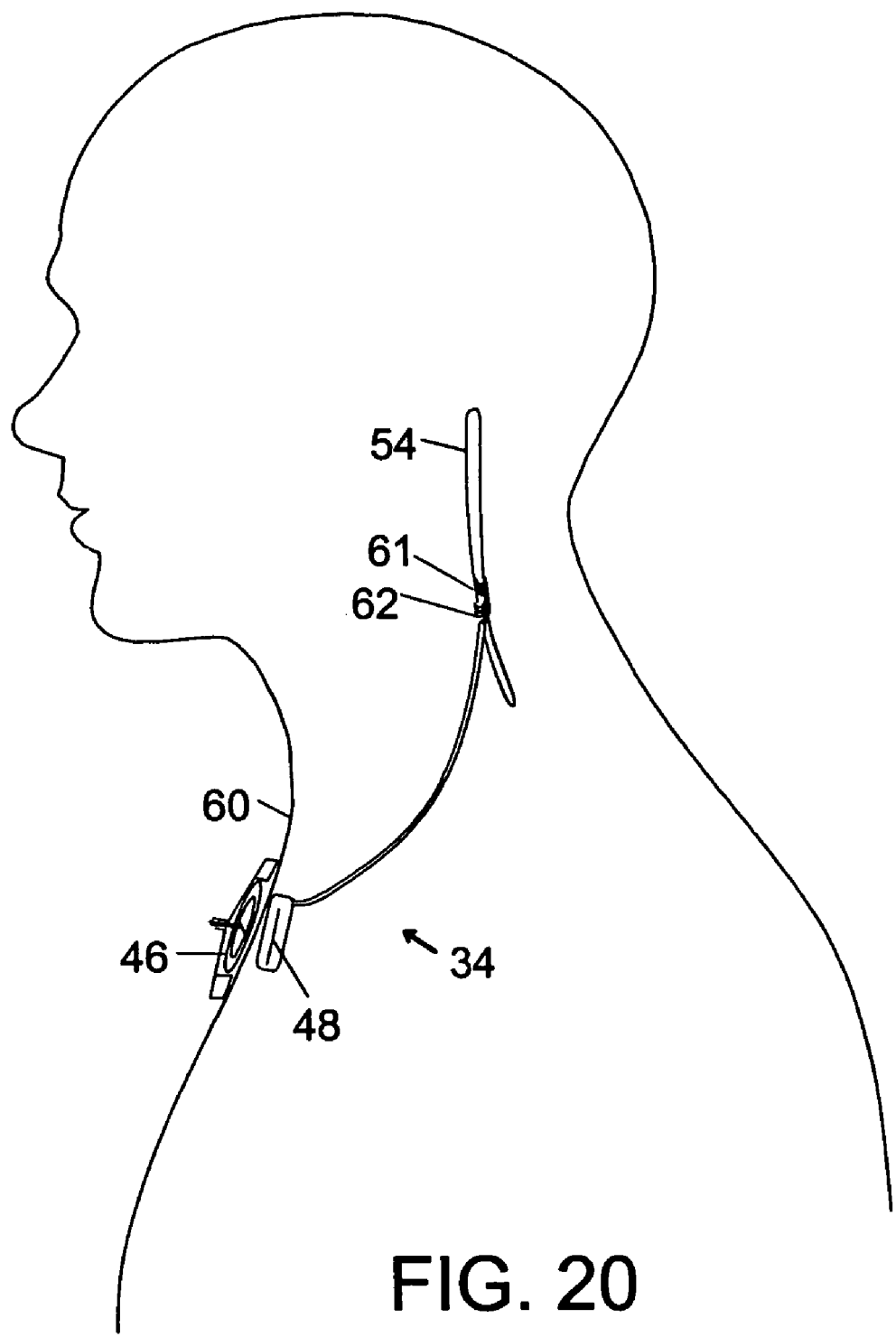
FIG. 20 is a diagram showing the implanted lead-receiver in contact with the vagus nerve at the distal end.

Shown in conjunction with FIG. 20, the primary (external) coil 46 of the external stimulator 42 is inductively coupled to the secondary (implanted) coil 48 of the implanted stimulus-receiver 34. The implantable stimulus-receiver 34 has circuitry at the proximal end, and has two stimulating electrodes at the distal end 61,62. The negative electrode (cathode) 61 is positioned towards the brain and the positive electrode (anode) 62 is positioned away from the brain.

Figure 21:
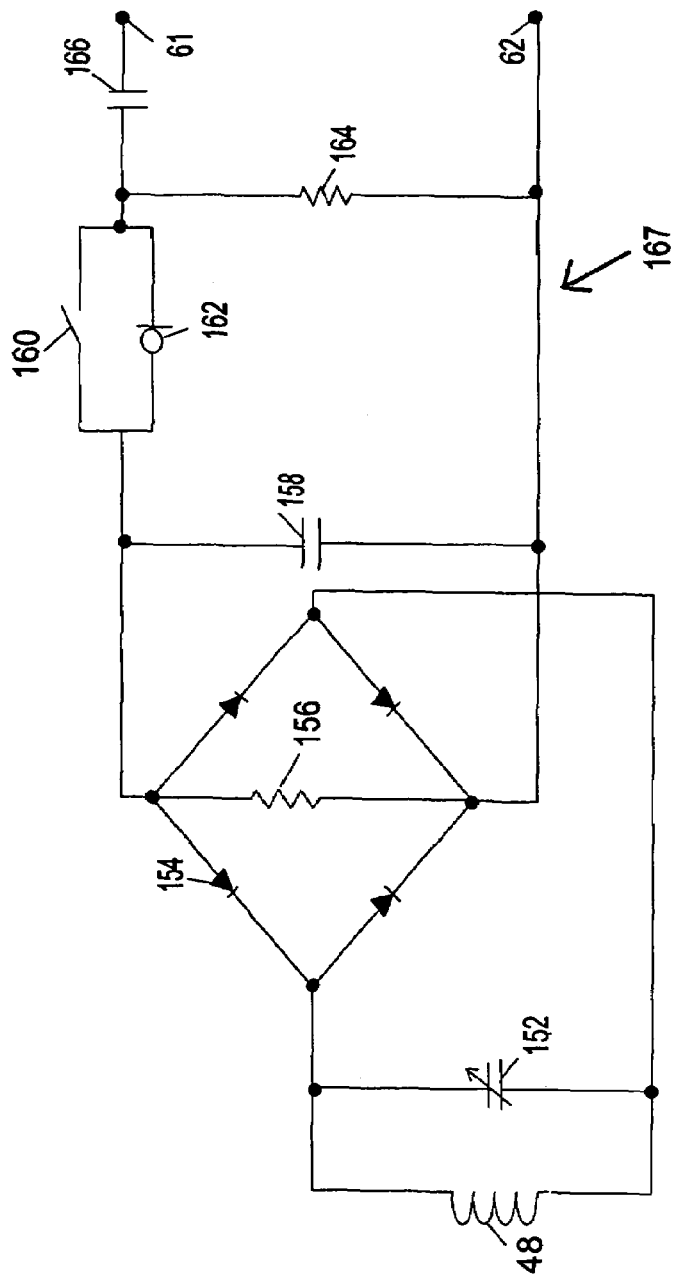
FIG. 21 is a schematic of the passive circuitry in the implanted lead-receiver.

The circuitry contained in the proximal end of the implantable stimulus-receiver 34 is shown schematically in FIG. 21, for one embodiment. In this embodiment, the circuit uses all passive components. Approximately 25 turn copper wire of 30 gauge, or comparable thickness, is used for the primary coil 46 and secondary coil 48. This wire is concentrically wound with the windings all in one plane. The frequency of the pulse-waveform delivered to the implanted coil 48 can vary, and so a variable capacitor 152 provides ability to tune secondary implanted circuit 167 to the signal from the primary coil 46. The pulse signal from secondary (implanted) coil 48 is rectified by the diode bridge 154 and frequency reduction obtained by capacitor 158 and resistor 164. The last component in line is capacitor 166, used for isolating the output signal from the electrode wire. The return path of signal from cathode 61 will be through anode 62 placed in proximity to the cathode 61 for "Bipolar" stimulation. In this embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation and is therefore, preferred in this embodiment. Unipolar stimulation is more likely to stimulate skeletal muscle in addition to nerve stimulation. The implanted circuit 167 in this embodiment is passive, so a battery does not have to be implanted.

Figure 22A:
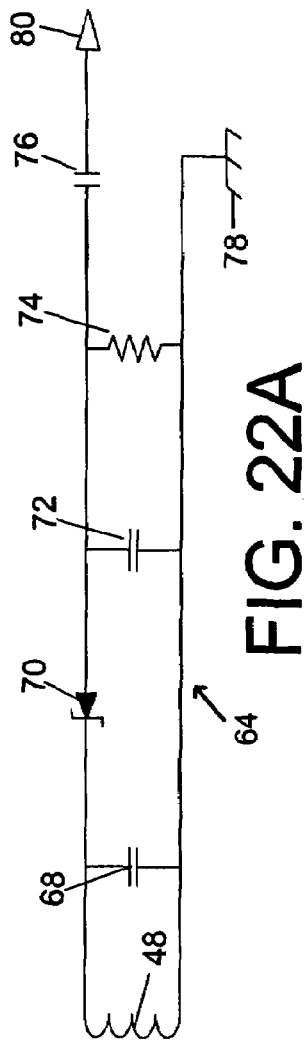
FIG. 22A is a schematic of an alternative embodiment of the implanted lead-receiver.
Figure 22B:
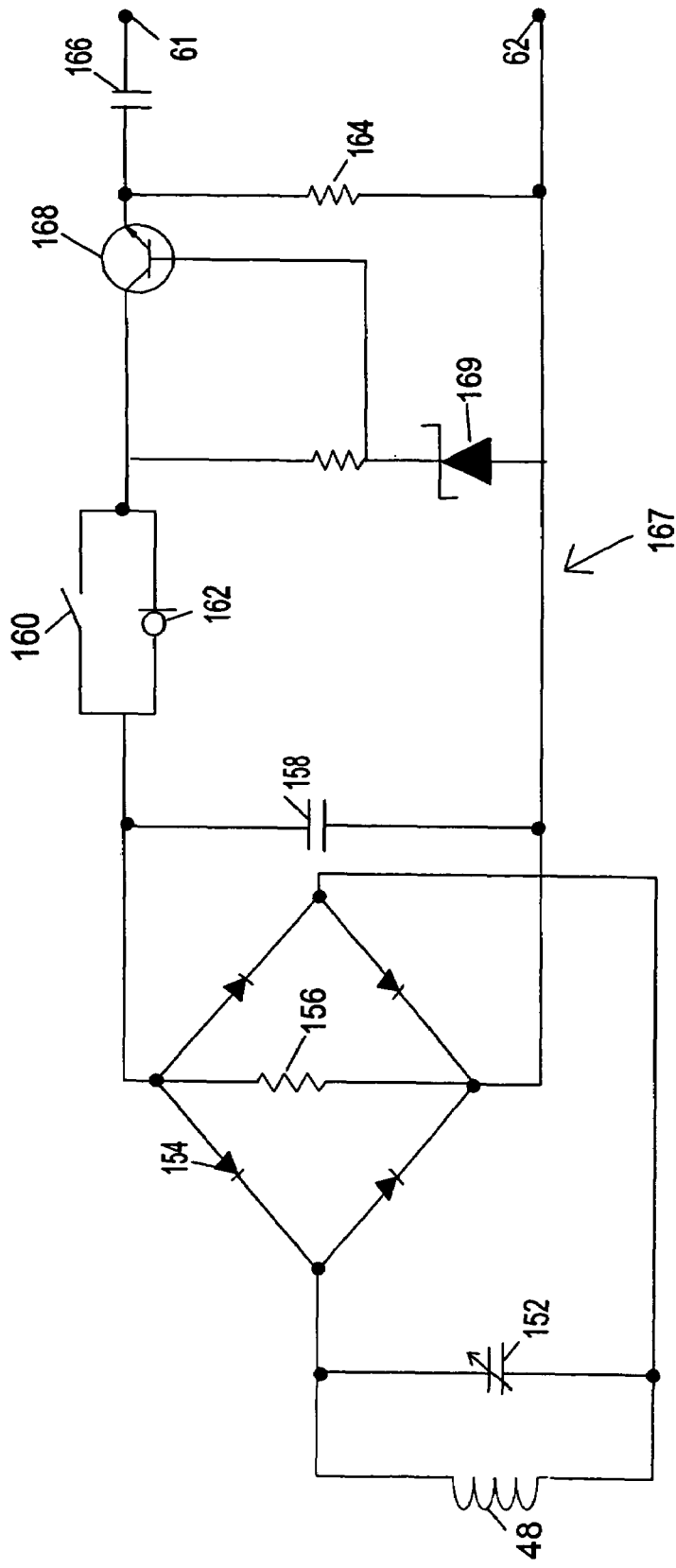
FIG. 22B is another alternative embodiment of the implanted lead-receiver.

The circuitry shown in FIGS. 22A and 22B can be used as an alternative, for the implanted stimulus-receiver. The circuitry of FIG. 22A is a slightly simpler version, and circuitry of FIG. 22B contains a conventional NPN transistor 168 connected in an emitter-follower configuration.

For therapy to commence, the primary (external) coil 46 is placed on the skin 60 on top of the surgically implanted (secondary) coil 48. An adhesive tape is then placed on the skin 60 and external coil 46 such that the external coil 46, is taped to the skin 60. For efficient energy transfer to occur, it is important that the primary (external) and secondary (internal) coils 46,48 be positioned along the same axis and be optimally positioned relative to each other. In this embodiment, the external coil 46 may be connected to proximity sensing circuitry 50. The correct positioning of the external coil 46 with respect to the internal coil 48 is indicated by turning "on" of a light emitting diode (LED) on the external stimulator 42.

Figure 23:
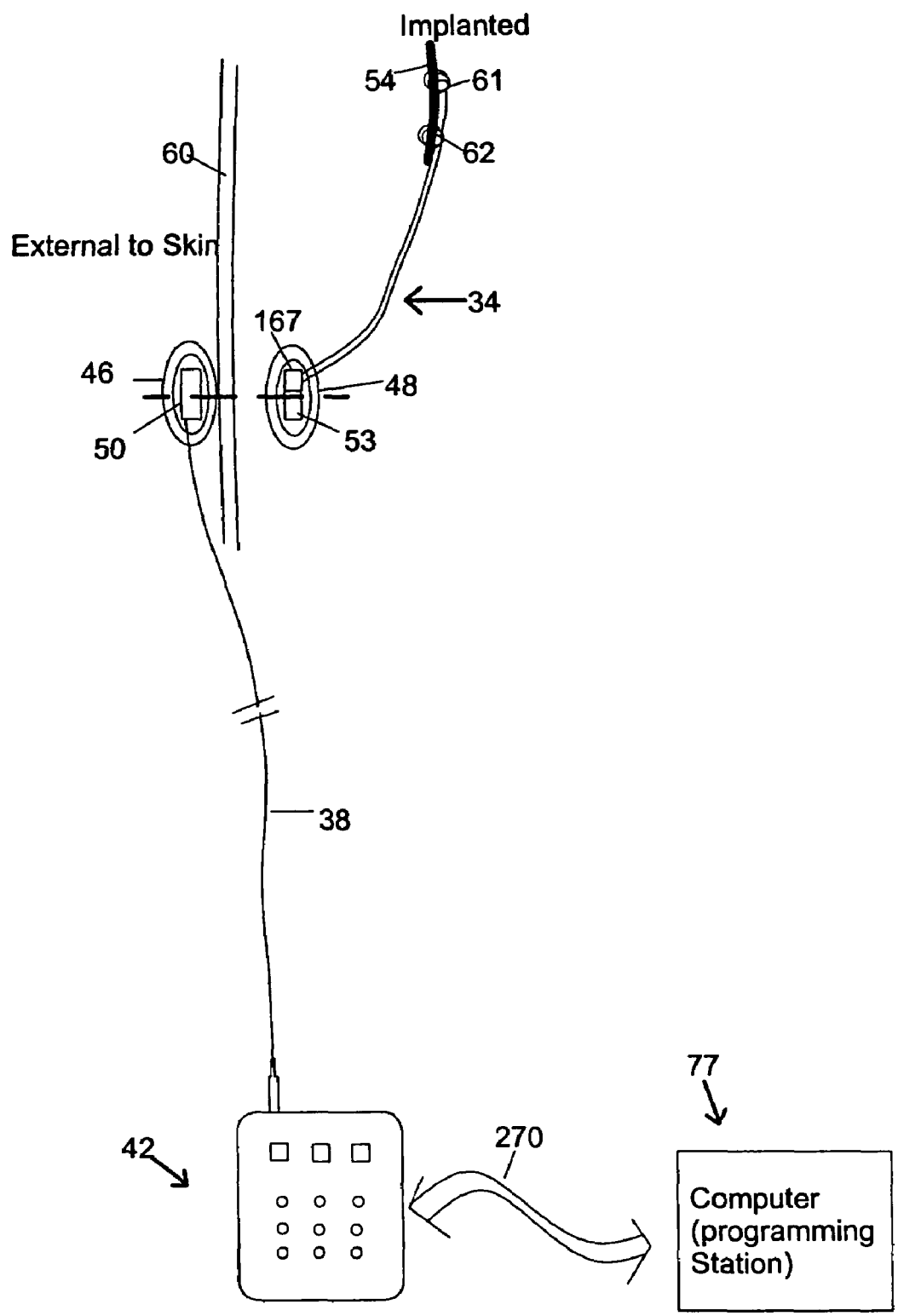
FIG. 23 shows coupling of the external stimulator and the implanted stimulus-receiver.

Optimal placement of the external (primary) coil 46 is done with the aid of proximity sensing circuitry incorporated in the system, in this embodiment. Proximity sensing occurs utilizing a combination of external and implantable components. The implanted components contains a relatively small magnet composed of materials that exhibit Giant Magneto-Resistor (GMR) characteristics such as Samarium-cobalt, a coil, and passive circuitry. Shown in conjunction with FIG. 23, the external coil 46 and proximity sensor circuitry 50 are rigidly connected in a convenient enclosure which is attached externally on the skin. The sensors measure the direction of the field applied from the magnet to sensors within a specific range of field strength magnitude. The dual sensors exhibit accurate sensing under relatively large separation between the sensor and the target magnet. As the external coil 46 placement is "fine tuned", the condition where the external (primary) coil 46 comes in optimal position, i.e. is located adjacent and parallel to the subcutaneous (secondary) coil 48, along its axis, is recorded and indicated by a light emitting diode (LED) on the external stimulator 42.

Figure 24:
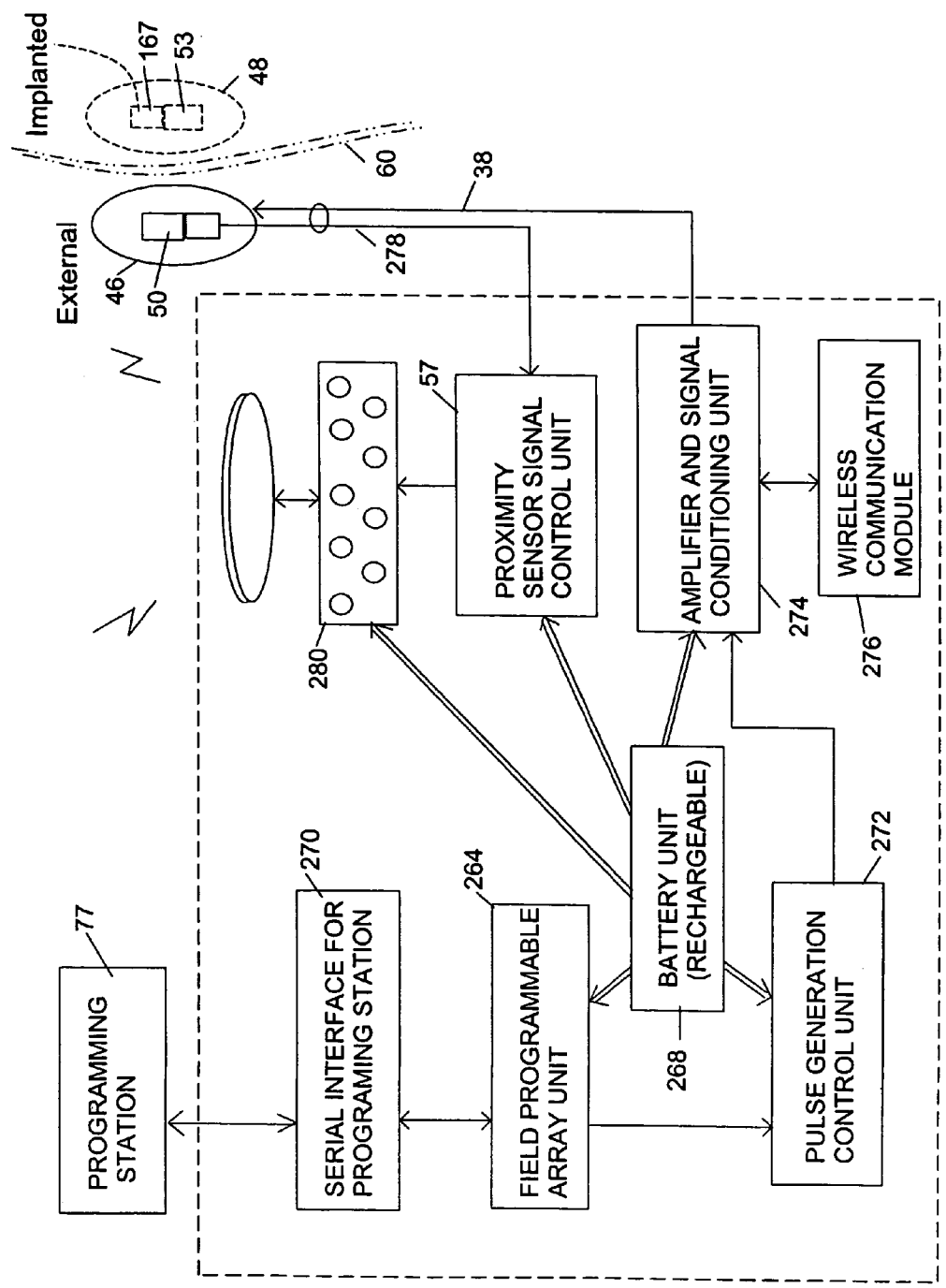
FIG. 24 is a top-level block diagram of the external stimulator and proximity sensing mechanism.

FIG. 24 shows an overall block diagram of the components of the external stimulator and the proximity sensing mechanism. The proximity sensing components are the primary (external) coil 46, supercutaneous (external) proximity sensors 648, 652 (FIG. 25) in the proximity sensor circuit unit 50, and a subcutaneous secondary coil 48 with a Giant Magneto Resister (GMR) magnet 53 associated with the proximity sensor unit. The proximity sensor circuit 50 provides a measure of the position of the secondary implanted coil 48. The signal output from proximity sensor circuit 50 is derived from the relative location of the primary and secondary coils 46, 48. The sub-assemblies consist of the coil and the associated electronic components, that are rigidly connected to the coil.

The proximity sensors (external) contained in the proximity sensor circuit 50 detect the presence of a GMR magnet 53, composed of Samarium Cobalt, that is rigidly attached to the implanted secondary coil 48. The proximity sensors, are mounted externally as a rigid assembly and sense the actual separation between the coils, also known as the proximity distance. In the event that the distance exceeds the system limit, the signal drops off and an alarm sounds to indicate failure of the production of adequate signal in the secondary implanted circuit 167, as applied in this embodiment of the device. This signal is provided to the location indicator LED 280.

Figure 25:
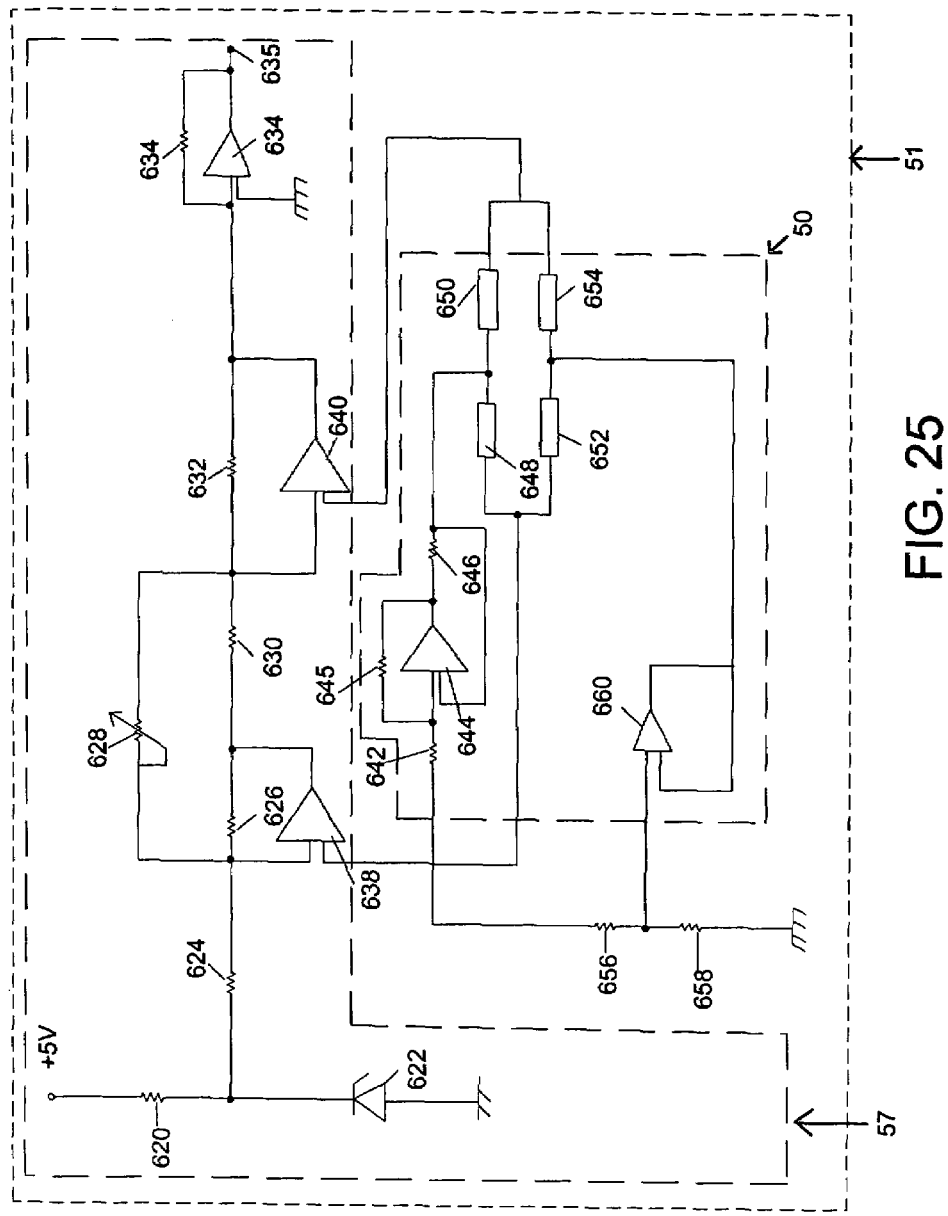
FIG. 25 is a diagram showing the proximity sensor circuitry.

FIG. 25 shows the circuit used to drive the proximity sensors 648, 652 of the proximity sensor circuit 50. The two proximity sensors 648, 652 obtain a proximity signal based on their position with respect to the implanted GMR magnet 53. This circuit also provides temperature compensation. The sensors 648, 652 are 'Giant Magneto Resistor' (GMR) type sensors packaged as proximity sensor unit 50. There are two components of the complete proximity sensor circuit. One component is mounted supercutaneously 50, and the other component, the proximity sensor signal control unit 57 is within the external stimulator 42. The resistance effect depends on the combination of the soft magnetic layer of magnet 53, where the change of direction of magnetization from external source can be large, and the hard magnetic layer, where the direction of magnetization remains unchanged. The resistance of this sensor 50 varies along a straight motion through the curvature of the magnetic field. A bridge differential voltage is suitably amplified and used as the proximity signal.

The Siemens GMR B6 (Siemens Corp., Special Components Inc., New Jersey) is used for this function in one embodiment. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 648, 652 are oriented orthogonal to each other.

The distance between the magnet 53 and sensor 50 is not relevant as long as the magnetic field is between 5 and 15 KA/m, and provides a range of distances between the sensors 648, 652 and the magnetic material 53. The GMR sensor registers the direction of the external magnetic field. A typical magnet to induce permanent magnetic field is approximately 15 by 8 by 5 $mm^3$, for this application and these components. The sensors 648, 652 are sensitive to temperature, such that the corresponding resistance drops as temperature increases. This effect is quite minimal until about 100° C. A full bridge circuit is used for temperature compensation, as shown in temperature compensation circuit 50 of FIG. 25. The sensors 648, 652 and a pair of resistors 650, 654 are shown as part of the bridge network for temperature compensation. It is also possible to use a full bridge network of two additional sensors in place of the resistors 650, 654.

The signal from either proximity sensor 648, 652 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees.

In the external stimulator 42 shown in FIG. 24, an indicator unit 280 which is provided to indicate proximity distance or coil proximity failure (for situations where the patch containing the external coil 46, has been removed, or is twisted abnormally etc.). Indication is also provided to assist in the placement of the patch. In case of general failure, a red light with audible signal is provided when the signal is not reaching the subcutaneous circuit. The indicator unit 280 also displays low battery status. The information on the low battery, normal and out of power conditions forewarns the user of the requirements of any corrective actions.

Also shown in FIG. 24, the programmable parameters are stored in a programmable logic 264. The predetermined programs stored in the external stimulator are capable of being modified through the use of a separate programming station 77. The Programmable Array Logic Unit 264 and interface unit 270 are interfaced to the programming station 77. The programming station 77 can be used to load new programs, change the existing predetermined programs or the program parameters for various stimulation programs. The programming station is connected to the programmable array unit 75 (comprising programmable array logic 304 and interface unit 270) with an RS232-C serial connection. The main purpose of the serial line interface is to provide an RS232-C standard interface. Other suitable connectors such as a USB connector or other connectors with standard protocols may also be used.

This method enables any portable computer with a serial interface to communicate and program the parameters for storing the various programs. The serial communication interface receives the serial data, buffers this data and converts it to a 16 bit parallel data. The programmable array logic 264 component of programmable array unit receives the parallel data bus and stores or modifies the data into a random access matrix. This array of data also contains special logic and instructions along with the actual data. These special instructions also provide an algorithm for storing, updating and retrieving the parameters from long-term memory. The programmable logic array unit 264, interfaces with long term memory to store the predetermined programs. All the previously modified programs can be stored here for access at any time, as well as, additional programs can be locked out for the patient. The programs consist of specific parameters and each unique program will be stored sequentially in long-term memory. A battery unit is present to provide power to all the components. The logic for the storage and decoding is stored in a random addressable storage matrix (RASM).

Conventional microprocessor and integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver the pre-determined programs is well known to those skilled in the art.

Figure 26:
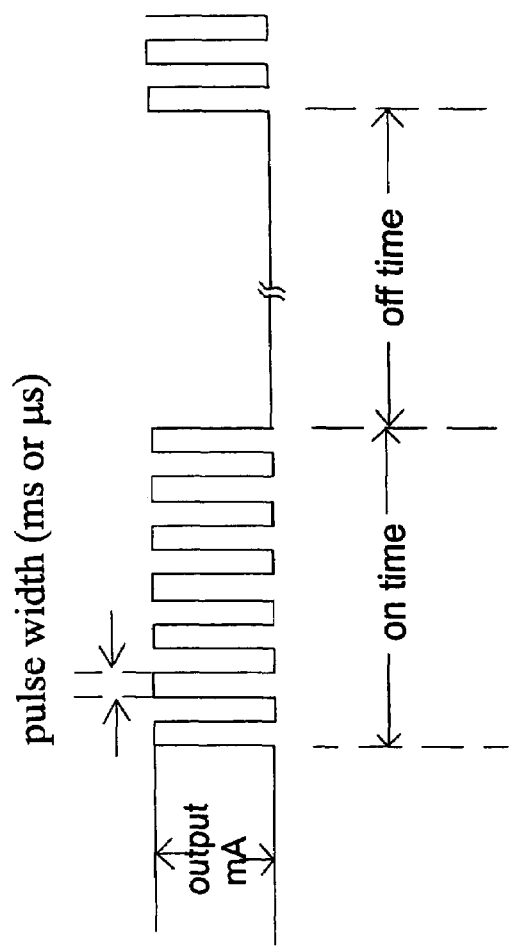
FIG. 26A shows the pulse train to be transmitted to the vagus nerve.
FIG. 26B shows the ramp-up and ramp-down characteristic of the pulse train.
Figure 26:
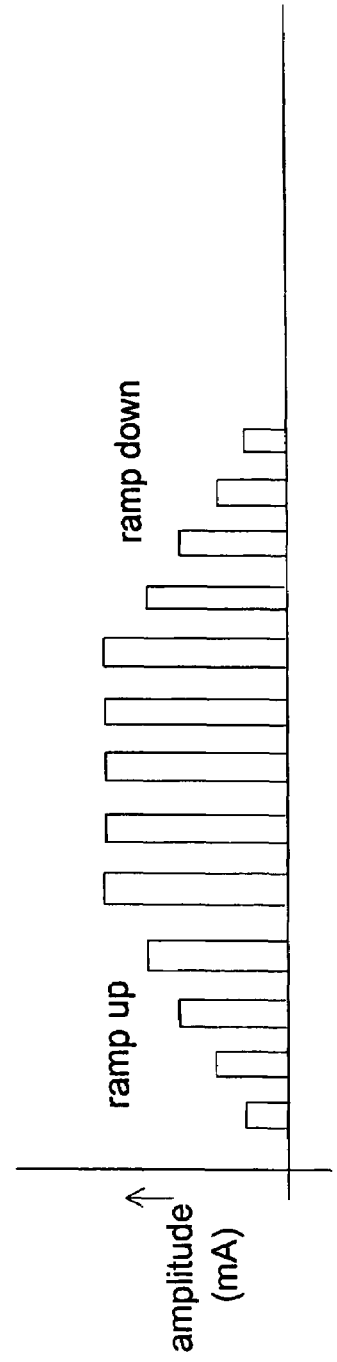

The pulses delivered to the nerve tissue for stimulation therapy are shown graphically in FIG. 26A. As shown in FIG. 26B, for patient comfort when the electrical stimulation is turned on, the electrical stimulation is ramped up and ramped down, instead of abrupt delivery of electrical pulses.

The selective stimulation to the vagus nerve can be performed in one of two ways. One method is to activate one of several "pre-determined" programs. A second method is to "custom" program the electrical parameters which can be selectively programmed, for specific therapy to the individual patient. The electrical parameters which can be individually programmed, include variables such as pulse amplitude, pulse width, frequency of stimulation, stimulation on-time, and stimulation off-time. Table three below defines the approximate range of parameters,

TABLE 3

Electrical parameter range delivered to the nerve

| PARAMER | RANGE |
| --- | --- |
| Pulse Amplitude | 0.1 Volt-15 Volts |
| Pulse width | 20 µS-5 mSec. |
| Stim. Frequency | 5 Hz-200 Hz |
| Freq. for blocking | DC to 750 Hz |
| On-time | 5 Secs-24 hours |
| Off-time | 5 Secs-24 hours |

The parameters in Table 3 are the electrical signals delivered to the nerve via the two electrodes 61,62 (distal and proximal) around the nerve, as shown in FIG. 20. It being understood that the signals generated by the external pulse generator 42 and transmitted via the primary coil 46 are larger, because the attenuation factor between the primary coil and secondary coil is approximately 10-20 times, depending upon the distance, and orientation between the two coils. Accordingly, the range of transmitted signals of the external pulse generator are approximately 10-20 times larger than shown in Table 2.

Figure 27:
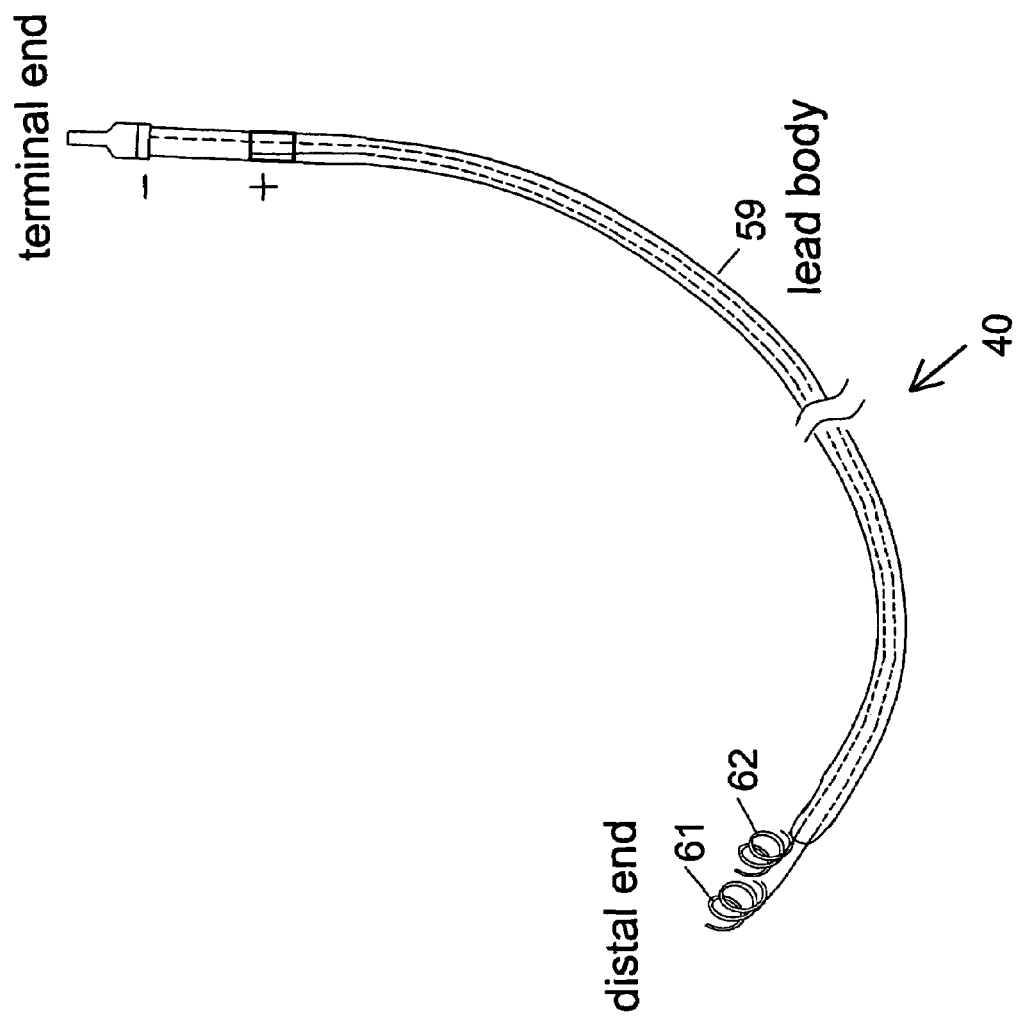
FIG. 27 is a schematic diagram of the implantable lead.

Referring now to FIG. 27, the implanted lead 40 component of the system is similar to cardiac pacemaker leads, except for distal portion (or electrode end) of the lead. The lead terminal preferably is linear bipolar, even though it can be bifurcated, and plug(s) into the cavity of the pulse generator means The lead body 59 insulation may be constructed of medical grade silicone, silicone reinforced with polytetrafluoro-ethylene (PTFE), or polyurethane. The electrodes 61,62 for stimulating the vagus nerve 54 may either wrap around the nerve once or may be spiral shaped. These stimulating electrodes may be made of pure platinum, platinum/Iridium alloy or platinum/iridium coated with titanium nitride. The conductor connecting the terminal to the electrodes 61,62 is made of an alloy of nickel-cobalt. The implanted lead design variables are also summarized in table four below.

TABLE 4

Lead design variables

| Proximal End Lead Terminal | Lead body-Insulation Materials | Lead-Coating | Conductor (connecting proximal and distal ends) | Electrode - Material | Distal End Electrode - Type |
| --- | --- | --- | --- | --- | --- |
| Linear bipolar | Polyurethane | Antimicrobial coating | Alloy of Nickel-Cobalt | Pure Platinum | Spiral electrode |
| Bifurcated | Silicone | Anti-Inflammatory coating | | Platinum-Iridium (Pt/Ir) Alloy | Wrap-around electrode |
| | Silicone with Polytetrafluoroethylene (PTFE) | Lubricious coating | | Pt/Ir coated with Titanium Nitride | Steroid eluting |

TABLE 4-continued

Lead design variables

| Proximal End Lead Terminal | Lead body-Insulation Materials | Lead-Coating | Conductor (connecting proximal and distal ends) | Electrode - Material | Distal End Electrode - Type |
|---|---|---|---|---|---|
| | | | | Carbon | Hydrogel electrodes Cuff electrodes |

Examples of electrode designs are also shown in U.S. Pat. No. 5,215,089 (Baker), U.S. Pat. No. 5,351,394 (Weinburg), and U.S. Pat. No. 6,600,956 (Mashino), which are incorporated herein by reference.

Once the lead is fabricated, coating such as anti-microbial, anti-inflammatory, or lubricious coating may be applied to the body of the lead.

Figure 28A:
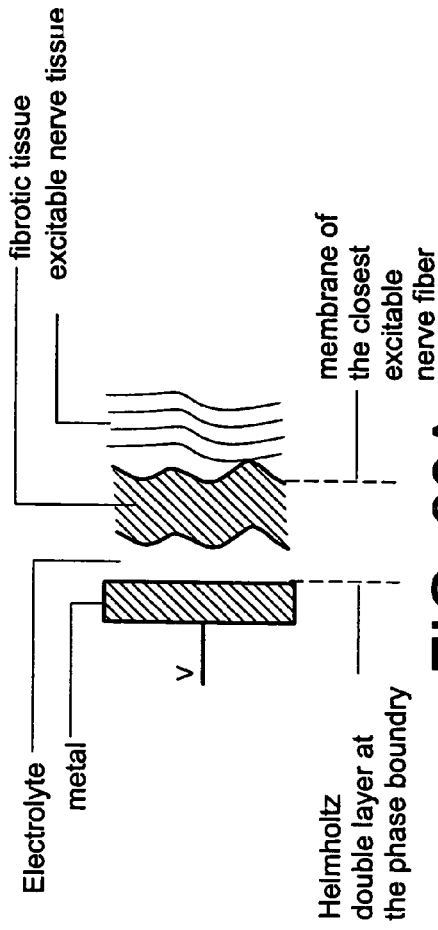
FIG. 28A is diagram depicting stimulating electrode-tissue interface.
Figure 28B:
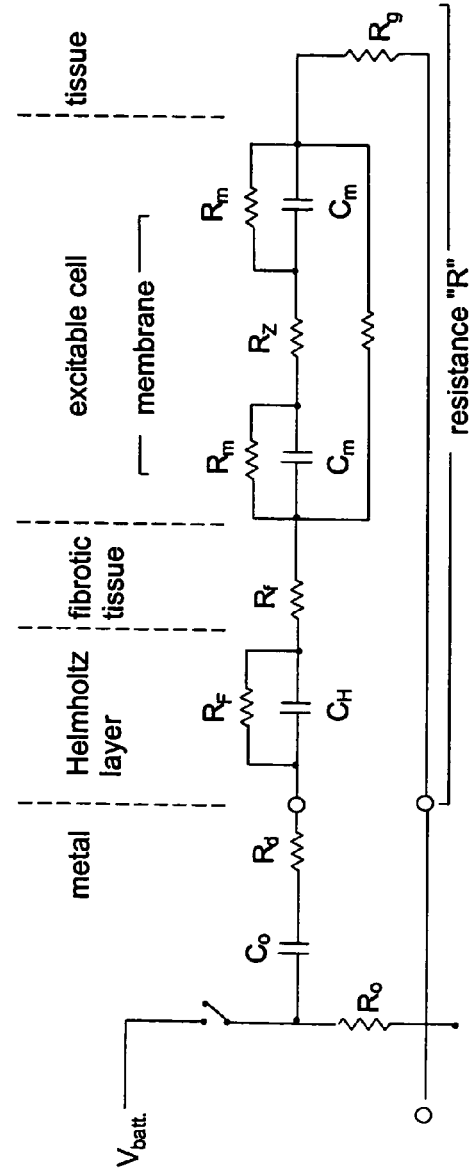
FIG. 28B is diagram depicting an electrical model of the electrode-tissue interface.

FIG. 28A summarizes electrode-tissue interface between the nerve tissue and electrodes 61, 62. There is a thin layer of fibrotic tissue between the stimulating electrode 61 and the excitable nerve fibers of the vagus nerve 54. FIG. 28B summarizes the most important properties of the metal/tissue phase boundary in an equivalent circuit diagram. Both the membrane of the nerve fibers and the electrode surface are represented by parallel capacitance and resistance. Application of a constant battery voltage Vbat from the pulse generator, produces voltage changes and current flow, the time course of which is crucially determined by the capacitive components in the equivalent circuit diagram. During the pulse, the capacitors Co, Ch and Cm are charged through the ohmic resistances, and when the voltage Vbat is turned off, the capacitors discharge with current flow on the opposite direction.

Figure 29:
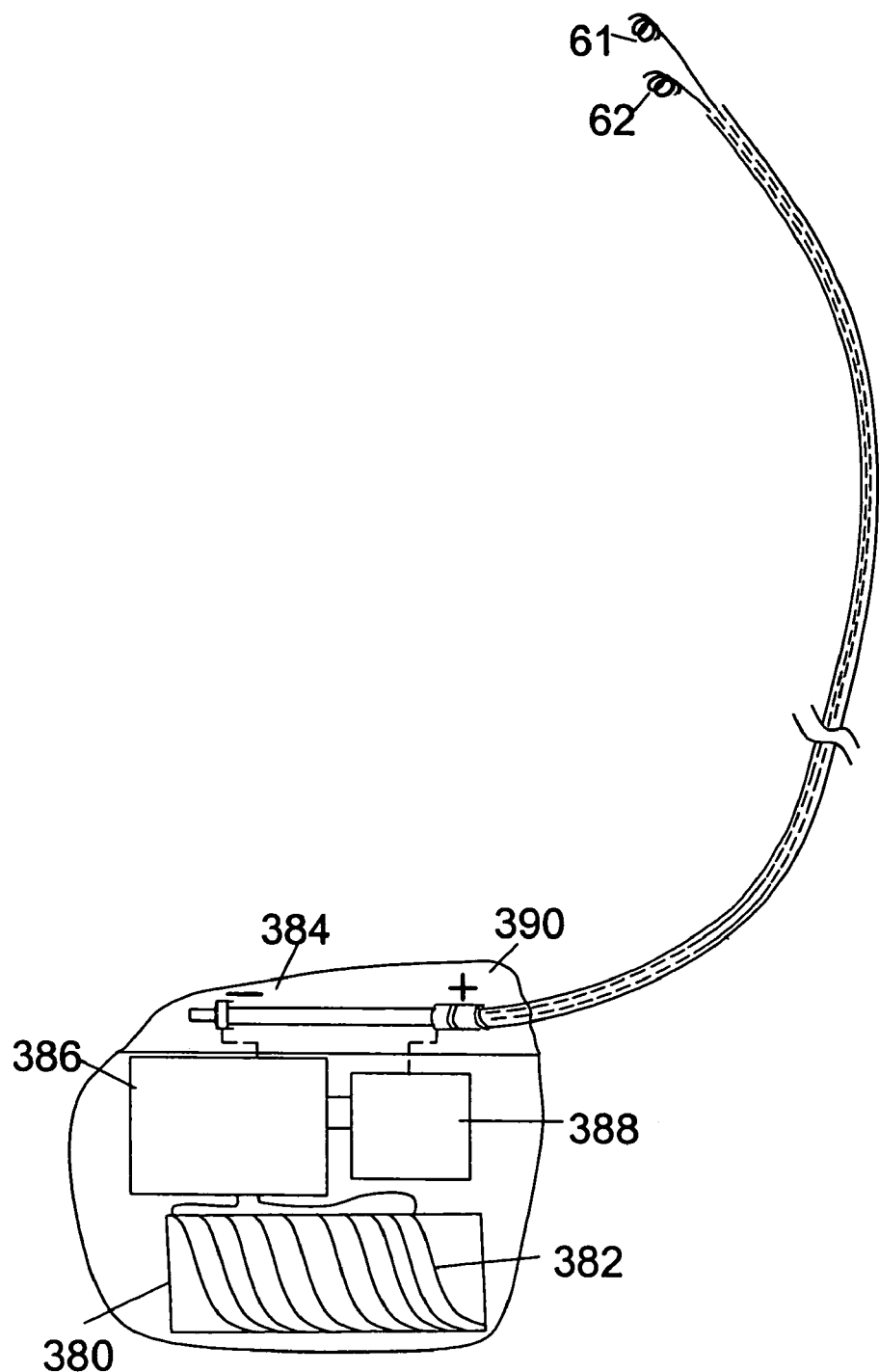
FIG. 29 is a schematic diagram showing the implantable lead and one form of stimulus-receiver.

Implanted Stimulus-Receiver Comprising a High Value Capacitor for Storing Charge, used in Conjunction with an External Stimulator In one embodiment, the implanted stimulus-receiver may be a system which is RF coupled combined with a power source. In this embodiment, the implanted stimulus-receiver contains high value, small sized capacitor(s) for storing charge and delivering electric stimulation pulses for up to several hours by itself, once the capacitors are charged. The packaging is shown in FIG. 29. Using mostly hybrid components and appropriate packaging, the implanted portion of the system described below is conducive to miniaturization. As shown in FIG. 29, a solenoid coil 382 wrapped around a ferrite core 380 is used as the secondary of an air-gap transformer for receiving power and data to the implanted device. The primary coil is external to the body. Since the coupling between the external transmitter coil and receiver coil 382 may be weak, a high-efficiency transmitter/amplifier is used in order to supply enough power to the receiver coil 382. Class-D or Class-E power amplifiers may be used for this purpose. The coil for the external transmitter (primary coil) may be placed in the pocket of a customized garment.

Figure 30:
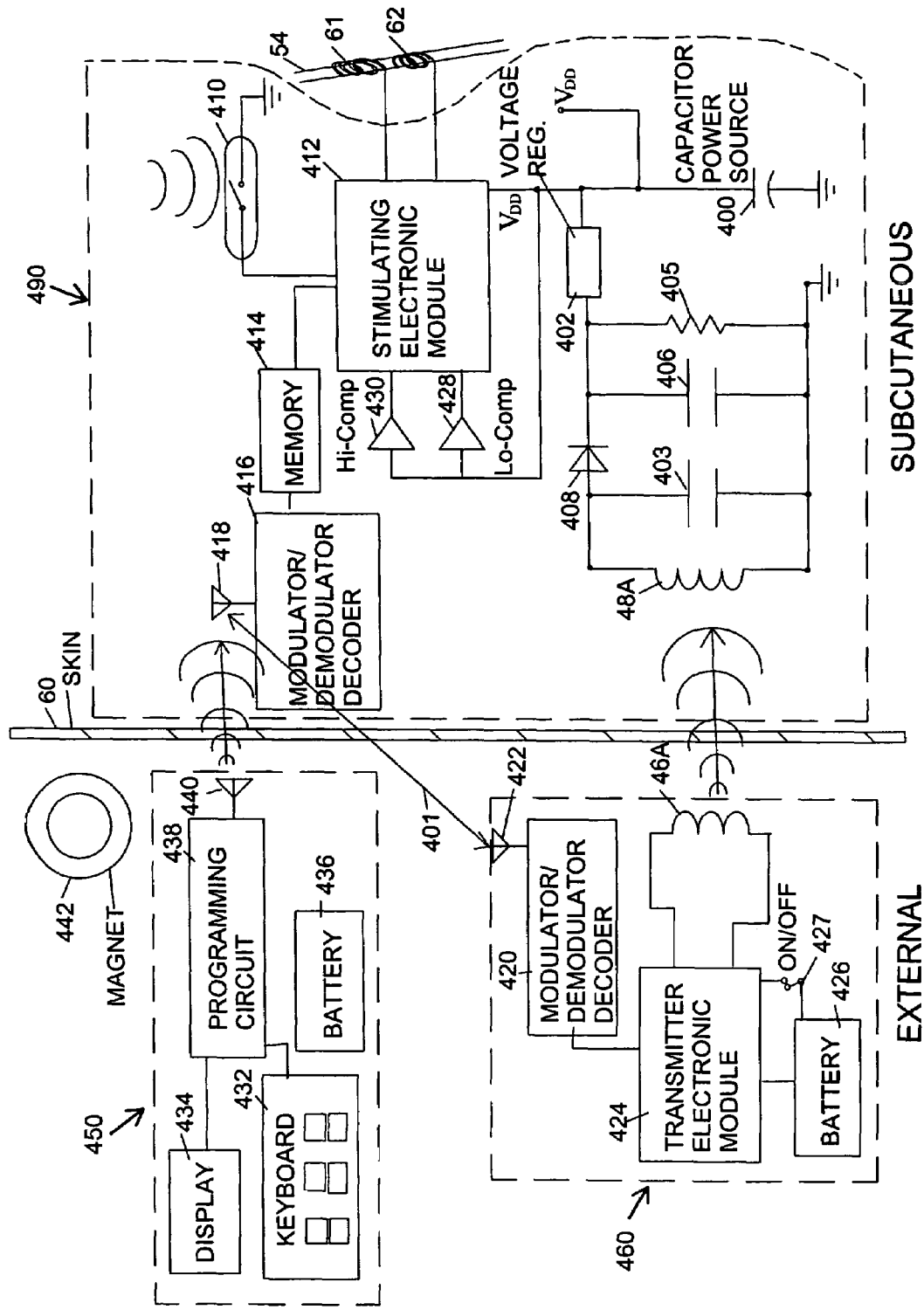
FIG. 30 is a schematic block diagram showing a system for neuromodulation of the vagus nerve, with an implanted component which is both RF coupled and contains a capacitor power source.

As shown in conjunction with FIG. 30 of the implanted stimulus-receiver 490 and the system, the receiving inductor 48A and tuning capacitor 403 are tuned to the frequency of the transmitter. The diode 408 rectifies the AC signals, and a small sized capacitor 406 is utilized for smoothing the input voltage $V_I$ fed into the voltage regulator 402. The output voltage $V_D$ of regulator 402 is applied to capacitive energy power supply and source 400 which establishes source power $V_{DD}$. Capacitor 400 is a big value, small sized capacative energy source which is classified as low internal impedance, low power loss and high charge rate capacitor, such as Panasonic Model No. 641.

The refresh-recharge transmitter unit 460 includes a primary battery 426, an ON/Off switch 427, a transmitter electronic module 442, an RF inductor power coil 46A, a modulator/demodulator 420 and an antenna 422.

When the ON/OFF switch is on, the primary coil 46A is placed in close proximity to skin 60 and secondary coil 48A of the implanted stimulator 490. The inductor coil 46A emits RF waves establishing EMF wave fronts which are received by secondary inductor 48A. Further, transmitter electronic module 442 sends out command signals which are converted by modulator/demodulator decoder 420 and sent via antenna 422 to antenna 418 in the implanted stimulator 490. These received command signals are demodulated by decoder 416 and replied and responded to, based on a program in memory 414 (matched against a "command table" in the memory). Memory 414 then activates the proper controls and the inductor receiver coil 48A accepts the RF coupled power from inductor 46A.

The RF coupled power, which is alternating or AC in nature, is converted by the rectifier 408 into a high DC voltage. Small value capacitor 406 operates to filter and level this high DC voltage at a certain level. Voltage regulator 402 converts the high DC voltage to a lower precise DC voltage while capacitive power source 400 refreshes and replenishes.

When the voltage in capacative source 400 reaches a predetermined level (that is $V_{DD}$ reaches a certain predetermined high level), the high threshold comparator 430 fires and stimulating electronic module 412 sends an appropriate command signal to modulator/decoder 416. Modulator/decoder 416 then sends an appropriate "fully charged" signal indicating that capacitive power source 400 is fully charged, is received by antenna 422 in the refresh-recharge transmitter unit 460.

In one mode of operation, the patient may start or stop stimulation by waving the magnet 442 once near the implant. The magnet emits a magnetic force $L_m$ which pulls reed switch 410 closed. Upon closure of reed switch 410, stimulating electronic module 412 in conjunction with memory 414 begins the delivery (or cessation as the case may be) of controlled electronic stimulation pulses to the vagus nerve 54 via electrodes 61, 62. In another mode (AUTO), the stimulation is automatically delivered to the implanted lead based upon programmed ON/OFF times.

The programmer unit 450 includes keyboard 432, programming circuit 438, rechargeable battery 436, and display 434. The physician or medical technician programs programming unit 450 via keyboard 432. This program regarding the frequency, pulse width, modulation program, ON time etc. is stored in programming circuit 438. The programming unit 450 must be placed relatively close to the implanted stimulator 490 in order to transfer the commands and programming information from antenna 440 to antenna 418. Upon receipt of this programming data, modulator/demodulator and decoder 416 decodes and conditions these signals, and the digital programming information is captured by memory 414. This digital programming information is further processed by stimulating electronic module 412. In the DEMAND operating mode, after programming the implanted stimulator, the patient turns ON and OFF the implanted stimulator via hand held magnet 442 and the reed switch 410. In the automatic mode (AUTO), the implanted stimulator turns ON and OFF automatically according to the programmed values for the ON and OFF times.

Other simplified versions of such a system may also be used. For example, a system such as this, where a separate programmer is eliminated, and simplified programming is performed with a magnet and reed switch, can also be used.

Programmer-Less Implantable Pulse Generator
(IPG)

In one embodiment, a programmer-less implantable pulse generator (IPG) may be used. In this embodiment, shown in conjunction with FIG. 31, the implantable pulse generator 171 is provided with a reed switch 92 and memory circuitry 102. The reed switch 92 being remotely actuable by means of a magnet 90 brought into proximity of the pulse generator 171, in accordance with common practice in the art. In this embodiment, the reed switch 92 is coupled to a multi-state converter/timer circuit 96, such that a single short closure of the reed switch can be used as a means for non-invasive encoding and programming of the pulse generator 171 parameters.

Figure 32:
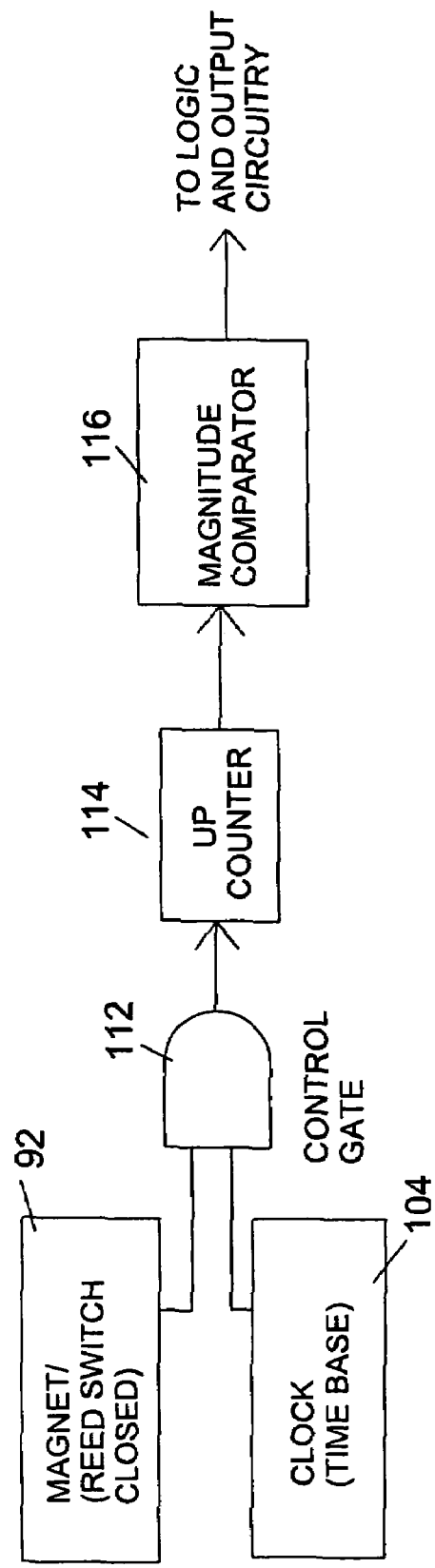
FIG. 32 is a schematic diagram showing implementation of a multi-state converter.

In one embodiment, shown in conjunction with FIG. 32, the closing of the reed switch 92 triggers a counter. The magnet 90 and timer are ANDed together. The system is configured such that during the time that the magnet 82 is held over the pulse generator 171, the output level goes from LOW stimulation state to the next higher stimulation state every 5 seconds. Once the magnet 82 is removed, regardless of the state of stimulation, an application of the magnet, without holding it over the pulse generator 171, triggers the OFF state, which also resets the counter.

Figure 31:
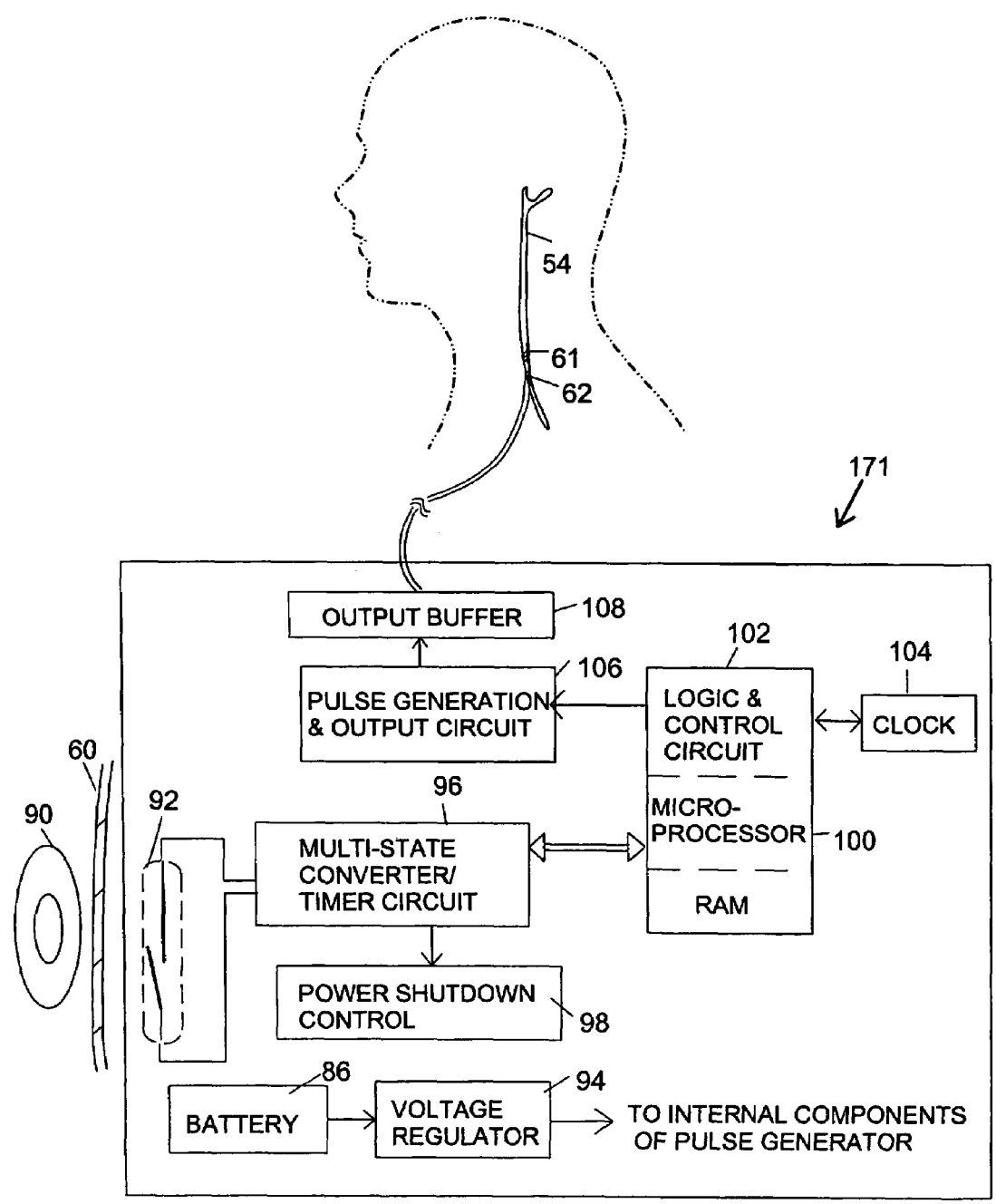
FIG. 31 is a simplified block diagram showing control of the implantable neurostimulator with a magnet.

Once the prepackaged/predetermined logic state is activated by the logic and control circuit 102, as shown in FIG. 31, the pulse generation and amplification circuit 106 deliver the appropriate electrical pulses to the vagus nerve 54 of the patient via an output buffer 108. The delivery of output pulses is configured such that the distal electrode 61 (electrode closer to the brain) is the cathode and the proximal electrode 62 is the anode. Timing signals for the logic and control circuit 102 of the pulse generator 171 are provided by a crystal oscillator 104. The battery 86 of the pulse generator 171 has terminals connected to the input of a voltage regulator 94. The regulator 94 smoothes the battery output and supplies power to the internal components of the pulse generator 171. A microprocessor 100 controls the program parameters of the device, such as the voltage, pulse width, frequency of pulses, on-time and off-time. The microprocessor may be a commercially available, general purpose microprocessor or microcontroller, or may be a custom integrated circuit device augmented by standard RAM/ROM components.

In one embodiment, there are four stimulation states. A larger (or lower) number of states can be achieved using the same methodology, and such is considered within the scope of the invention. These four states are, LOW stimulation state, LOW-MED stimulation state, MED stimulation state, and HIGH stimulation state. Examples of stimulation parameters (delivered to the vagus nerve) for each state are as follows, LOW stimulation state example is,
Current output: 0.75 milliAmps.
Pulse width: 0.20 msec.
Pulse frequency: 20 Hz
Cycles: 20 sec. on-time and 2.0 min. off-time in repeating cycles.
LOW-MED stimulation state example is,
Current output: 1.5 milliAmps,
Pulse width: 0.30 msec.
Pulse frequency: 25 Hz
Cycles: 1.5 min. on-time and 20.0 min. off-time in repeating cycles.
MED stimulation state example is,
Current output: 2.0 milliAmps.
Pulse width: 0.30 msec.
Pulse frequency: 30 Hz
Cycles: 1.5 min. on-time and 20.0 min. off-time in repeating cycles.
HIGH stimulation state example is,
Current output: 3.0 milliAmps,
Pulse width: 0.40 msec.
Pulse frequency: 30 Hz
Cycles: 2.0 min. on-time and 20.0 min. off-time in repeating cycles.

These prepackaged/predetermined programs are merely examples, and the actual stimulation parameters will deviate from these depending on the treatment application.

It will be readily apparent to one skilled in the art, that other schemes can be used for the same purpose. For example, instead of placing the magnet 90 on the pulse generator 171 for a prolonged period of time, different stimulation states can be encoded by the sequence of magnet applications. Accordingly, in an alternative embodiment there can be three logic states, OFF, LOW stimulation (LS) state, and HIGH stimulation (HS) state. Each logic state again corresponds to a prepackaged/predetermined program such as presented above. In such an embodiment, the system could be configured such that one application of the magnet triggers the generator into LS State. If the generator is already in the LS state then one application triggers the device into OFF State. Two successive magnet applications triggers the generator into MED stimulation state, and three successive magnet applications triggers the pulse generator in the HIGH Stimulation State. Subsequently, one application of the magnet while the device is in any stimulation state, triggers the device OFF.

Figure 33:
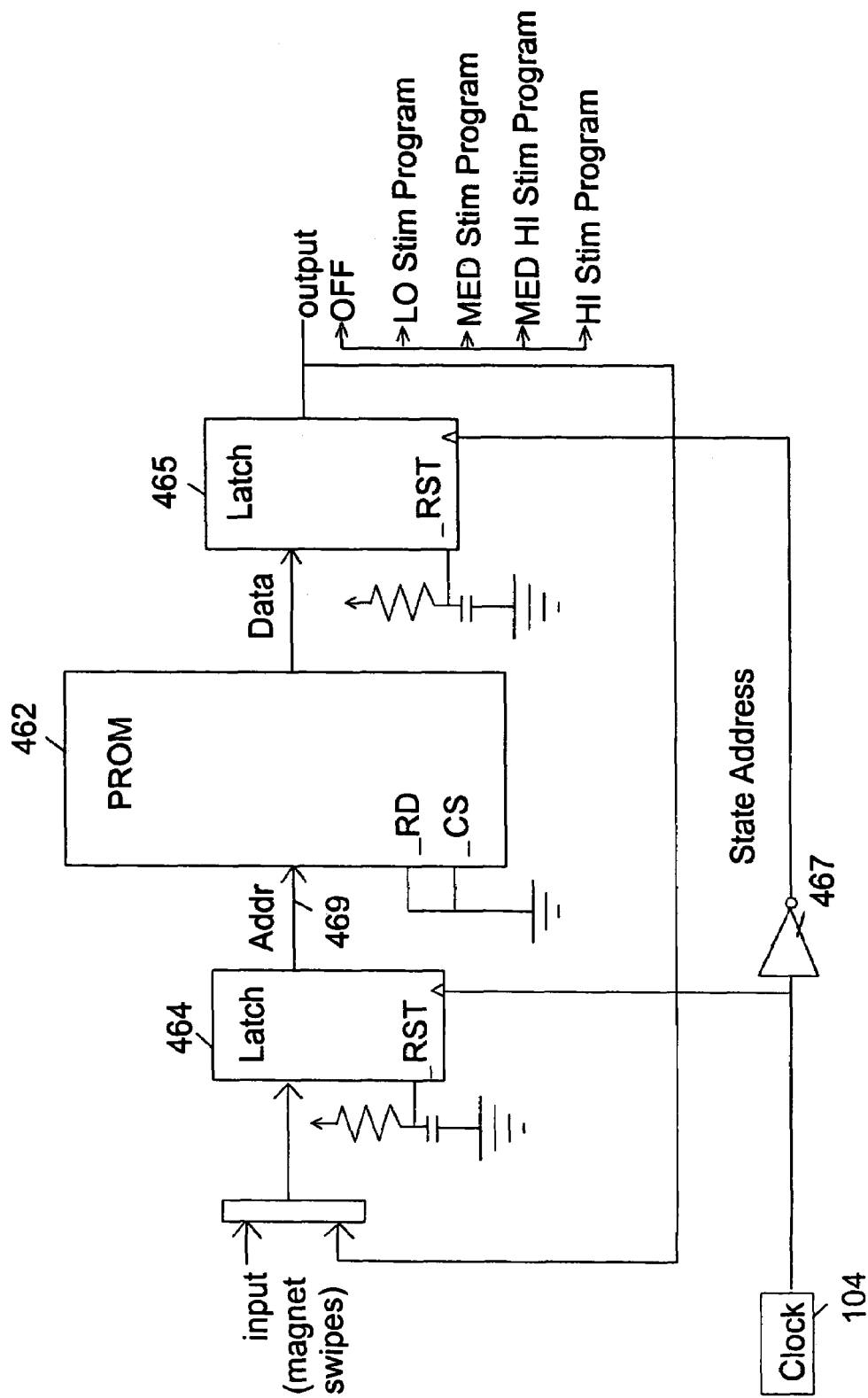
FIG. 33 is a schematic diagram depicting digital circuitry for state machine.

FIG. 33 shows a representative digital circuitry used for the basic state machine circuit. The circuit consists of a PROM 462 that has part of its data fed back as a state address. Other address lines 469 are used as circuit inputs, and the state machine changes its state address on the basis of these inputs. The clock 104 is used to pass the new address to the PROM 462 and then pass the output from the PROM 462 to the outputs and input state circuits. The two latches 464, 465 are operated 180° out of phase to prevent glitches from unexpectedly affecting any output circuits when the ROM changes state. Each state responds differently according to the inputs it receives.

The advantage of this embodiment is that it is cheaper to manufacture than a fully programmable implantable pulse generator (IPG).

Microstimulator

Figure 34A:
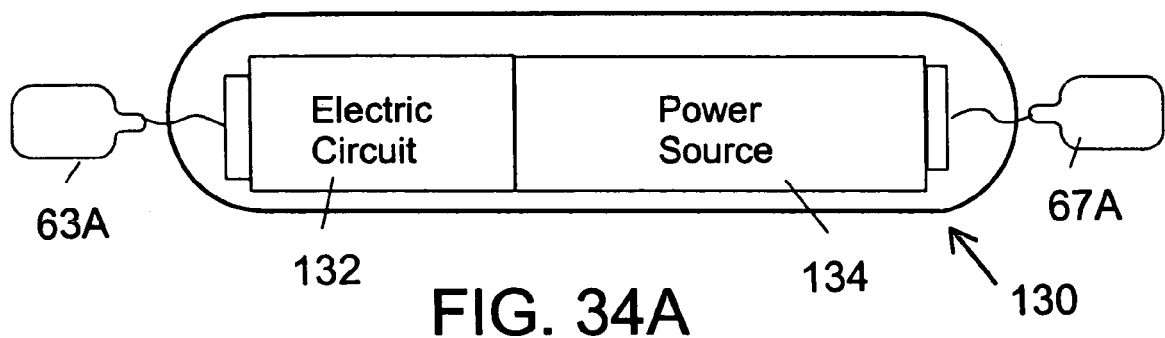
FIGS. 34A-C depicts various forms of implantable microstimulators.
Figure 34B:
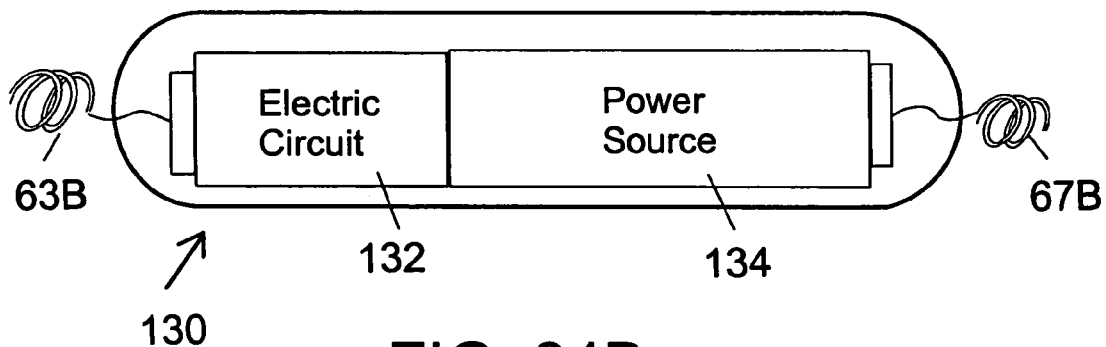
Figure 34C:
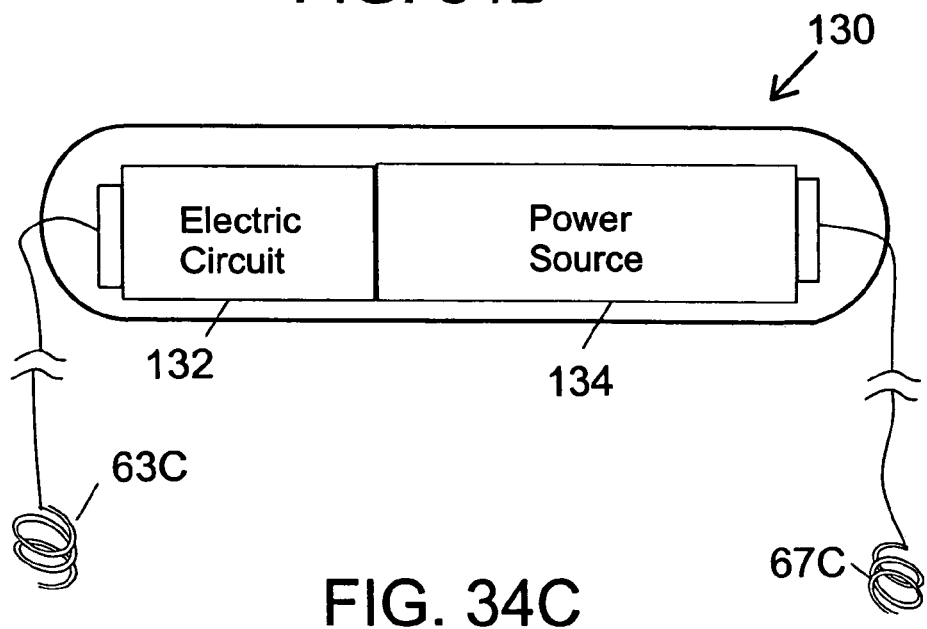
Figure 35:
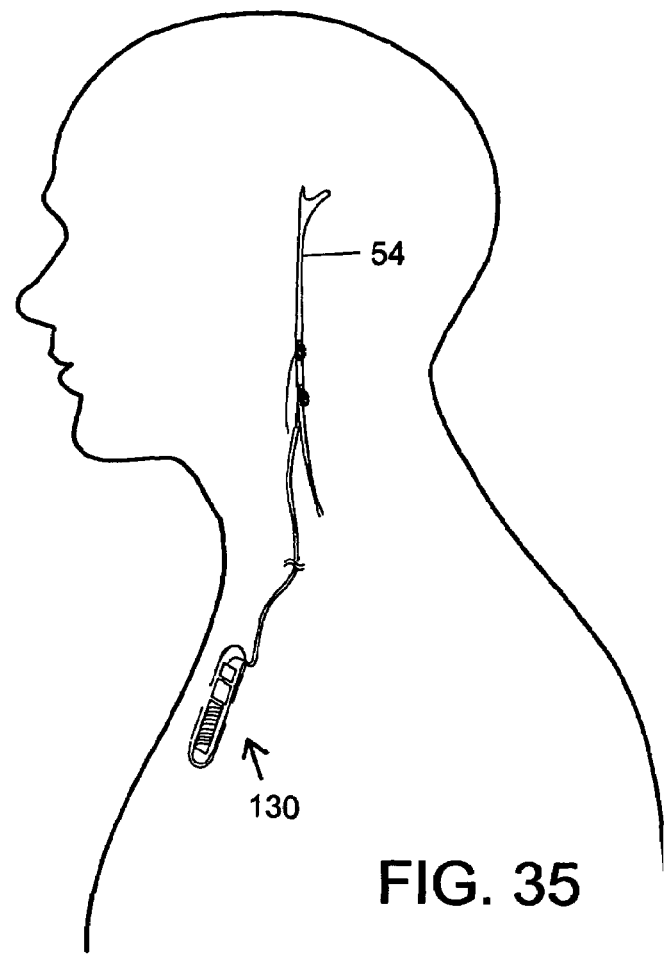
FIG. 35 is a figure depicting an implanted microstimulator for providing pulses to vagus nerve.

In one embodiment, a microstimulator 130 may be used for providing pulses to the vagus nerve(s) 54. Shown in conjunction with FIG. 34A, is a microstimulator where the electrical circuitry 132 and power source 134 are encased in a miniature hermetically sealed enclosure, and only the electrodes 63A, 67A are exposed. FIG. 34B depicts the same microstimulator, except the electrodes are modified and adapted to wrap around the nerve tissue 54. Because of its small size, the whole microstimulator may be in the proximity of the nerve tissue to be stimulated, or alternatively as shown in conjunction with FIG. 35, the microstimulator may be implanted at a different site, and connected to the electrodes via conductors insulated with silicone and polyurethane (FIG. 34C).

Figure 36:
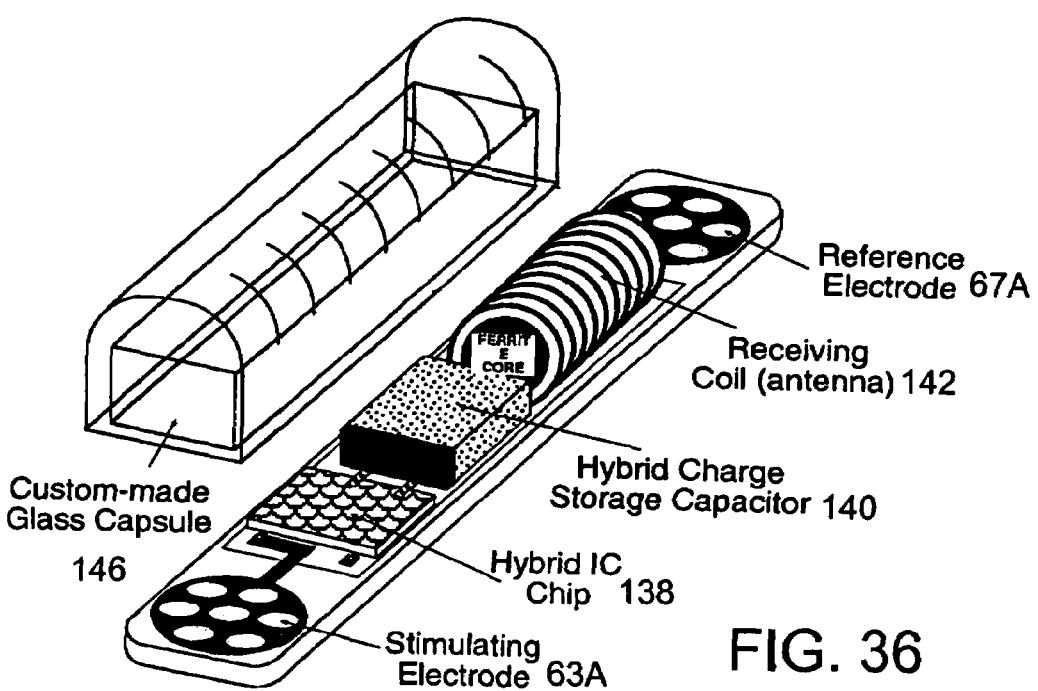
FIG. 36 is a diagram depicting the components and assembly of a microstimulator.

Shown in reference with FIG. 36 is the overall structure of an implantable microstimulator 130. It consists of a micromachined silicon substrate that incorporates two stimulating electrodes which are the cathode and anode of a bipolar stimulating electrode pair 63A, 67A; a hybrid-connected tantalum chip capacitor 140 for power storage; a receiving coil 142; a bipolar-CMOS integrated circuit chip 138 for power regulation and control of the microstimulator; and a custom made glass capsule 146 that is electrostatically bonded to the silicon carrier to provide a hermetic package for the receiver-stimulator circuitry and hybrid elements. The stimulating electrode pair 63,64 resides outside of the package and feedthroughs are used to connect the internal electronics to the electrodes.

Figure 37:
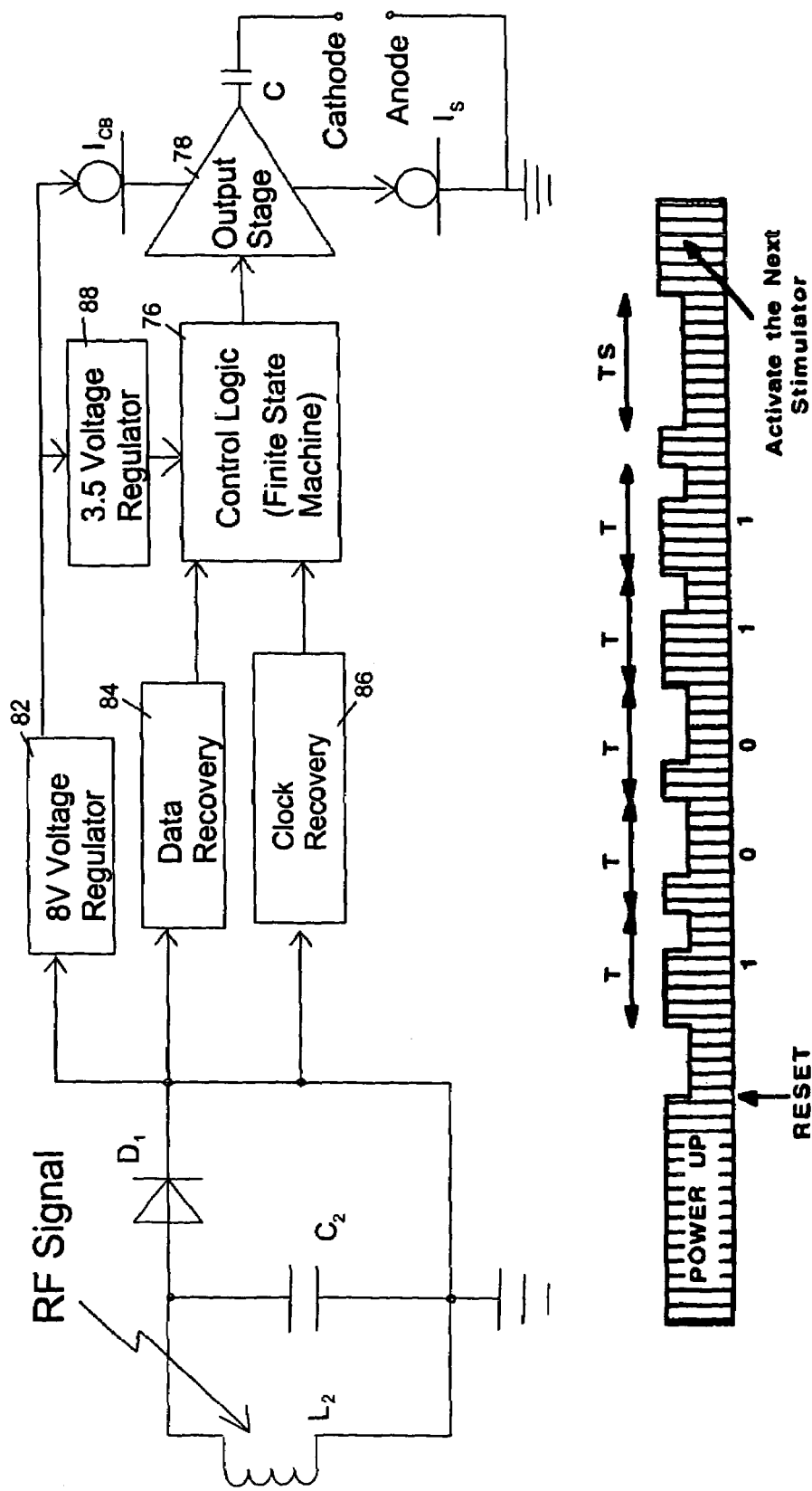
FIG. 37 shows functional block diagram of the circuitry for a microstimulator.

FIG. 37 shows the overall system electronics required for the microstimulator, and the power and data transmission protocol used for radiofrequency telemetry. The circuit receives an amplitude modulated RF carrier from an external transmitter and generates 8-V and 4-V dc supplies, generates a clock from the carrier signal, decodes the modulated control data, interprets the control data, and generates a constant current output pulse when appropriate. The RF carrier used for the telemetry link has a nominal frequency of around 1.8 MHz, and is amplitude modulated to encode control data. Logical "1" and "0" are encoded by varying the width of the amplitude modulated carrier, as shown in the bottom portion of FIG. 37. The carrier signal is initially high when the transmitter is turned on and sets up an electromagnetic field inside the transmitter coil. The energy in the field is picked up by receiver coils 142, and is used to charge the hybrid capacitor 140. The carrier signal is turned high and then back down again, and is maintained at the low level for a period between 1-200 µsec. The microstimulator 130 will then deliver a constant current pulse into the nerve tissue through the stimulating electrode pair 63A, 67A for the period that the carrier is low. Finally, the carrier is turned back high again, which will indicate the end of the stimulation period to the microstimulator 130, thus allowing it to charge its capacitor 140 back up to the on-chip voltage supply.

On-chip circuitry has been designed to generate two regulated power supply voltages (4V and 8V) from the RF carrier, to demodulate the RF carrier in order to recover the control data that is used to program the microstimulator, to generate the clock used by the on-chip control circuitry, to deliver a constant current through a controlled current driver into the nerve tissue, and to control the operation of the overall circuitry using a low-power CMOS logic controller.

Programmable Implantable Pulse Generator (IPG)

Figure 38:
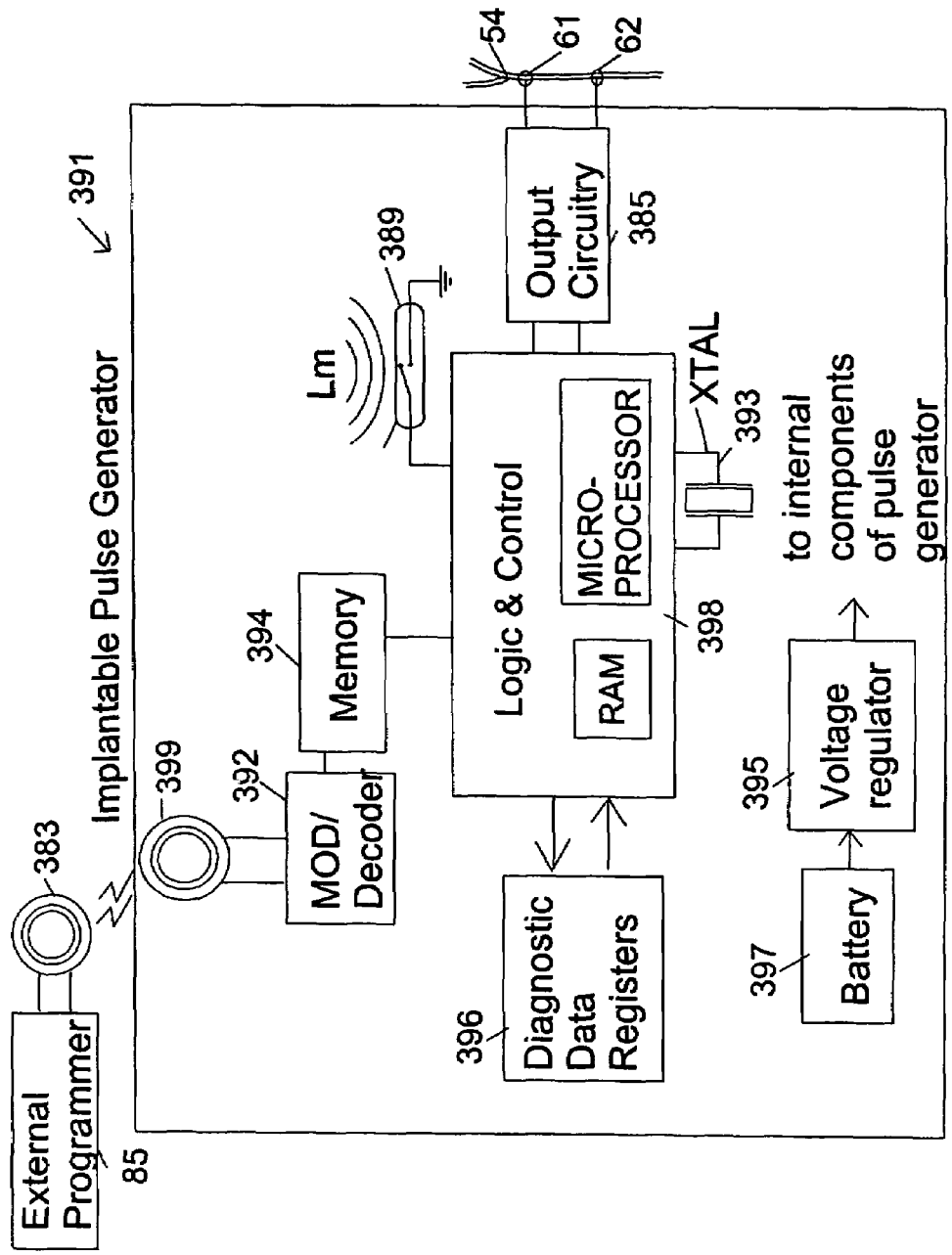
FIG. 38 is a simplified block diagram of the implantable pulse generator.

In one embodiment, a fully programmable implantable pulse generator (IPG), capable of generating stimulation and blocking pulses may be used. Shown in conjunction with FIG. 38, the implantable pulse generator unit 391 is preferably a microprocessor based device, where the entire circuitry is encased in a hermetically sealed titanium can. As shown in the overall block diagram, the logic & control unit 398 provides the proper timing for the output circuitry 385 to generate electrical pulses that are delivered to electrodes 61, 62 via a lead 40. Programming of the implantable pulse generator (IPG) is done via an external programmer 85, as described later. Once programmed via an external programmer 85, the implanted pulse generator 391 provides appropriate electrical stimulation pulses to the vagus nerve(s) 54 via electrodes 61,62.

This embodiment also comprises fixed pre-determined/pre-packaged programs. Examples of four stimulation states were given in the previous section, under "Programmer-less Implantable Pulse Generator (IPG)". These pre-packaged/pre-determined programs comprise unique combinations of pulse amplitude, pulse width, pulse frequency, ON-time and OFF-time. Any number of predetermined/pre-packaged programs, say 100, can be stored in the implantable pulse generator of this invention.

In addition, each parameter may be individually adjusted and stored in the memory 394. The range of programmable electrical stimulation parameters include both stimulating and blocking frequencies, and are shown in table five below.

TABLE 5

Programmable electrical parameter range

| PARAMER | RANGE |
| --- | --- |
| Pulse Amplitude | 0.1 Volt-15 Volts |
| Pulse width | 20 µS-5 mSec. |
| Stim. Frequency | 5 Hz-200 Hz |
| Freq. for blocking | DC to 750 Hz |
| On-time | 5 Secs-24 hours |
| Off-time | 5 Secs-24 hours |
| Ramp | ON/OFF |

Figure 39:
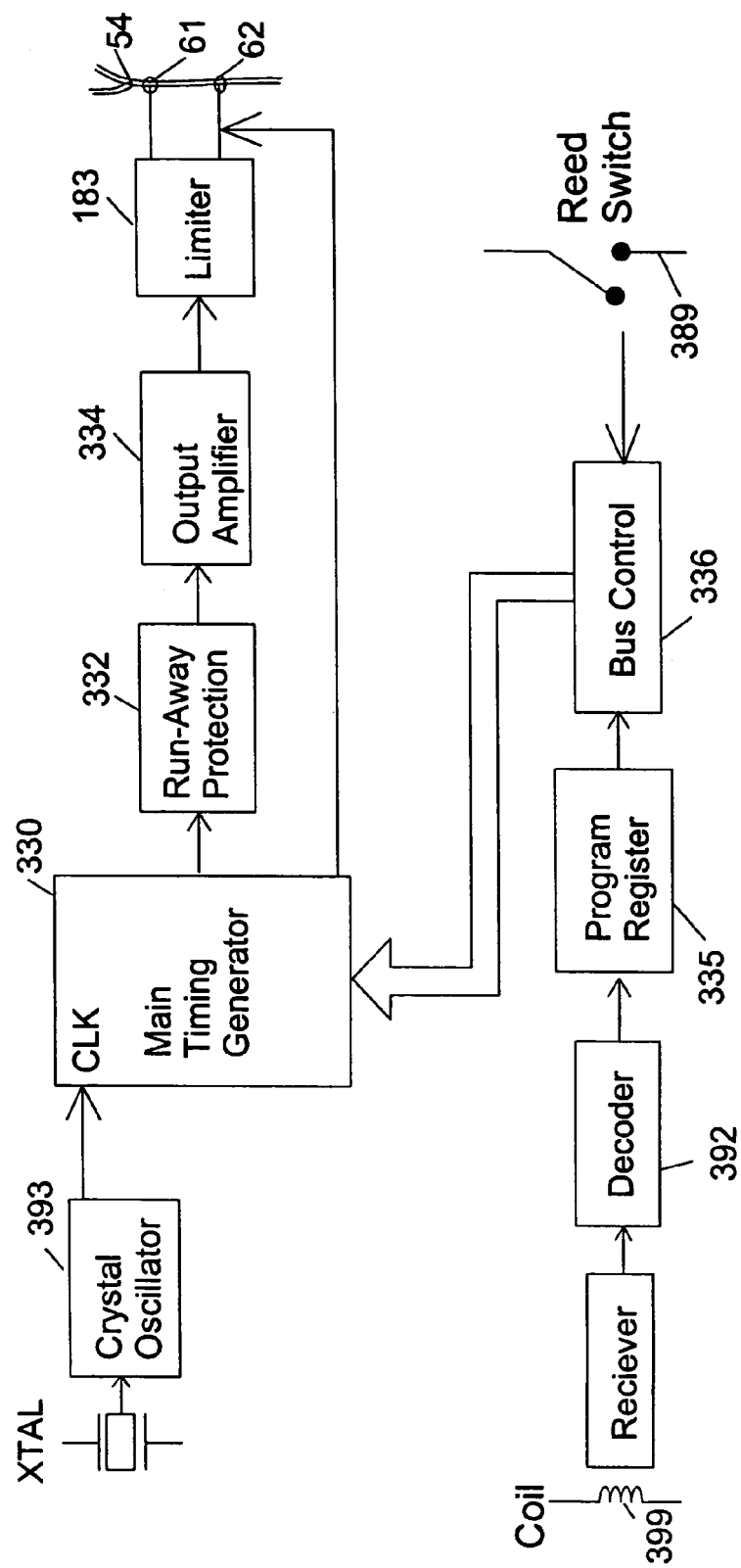
FIG. 39 is a functional block diagram of a microprocessor-based implantable pulse generator.
Figure 40:
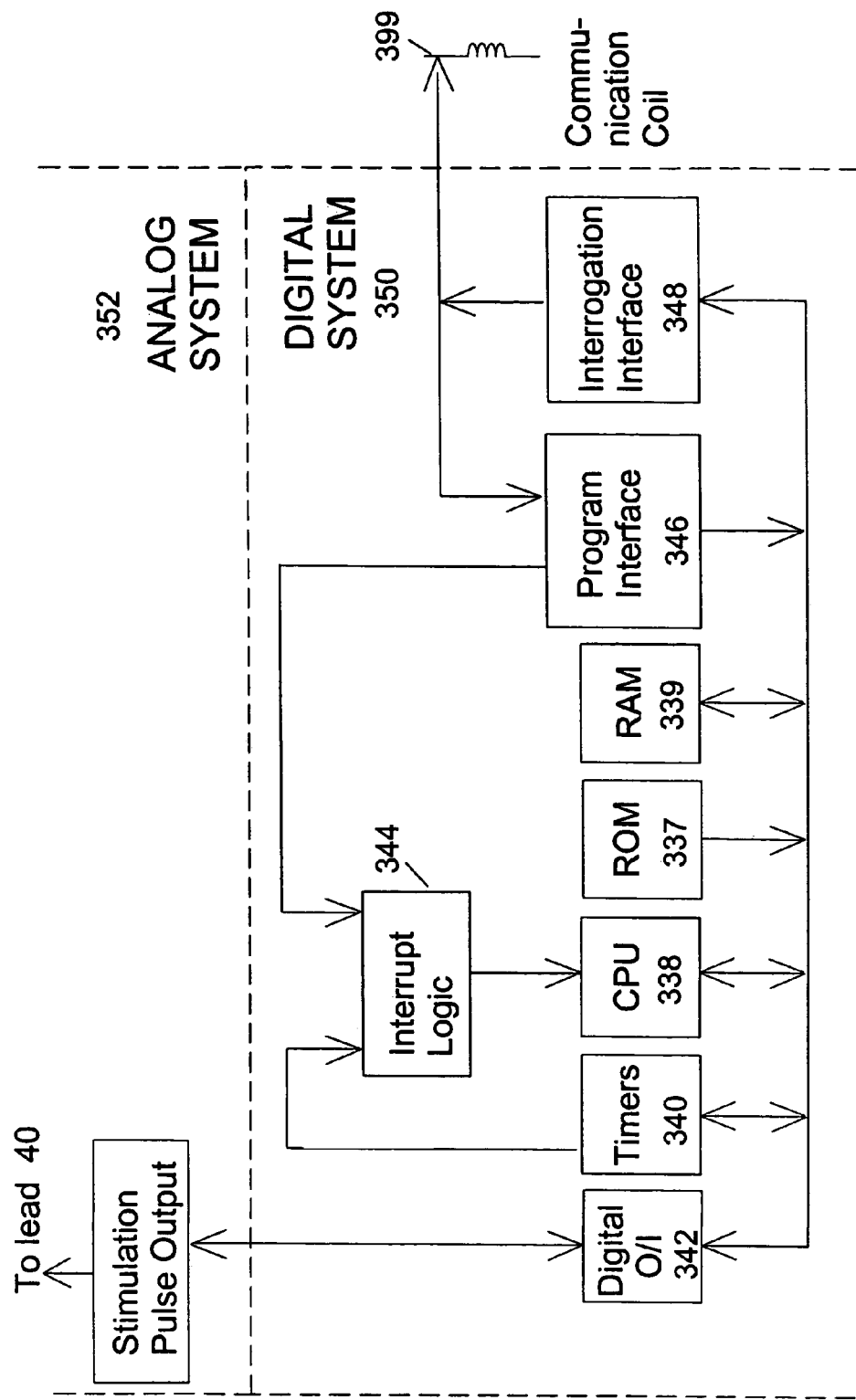
FIG. 40 shows details of implanted pulse generator.

Shown in conjunction with FIGS. 39 and 40, the electronic stimulation module comprises both digital 350 and analog 352 circuits. A main timing generator 330 (shown in FIG. 39), controls the timing of the analog output circuitry for delivering neuromodulating pulses to the vagus nerve 54, via output amplifier 334. Limiter 183 prevents excessive stimulation energy from getting into the vagus nerve 54. The main timing generator 330 receiving clock pulses from crystal oscillator 393. Main timing generator 330 also receiving input from programmer 85 via coil 399. FIG. 36 highlights other portions of the digital system such as CPU 338, ROM 337, RAM 339, program interface 346, interrogation interface 348, timers 340, and digital Oil 342.

Most of the digital functional circuitry 350 is on a single chip (IC). This monolithic chip along with other IC's and components such as capacitors and the input protection diodes are assembled together on a hybrid circuit. As well known in the art, hybrid technology is used to establish the connections between the circuit and the other passive components. The integrated circuit is hermetically encapsulated in a chip carrier. A coil 399 situated under the hybrid substrate is used for bidirectional telemetry. The hybrid and battery 397 are encased in a titanium can 65. This housing is a two-part titanium capsule that is hermetically sealed by laser welding. Alternatively, electron-beam welding can also be used. The header 79 is a cast epoxy-resin with hermetically sealed feedthrough, and form the lead 40 connection block.

Figure 41A:
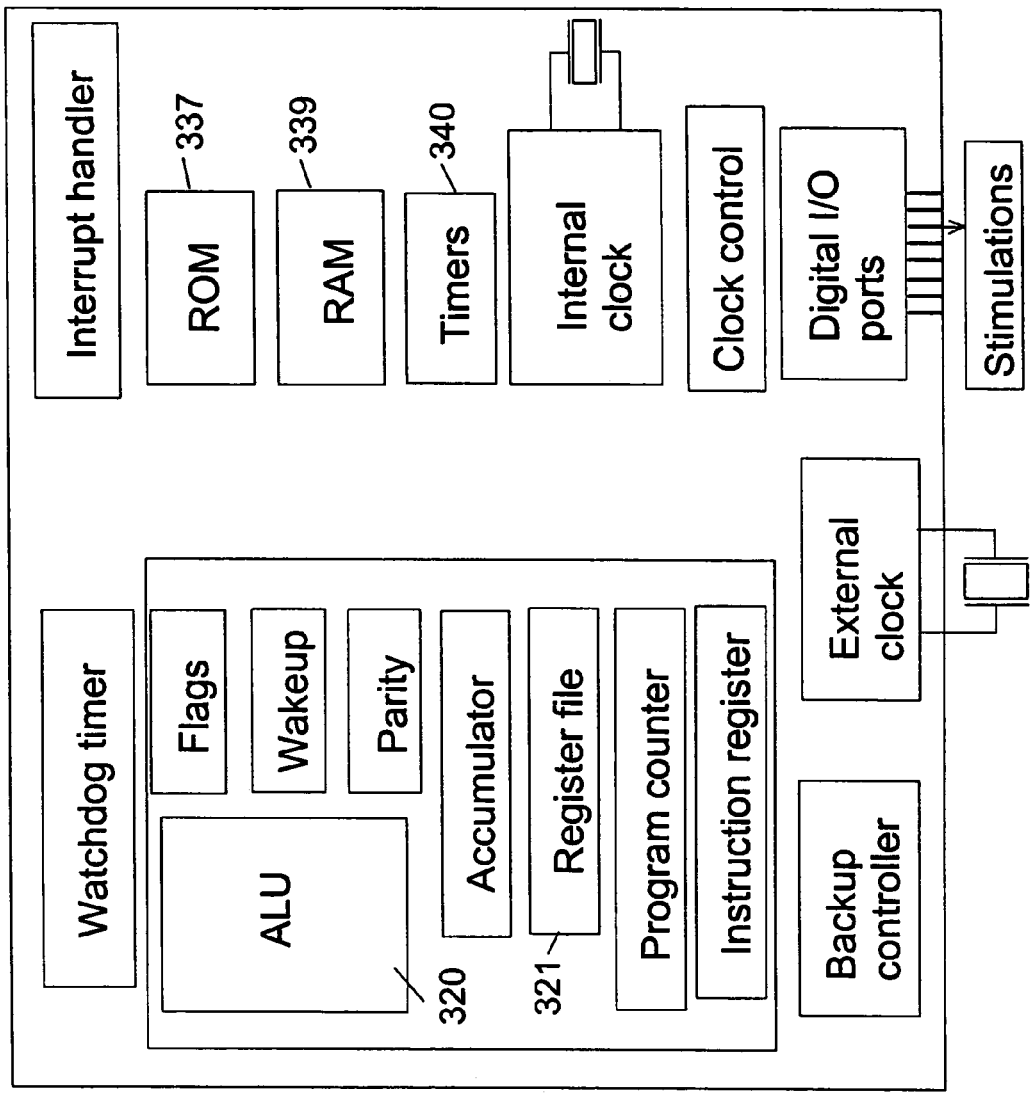
FIGS. 41A and 41B shows details of digital components of the implantable circuitry.

For further details, FIG. 41A highlights the general components of an 8-bit microprocessor as an example. It will be obvious to one skilled in the art that higher level microprocessor, such as a 16-bit or 32-bit may be utilized, and is considered within the scope of this invention. It comprises a ROM 337 to store the instructions of the program to be executed and various programmable parameters, a RAM 339 to store the various intermediate parameters, timers 340 to track the elapsed intervals, a register file 321 to hold intermediate values, an ALU 320 to perform the arithmetic calculation, and other auxiliary units that enhance the performance of a microprocessor-based IPG system.

Figure 41B:
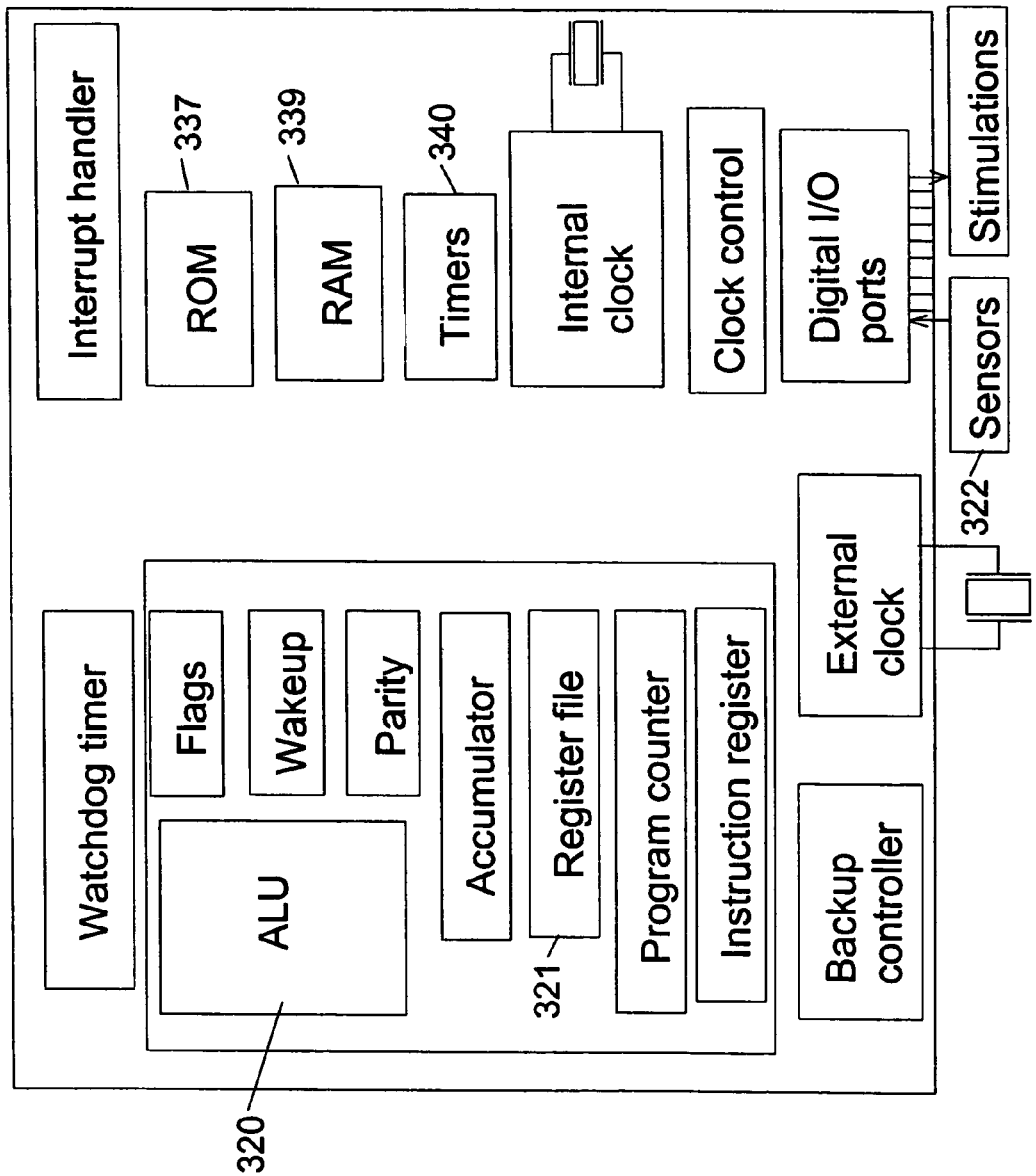

The size of ROM 337 and RAM 339 units are selected based on the requirements of the algorithms and the parameters to be stored. The number of registers in the register file 321 are decided based upon the complexity of computation and the required number of intermediate values. Timers 340 of different precision are used to measure the elapsed intervals. Even though this embodiment does not have external sensors to control timing, future embodiments may have sensors 322 to effect the timing as shown in conjunction with FIG. 41B.

In this embodiment, the two main components of microprocessor are the datapath and control. The datapath performs the arithmetic operation and the control directs the datapath, memory, and I/O devices to execute the instruction of the program. The hardware components of the microprocessor are designed to execute a set of simple instructions. In general the complexity of the instruction set determines the complexity of datapth elements and controls of the microprocessor.

In this embodiment, the microprocessor is provided with a fixed operating routine. Future embodiments may be provided with the capability of actually introducing program changes in the implanted pulse generator. The instruction set of the microprocessor, the size of the register files, RAM and ROM are selected based on the performance needed and the type of the algorithms used. In this application of pulse generator, in which several algorithms can be loaded and modified, Reduced Instruction Set Computer (RISC) architecture is useful. RISC architecture offers advantages because it can be optimized to reduce the instruction cycle which in turn reduces the run time of the program and hence the current drain. The simple instruction set architecture of RISC and its simple hardware can be used to implement any algorithm without much difficulty. Since size is also a major consideration, an 8-bit microprocessor is used for the purpose. As most of the arithmetic calculation are based on a few parameters and are rather simple, an accumulator architecture is used to save bits from specifying registers. Each instruction is executed in multiple clock cycles, and the clock cycles are broadly classified into five stages: an instruction fetch, instruction decode, execution, memory reference, and write back stages. Depending on the type of the instruction, all or some of these stages are executed for proper completion.

Initially, an optimal instruction set architecture is selected based on the algorithm to be implemented and also taking into consideration the special needs of a microprocessor based implanted pulse generator (IPG). The instructions are broadly classified into Load/store instructions, Arithmetic and logic instructions (ALU), control instructions and special purpose instructions.

The instruction format is decided based upon the total number of instructions in the instruction set. The instructions fetched from memory are 8 bits long in this example. Each instruction has an opcode field (2 bits), a register specifier field (3-bits), and a 3-bit immediate field. The opcode field indicates the type of the instruction that was fetched. The register specifier indicates the address of the register in the register file on which the operations are performed. The immediate field is shifted and sign extended to obtain the address of the memory location in load/store instruction. Similarly, in branch and jump instruction, the offset field is used to calculate the address of the memory location the control needs to be transferred to.

Figure 42A:
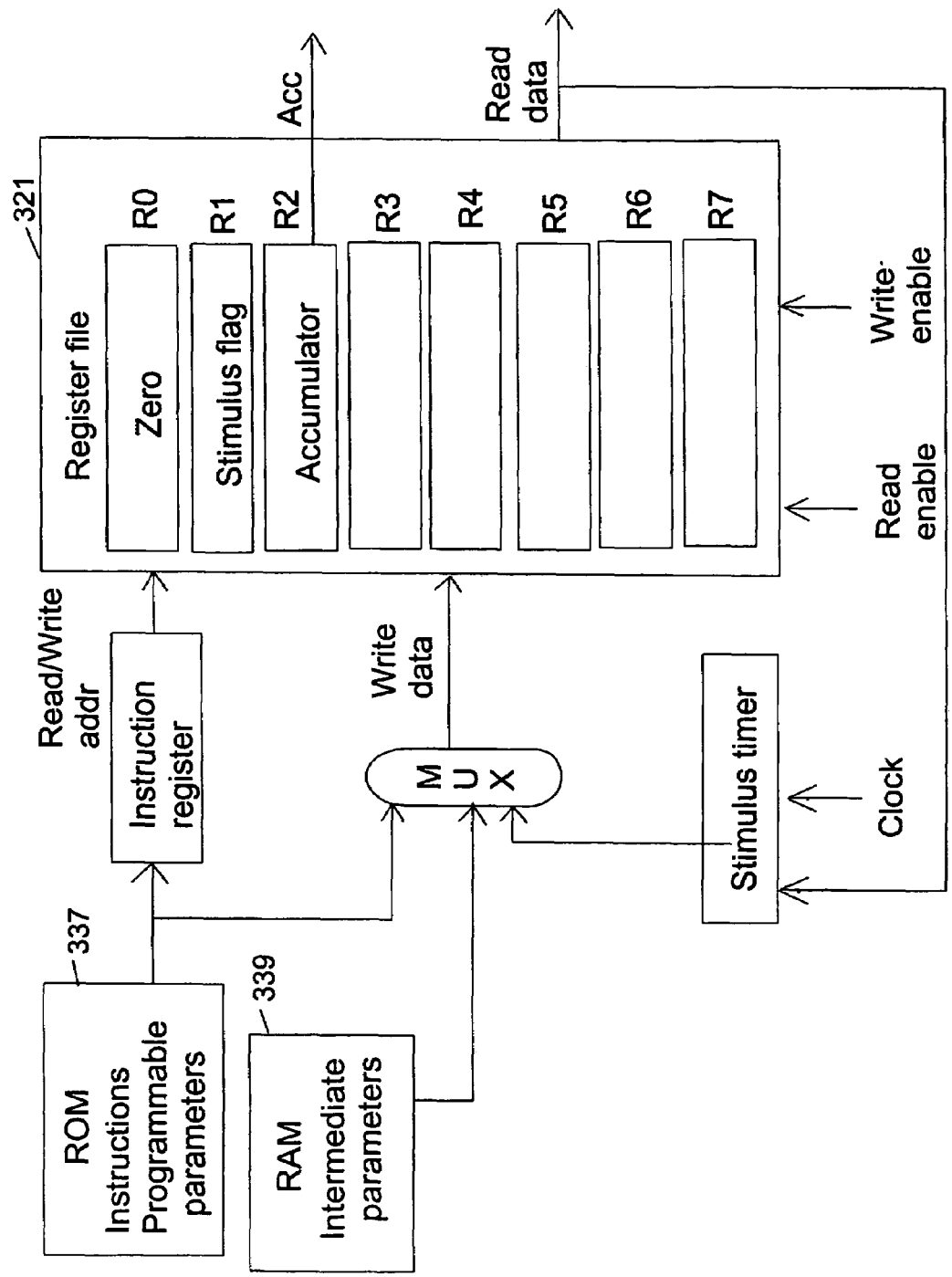
FIG. 42A shows a schematic diagram of the register file, timers and ROM/RAM.

Shown in conjunction with FIG. 42A, the register file 321, which is a collection of registers in which any register can be read from or written to specifying the number of the register in the file. Based on the requirements of the design, the size of the register file is decided. For the purposes of implementation of stimulation pulses algorithms, a register file of eight registers is sufficient, with three special purpose register (0-2) and five general purpose registers (3-7), as shown in FIG. 42A. Register "0" always holds the value "zero". Register "1" is dedicated to the pulse flags. Register "2" is an accumulator in which all the arithmetic calculations are performed. The read/write address port provides a 3-bit address to identify the register being read or written into. The write data port provides 8-bit data to be written into the registers either from ROM/RAM or timers. Read enable control, when asserted enables the register file to provide data at the read data port. Write enable control enables writing of data being provided at the write data port into a register specified by the read/write address.

Generally, two or more timers are required to implement the algorithm for the IPG. The timers are read and written into just as any other memory location. The timers are provided with read and write enable controls.

The arithmetic logic unit is an important component of the microprocessor. It performs the arithmetic operation such as addition, subtraction and logical operations such as AND and OR. The instruction format of ALU instructions consists of an opcode field (2 bits), a function field (2 bits) to indicate the function that needs to be performed, and a register specifier (3 bits) or an immediate field (4 bits) to provide an operand.

Figure 42B:
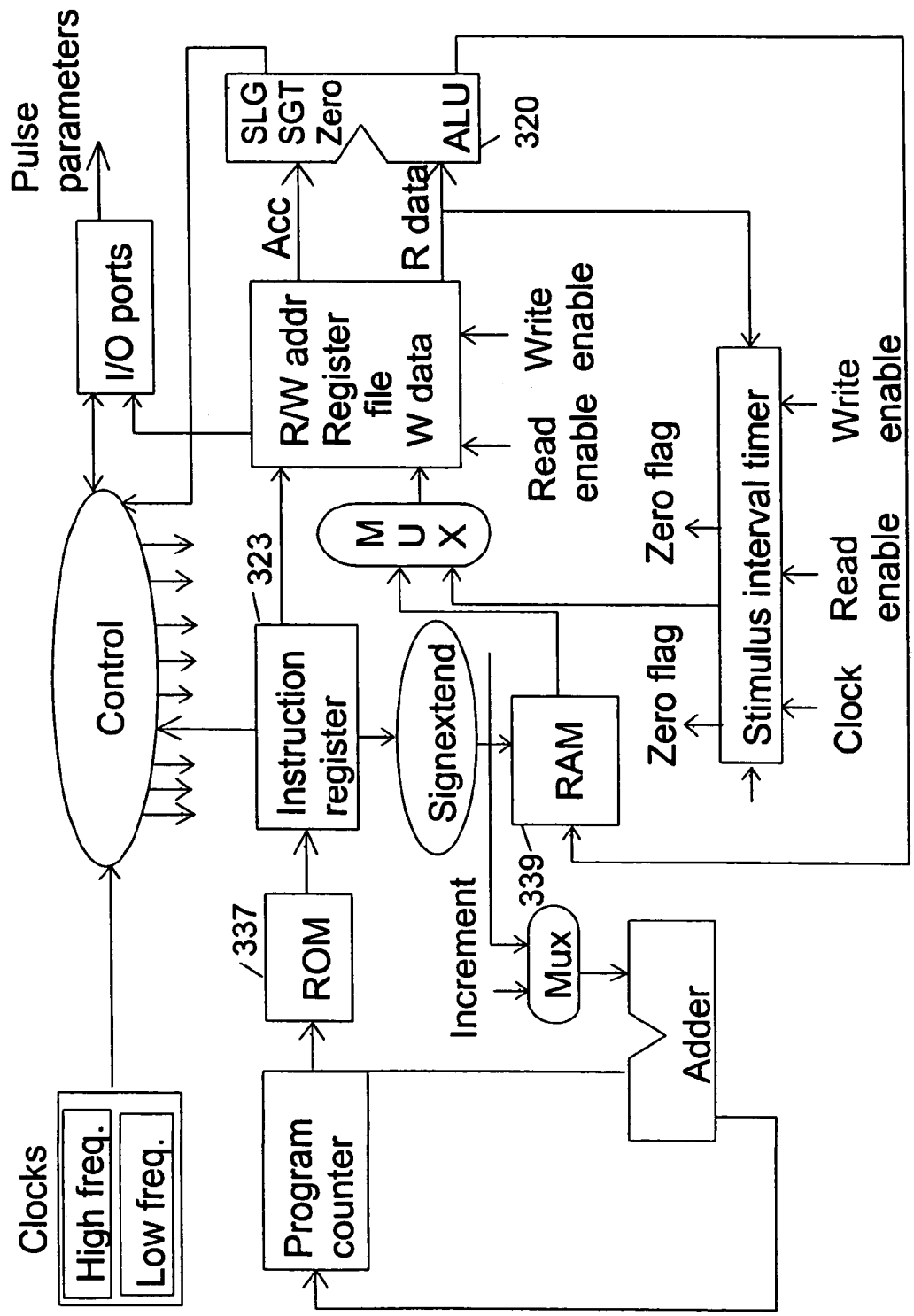
FIG. 42B shows datapath and control of custom-designed microprocessor based pulse generator.

The hardware components discussed above constitute the important components of a datapath. Shown in conjunction with FIG. 42B, there are some special purpose registers such a program counter (PC) to hold the address of the instruction being fetched from ROM 337 and instruction register (IR) 323, to hold the instruction that is fetched for further decoding and execution. The program counter is incremented in each instruction fetch stage to fetch sequential instruction from memory. In the case of a branch or jump instruction, the PC multiplexer allows to choose from the incremented PC value or the branch or jump address calculated. The opcode of the instruction fetched (IR) is provided to the control unit to generate the appropriate sequence of control signals, enabling data flow through the datapath. The register specification field of the instruction is given as read/write address to the register file, which provides data from the specified field on the read data port. One port of the ALU is always provided with the contents of the accumulator and the other with the read data port. This design is therefore referred to as accumulator-based architecture. The sign-extended offset is used for address calculation in branch and jump instructions. The timers are used to measure the elapsed interval and are enabled to count down on a low-frequency clock. The timers are read and written into, just as any other memory location (FIG. 42B).

In a multicycle implementation, each stage of instruction execution takes one clock cycle. Since the datapath takes multiple clock cycles per instruction, the control must specify the signals to be asserted in each stage and also the next step in the sequence. This can be easily implemented as a finite state machine.

A finite state machine consists of a set of states and directions on how to change states. The directions are defined by a next-state function, which maps the current state and the inputs to a new state. Each stage also indicates the control signals that need to be asserted. Every state in the finite state machine takes one clock cycle. Since the instruction fetch and decode stages are common to all the instruction, the initial two states are common to all the instruction. After the execution of the last step, the finite state machine returns to the fetch state.

A finite state machine can be implemented with a register that holds the current stage and a block of combinational logic such as a PLA. It determines the datapath signals that need to be asserted as well as the next state. A PLA is described as an array of AND gates followed by an array of OR gates. Since any function can be computed in two levels of logic, the two-level logic of PLA is used for generating control signals.

The occurrence of a wakeup event initiates a stored operating routine corresponding to the event. In the time interval between a completed operating routine and a next wake up event, the internal logic components of the processor are deactivated and no energy is being expended in performing an operating routine.

A further reduction in the average operating current is obtained by providing a plurality of counting rates to minimize the number of state changes during counting cycles. Thus intervals which do not require great precision, may be timed using relatively low counting rates, and intervals requiring relatively high precision, such as stimulating pulse width, may be timed using relatively high counting rates.

Figure 43:
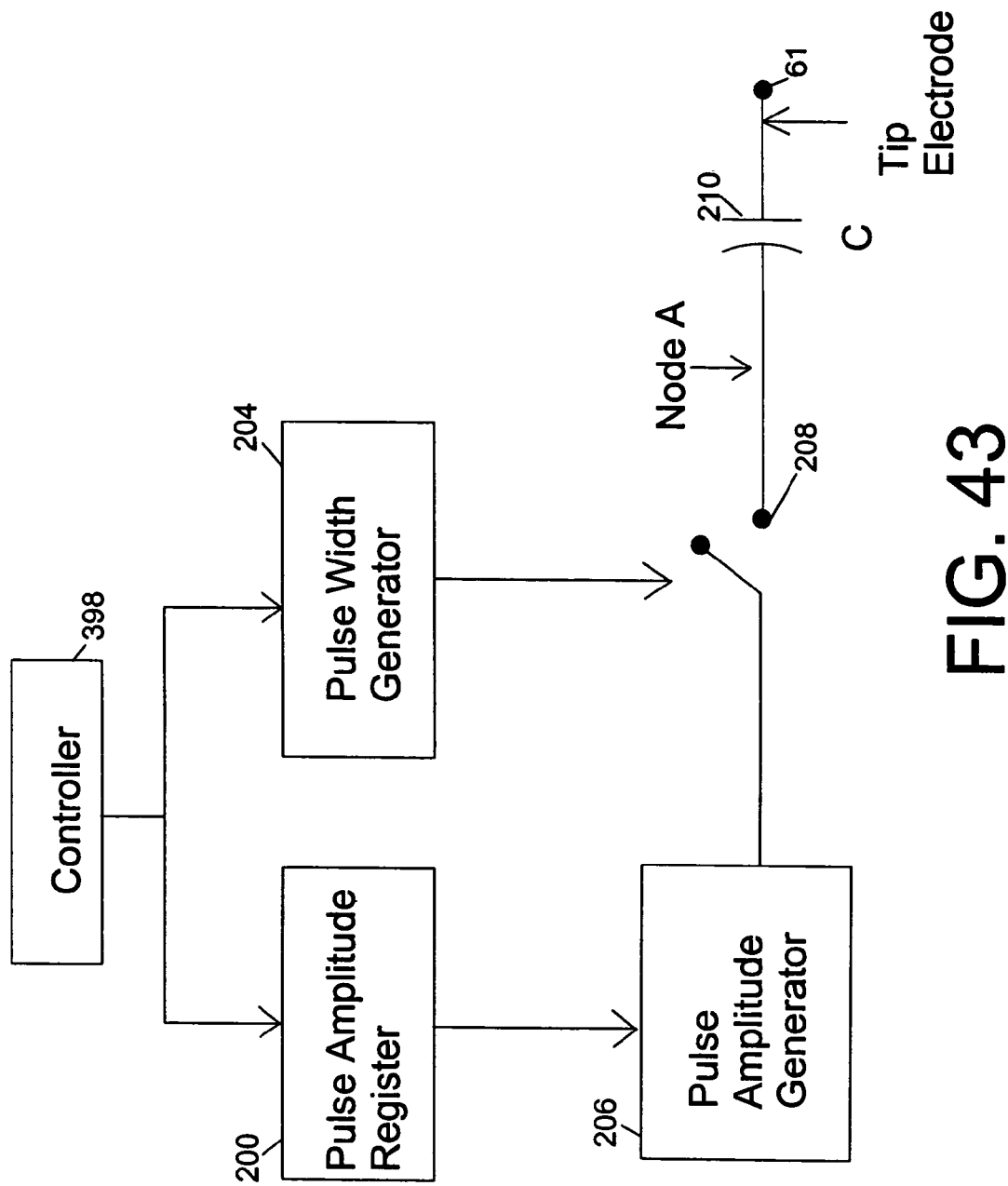
FIG. 43 is a block diagram for generation of a pre-determined stimulation pulse.

The logic and control unit 398 of the IPG controls the output amplifiers. The pulses have predetermined energy (pulse amplitude and pulse width) and are delivered at a time determined by the therapy stimulus controller. The circuitry in the output amplifier, shown in conjunction with (FIG. 43) generates an analog voltage or current that represents the pulse amplitude. The stimulation controller module initiates a stimulus pulse by closing a switch 208 that transmits the analog voltage or current pulse to the nerve tissue through the tip electrode 61 of the lead 40. The output circuit receiving instructions from the stimulus therapy controller 398 that regulates the timing of stimulus pulses and the amplitude and duration (pulse width) of the stimulus. The pulse amplitude generator 206 determines the configuration of charging and output capacitors necessary to generate the programmed stimulus amplitude. The output switch 208 is closed for a period of time that is controlled by the pulse width generator 204. When the output switch 208 is closed, a stimulus is delivered to the tip electrode 61 of the lead 40.

Figure 44:
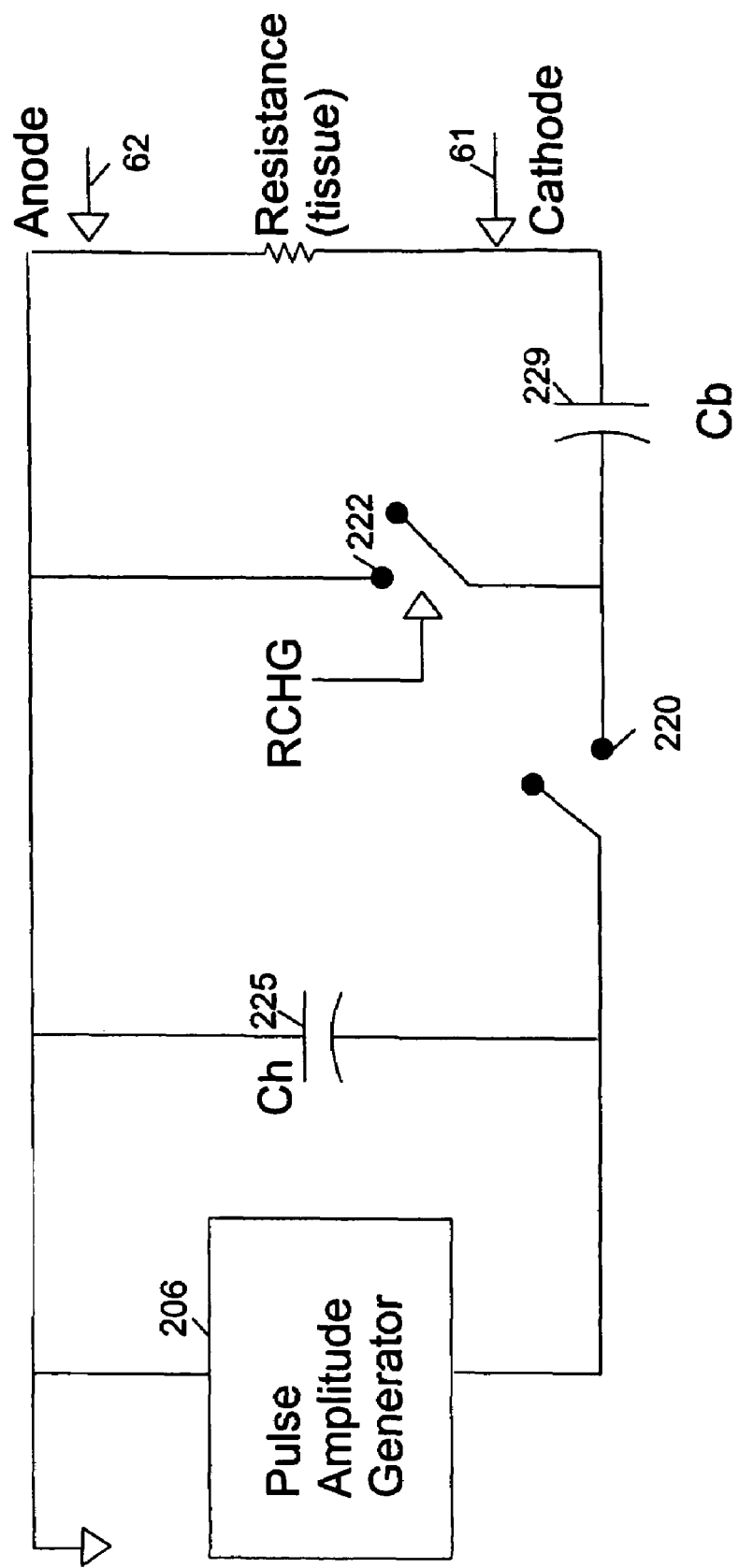
FIG. 44 is a simplified schematic for delivering stimulation pulses.

The constant-voltage output amplifier applies a voltage pulse to the distal electrode (cathode) 61 of the lead 40. A typical circuit diagram of a voltage output circuit is shown in FIG. 44. This configuration contains a stimulus amplitude generator 206 for generating an analog voltage. The analog voltage represents the stimulus amplitude and is stored on a holding capacitor $C_h$ 225. Two switches are used to deliver the stimulus pulses to the lead 40, a stimulating delivery switch 220, and a recharge switch 222, that reestablishes the charge equilibrium after the stimulating pulse has been delivered to the nerve tissue. Since these switches have leakage currents that can cause direct current (DC) to flow into the lead system 40, a DC blocking capacitor $C_b$ 229, is included. This is to prevent any possible corrosion that may result from the leakage of current in the lead 40. When the stimulus delivery switch 220 is closed, the pulse amplitude analog voltage stored in the ($C_h$ 225) holding capacitor is transferred to the cathode electrode 61 of the lead 40 through the coupling capacitor, $C_b$ 229. At the end of the stimulus pulse, the stimulus delivery switch 220 opens. The pulse duration being the interval from the closing of the switch 220 to its reopening.

During the stimulus delivery, some of the charge stored on $C_h$ 225 has been transferred to $C_b$ 229, and some has been delivered to the lead system 40 to stimulate the nerve tissue.

To reestablish equilibrium, the recharge switch 222 is closed, and a rapid recharge pulse is delivered. This is intended to remove any residual charge remaining on the coupling capacitor $C_b$ 229, and the stimulus electrodes on the lead (polarization). Thus, the stimulus is delivered as the result of closing and opening of the stimulus delivery 220 switch and the closing and opening of the RCHG switch 222. At this point, the charge on the holding $C_h$ 225 must be replenished by the stimulus amplitude generator 206 before another stimulus pulse can be delivered.

Figure 45:
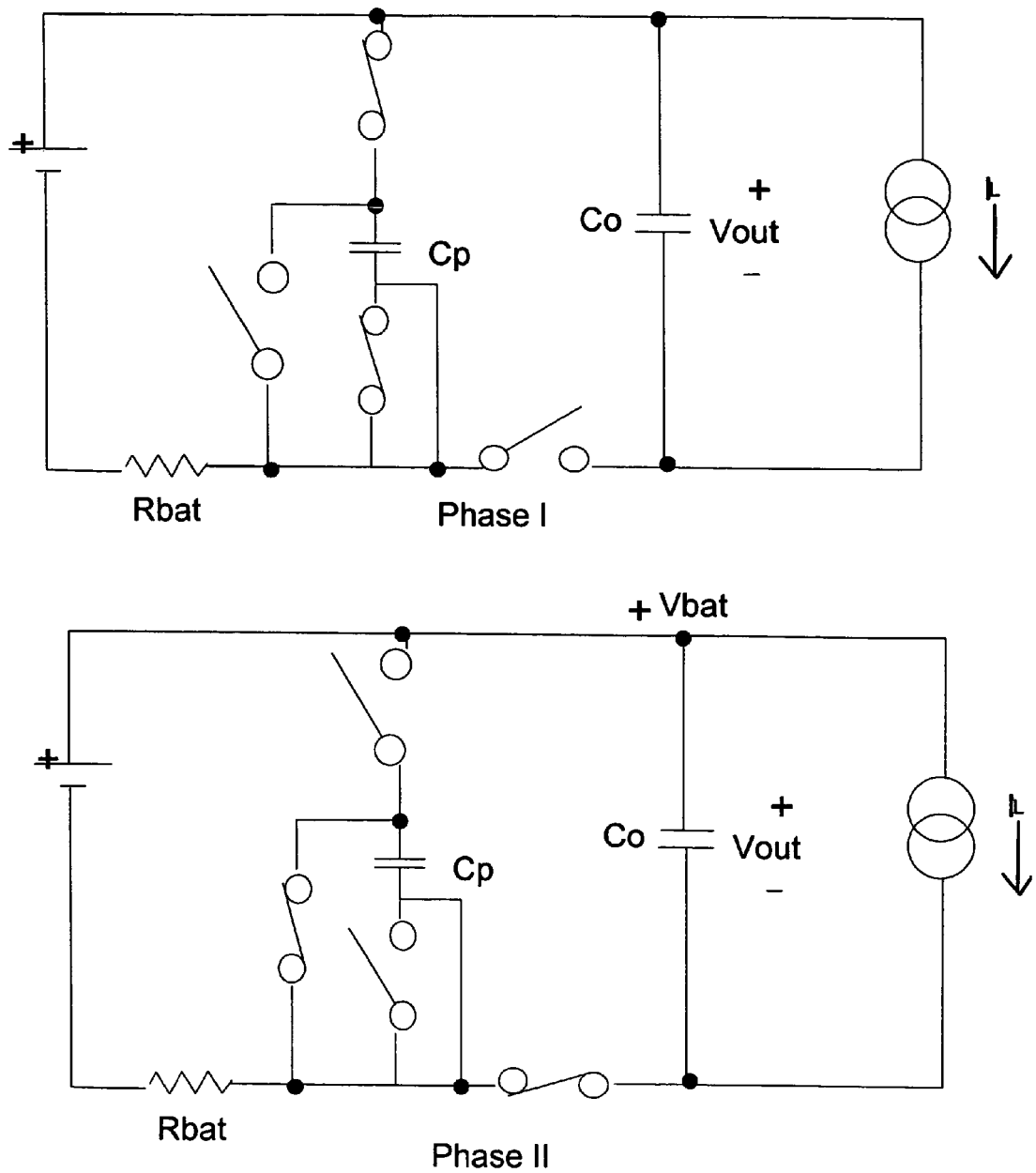
FIG. 45 is a circuit diagram of a voltage doubler.

The pulse generating unit charges up a capacitor and the capacitor is discharged when the control (timing) circuitry requires the delivery of a pulse. This embodiment utilizes a constant voltage pulse generator, even though a constant current pulse generator can also be utilized. Pump-up capacitors are used to deliver pulses of larger magnitude than the potential of the batteries. The pump up capacitors are charged in parallel and discharged into the output capacitor in series. Shown in conjunction with FIG. 45 is a circuit diagram of a voltage doubler which is shown here as an example. For higher multiples of battery voltage, this doubling circuit can be cascaded with other doubling circuits. As shown in FIG. 45, during phase I (top of FIG. 45), the pump capacitor $C_p$ is charged to $V_{bat}$ and the output capacitor $C_o$ supplies charge to the load. During phase II, the pump capacitor charges the output capacitor, which is still supplying the load current. In this case, the voltage drop across the output capacitor is twice the battery voltage.

Figure 46:
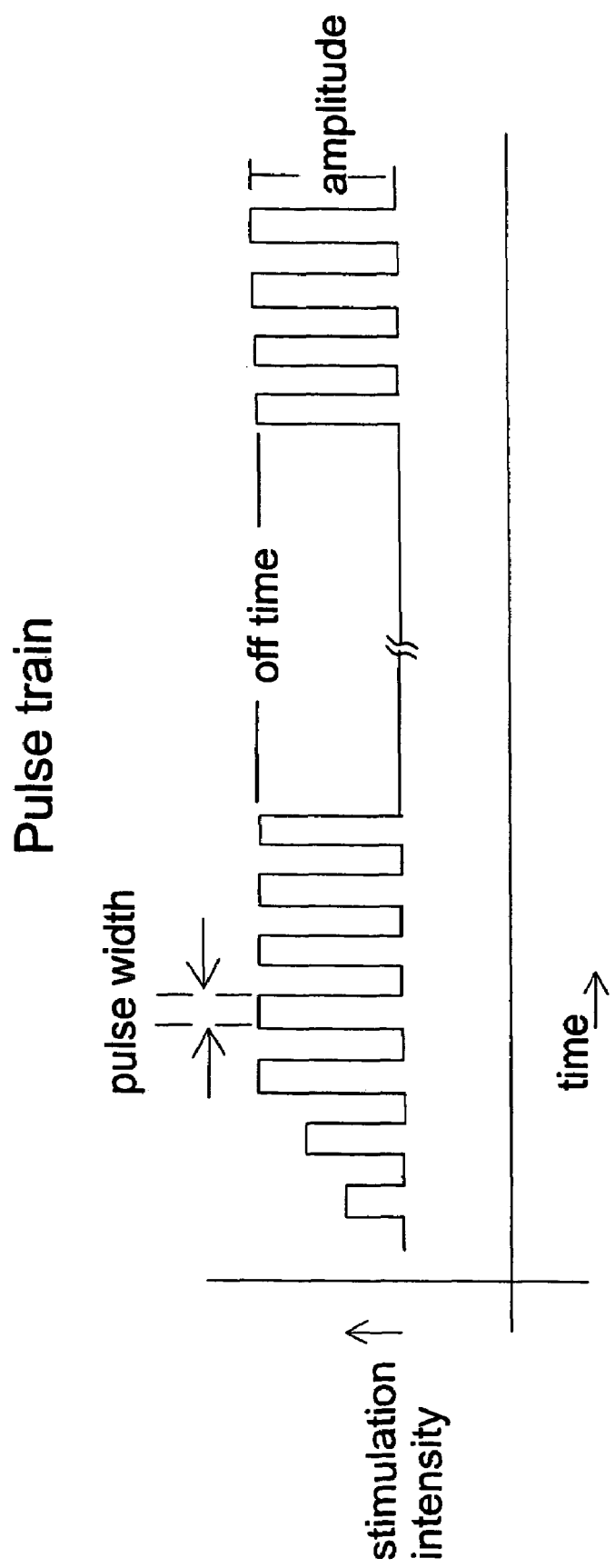
FIG. 46 is a diagram depicting ramping-up of a pulse train.

FIG. 46 shows an example of the pulse trains that are delivered with this embodiment. The microcontroller is configured to deliver the pulse train as shown in the figure, i.e. there is "ramping up" of the pulse train. The purpose of the ramping-up is to avoid sudden changes in stimulation, when the pulse train begins.

Figure 10A:
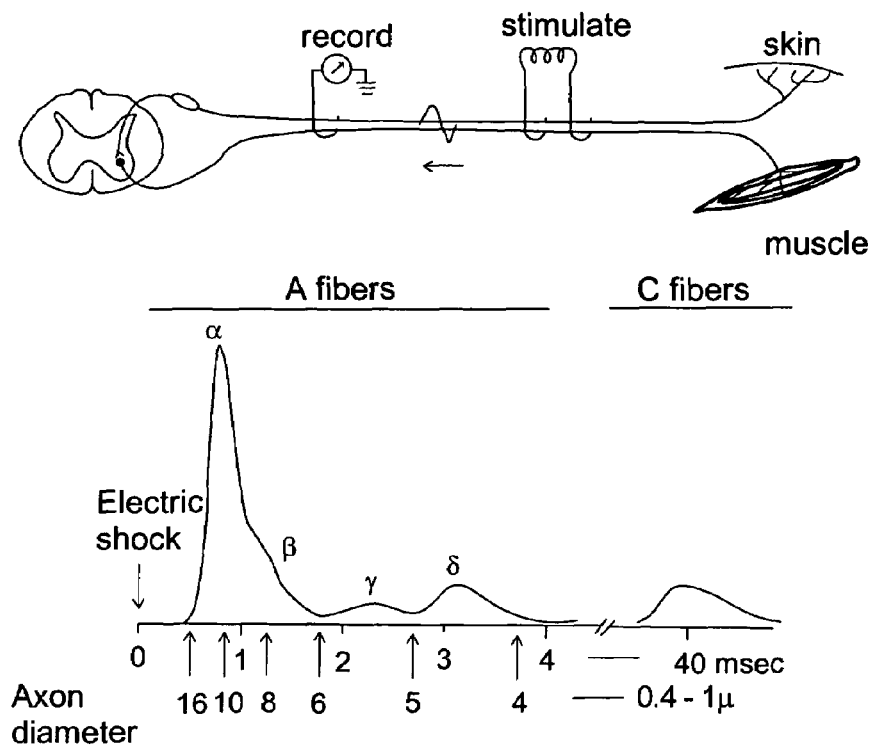
FIG. 10A is a diagram showing recordings of compound action potentials.
Figure 10:
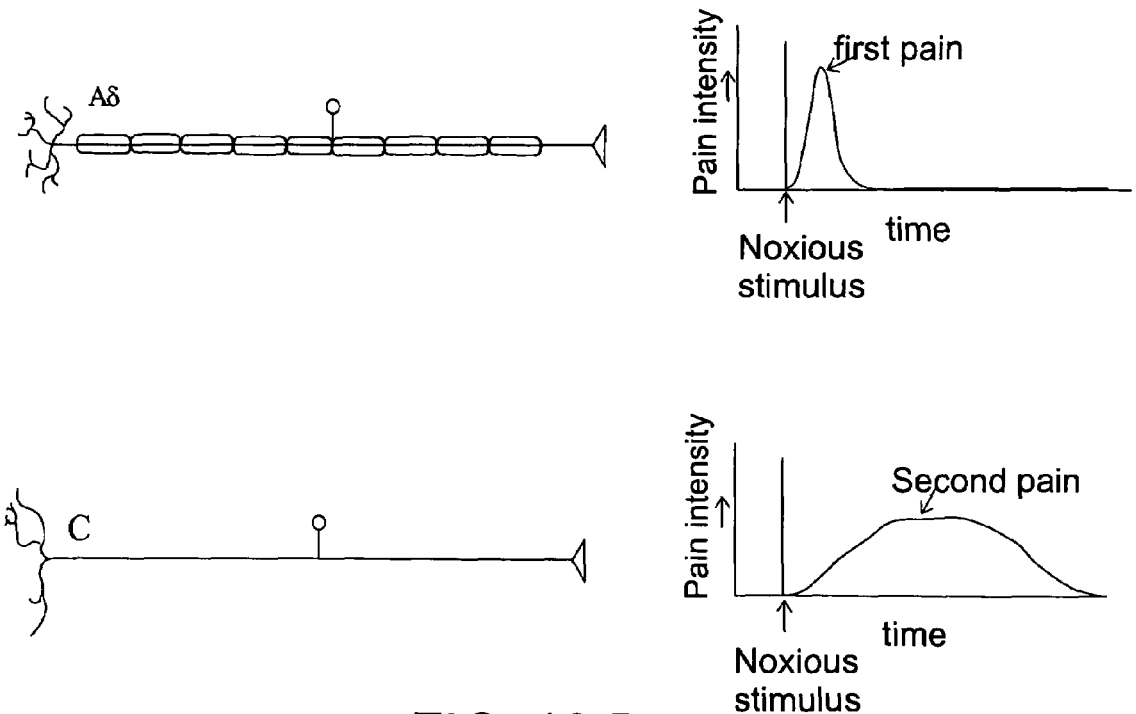
FIG. 10B is a schematic diagram showing conduction of first pain and second pain.
Figure 11:
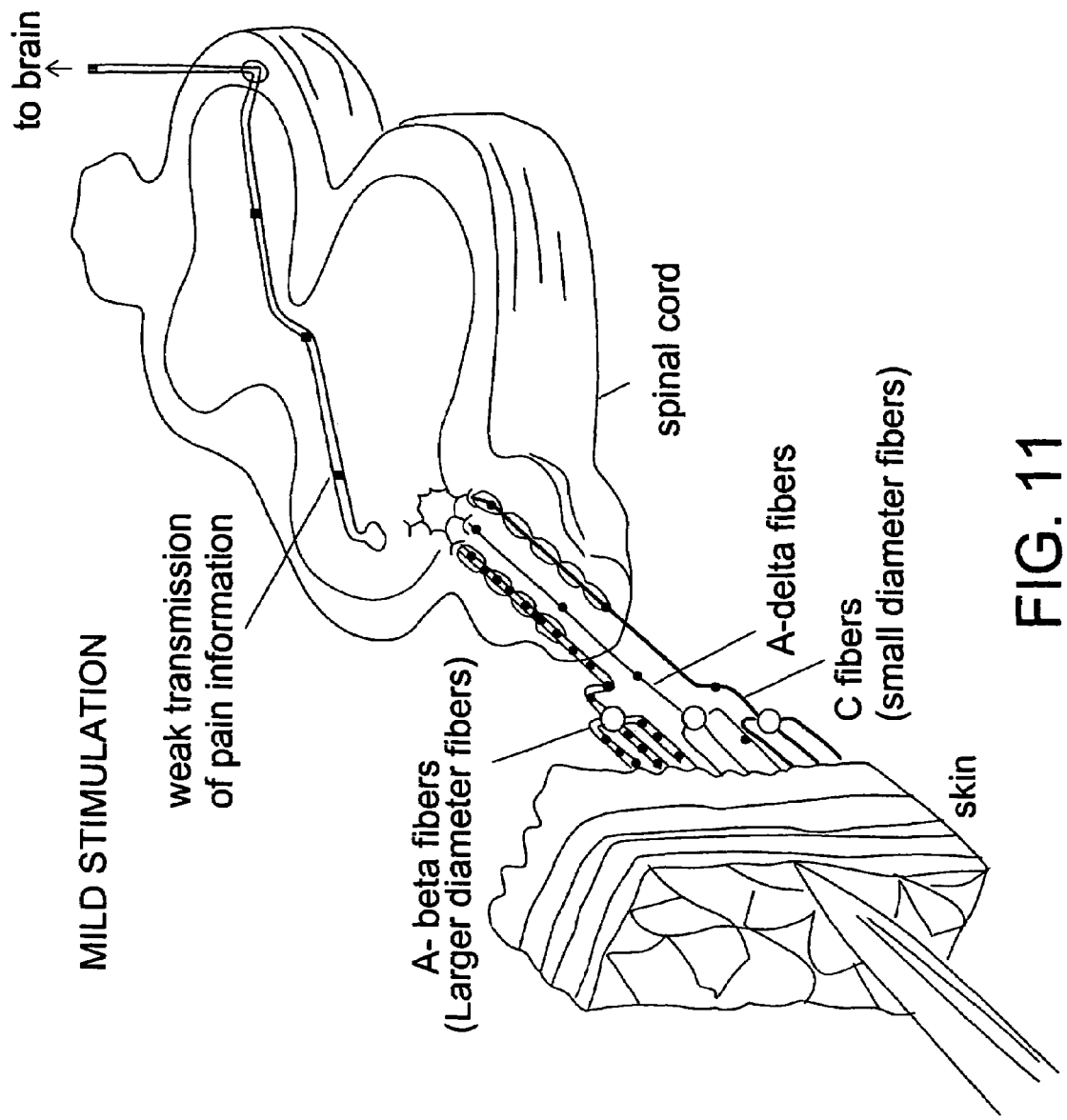
FIG. 11 is a schematic illustration showing mild stimulation being carried over the large diameter A-fibers.
Figure 12:
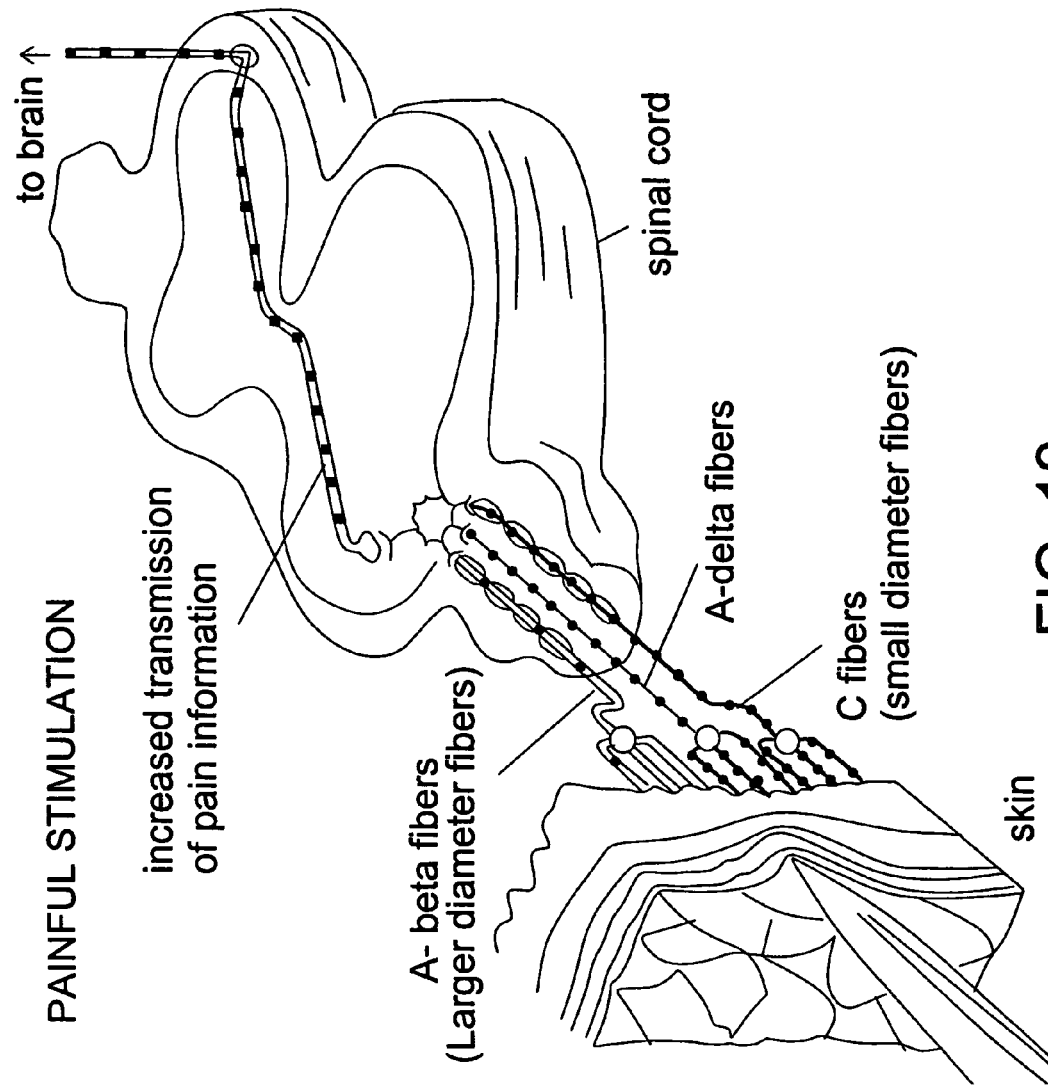
FIG. 12 is a schematic illustration showing painful stimulation being carried over small diameter C-fibers
Figure 13:
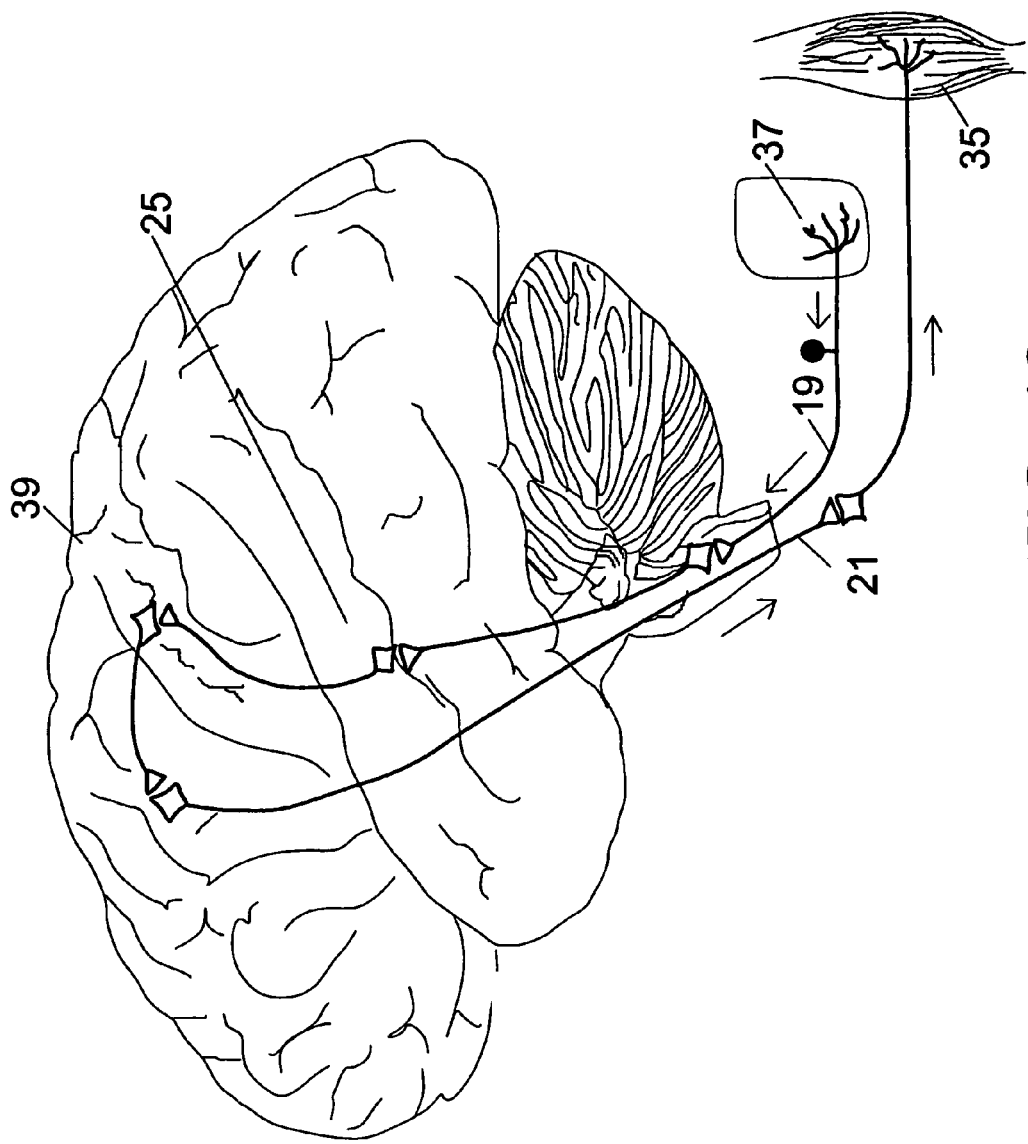
FIG. 13 is a schematic diagram of brain showing afferent and efferent pathways.
Figure 14:
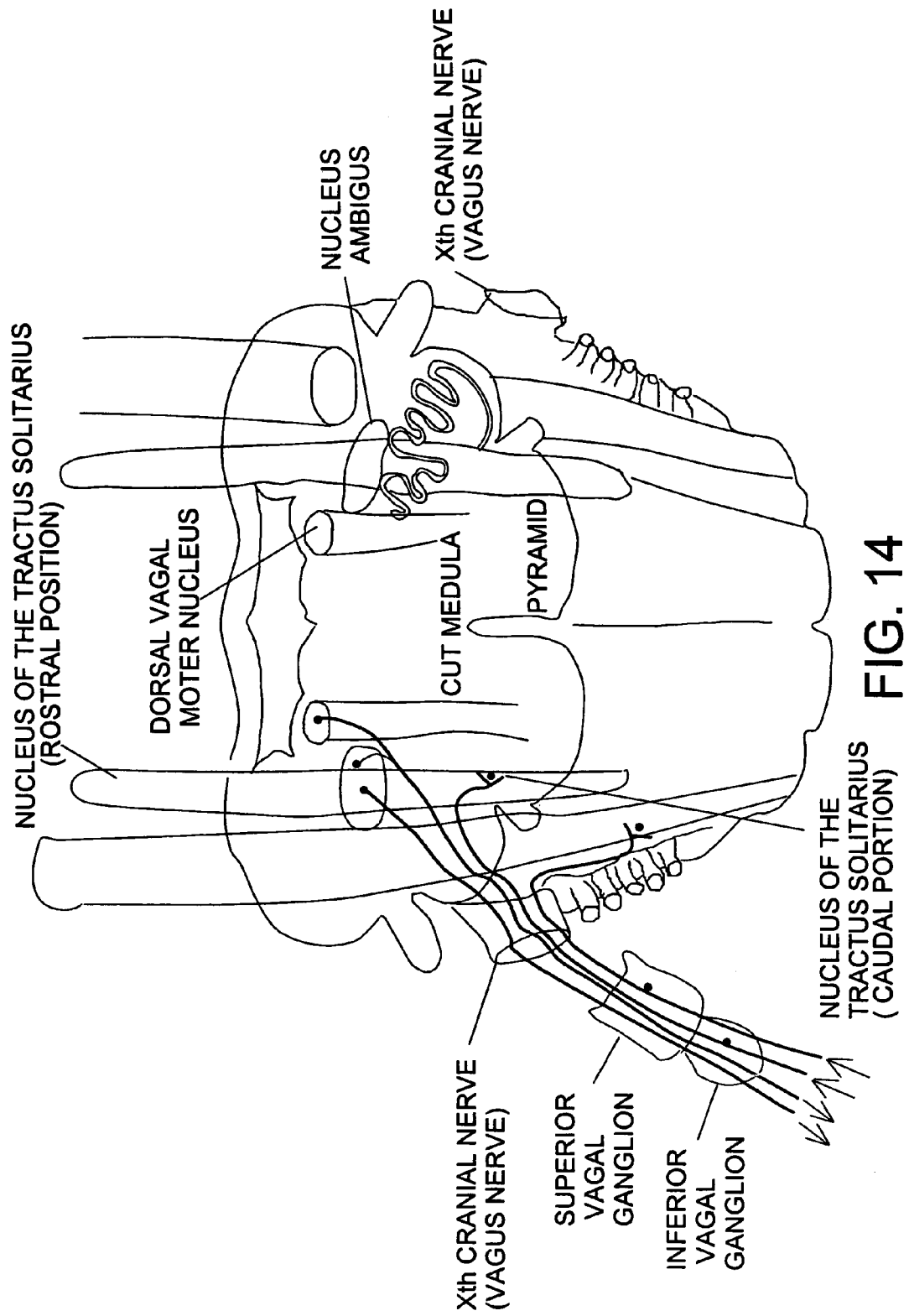
FIG. 14 is a schematic diagram showing the vagus nerve at the level of the nucleus of the solitary tract.
Figure 15:
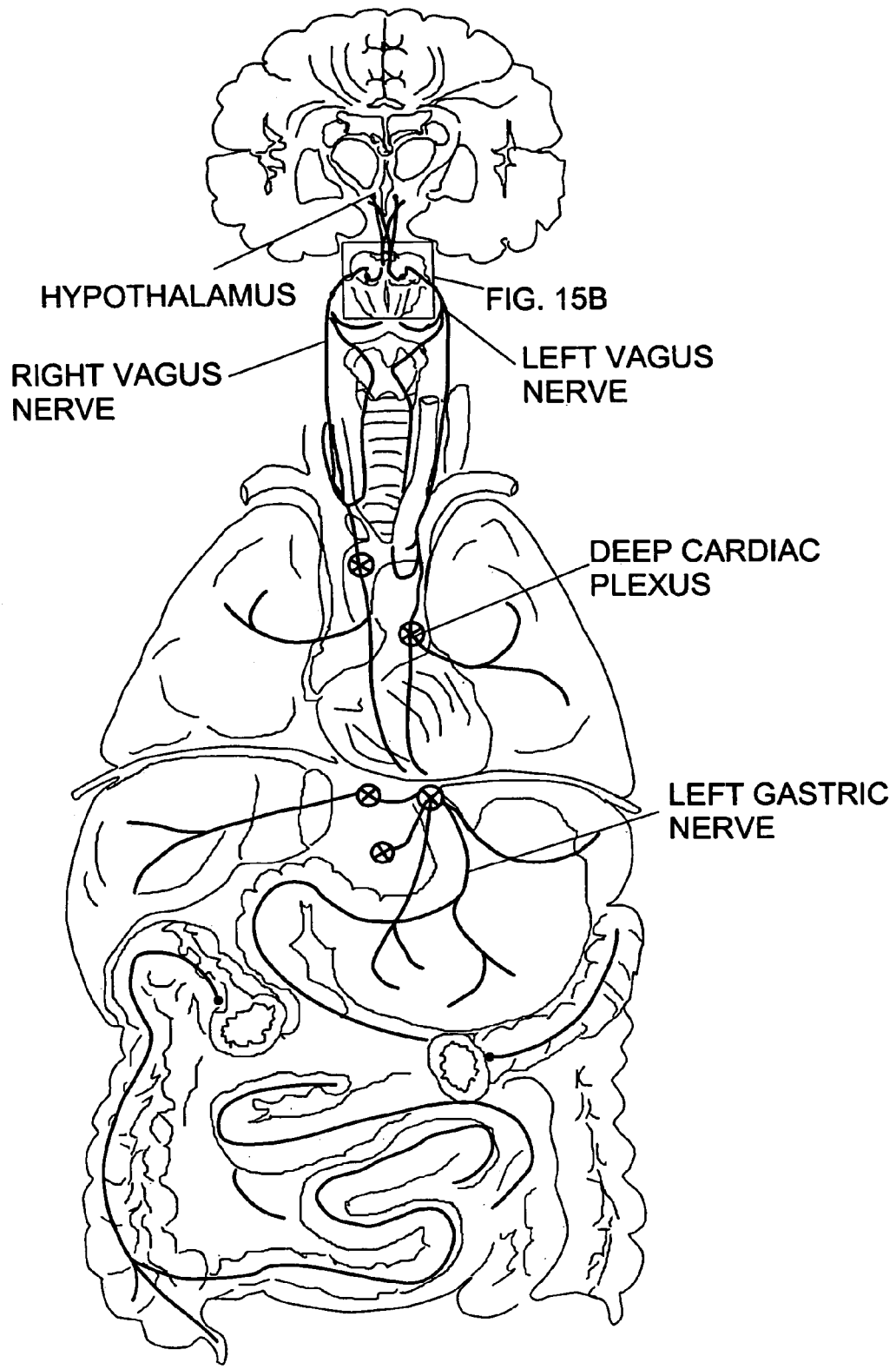
FIG. 15A is a schematic diagram showing the thoracic and visceral innervations of the vagal nerves.
FIG. 15B is a schematic diagram of the medullary section of the brain.
Figure 15B:
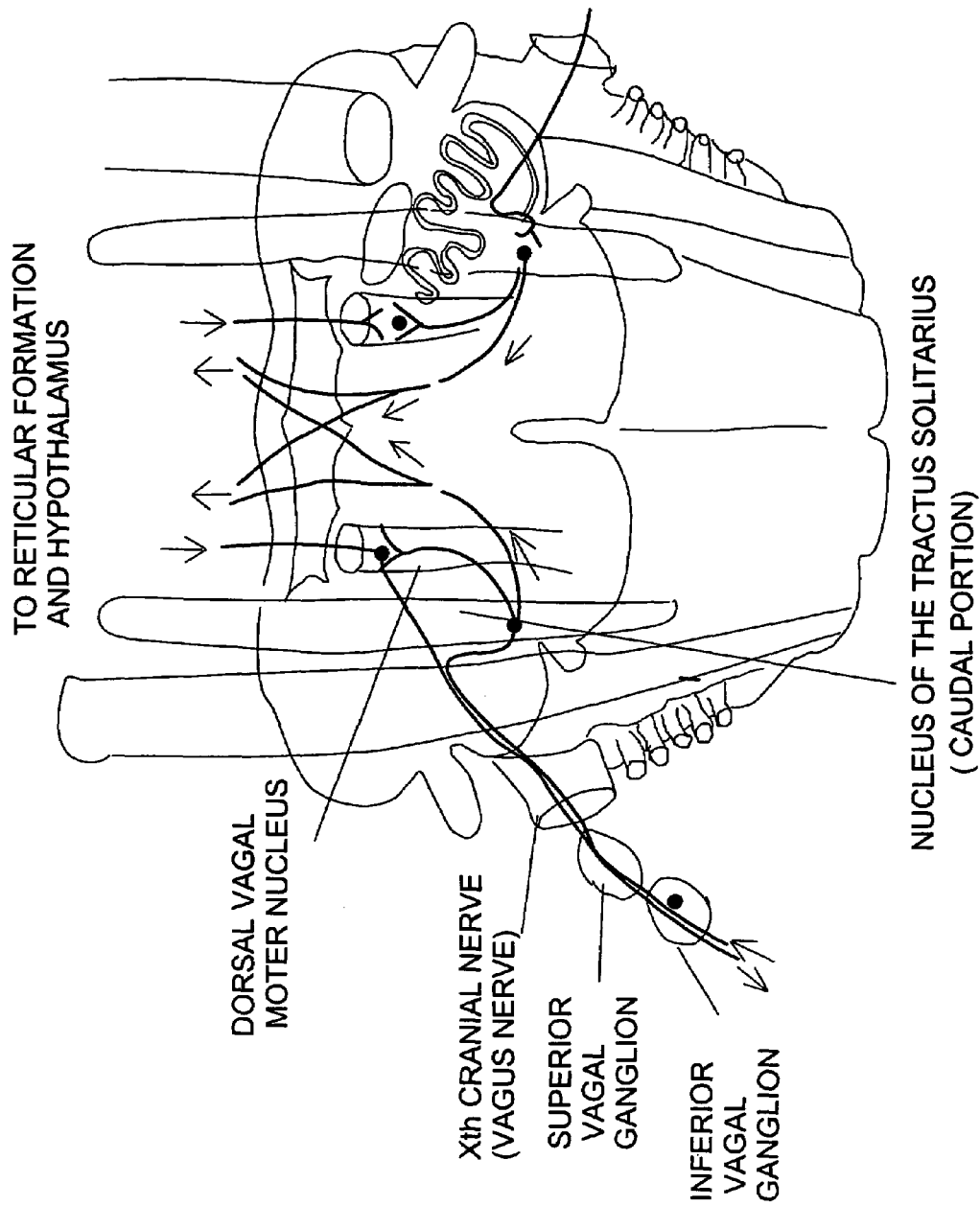
Figure 16:
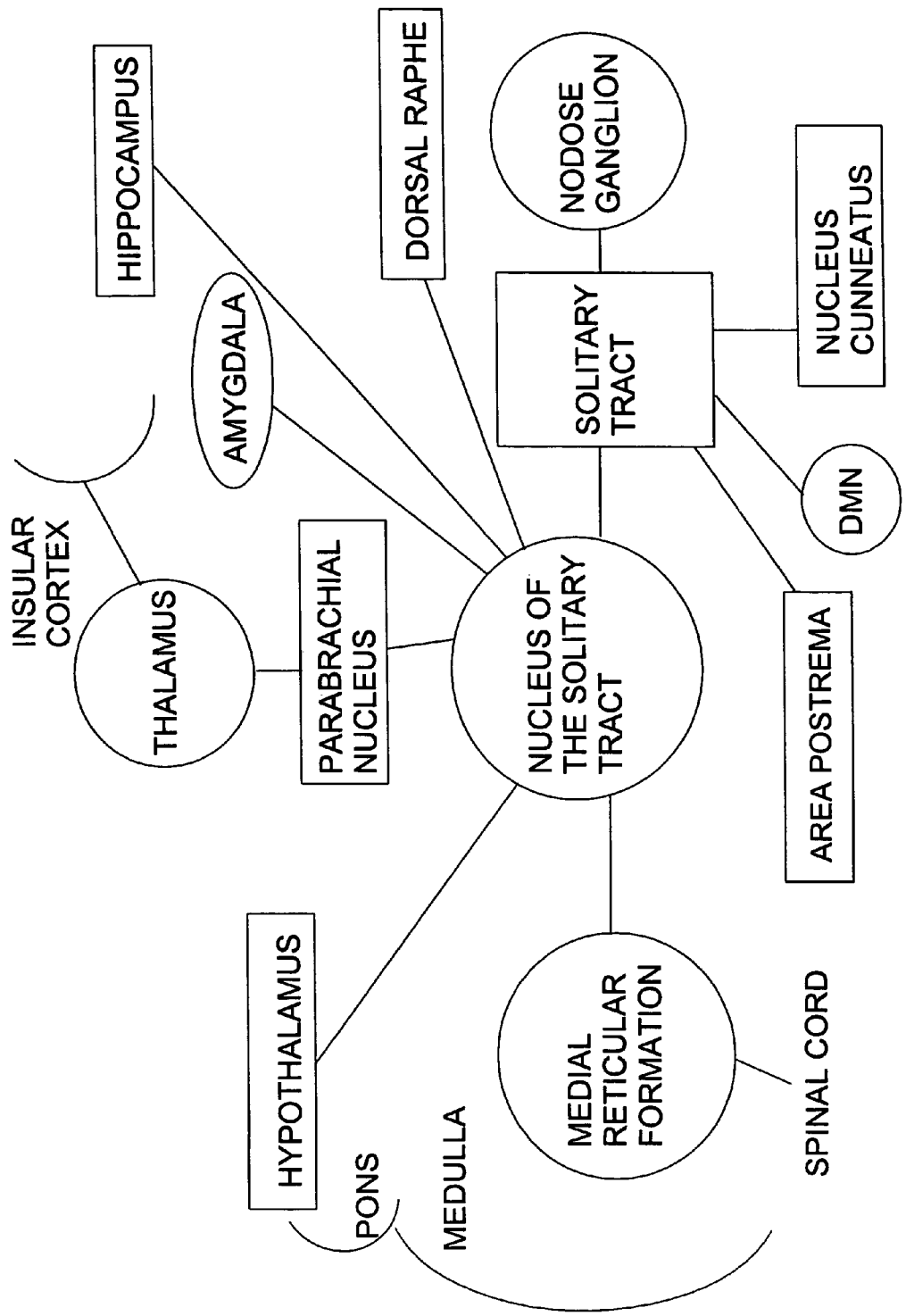
FIG. 16 is a simplified block diagram illustrating the connections of solitary tract nucleus to other centers of the brain.
Figure 17:
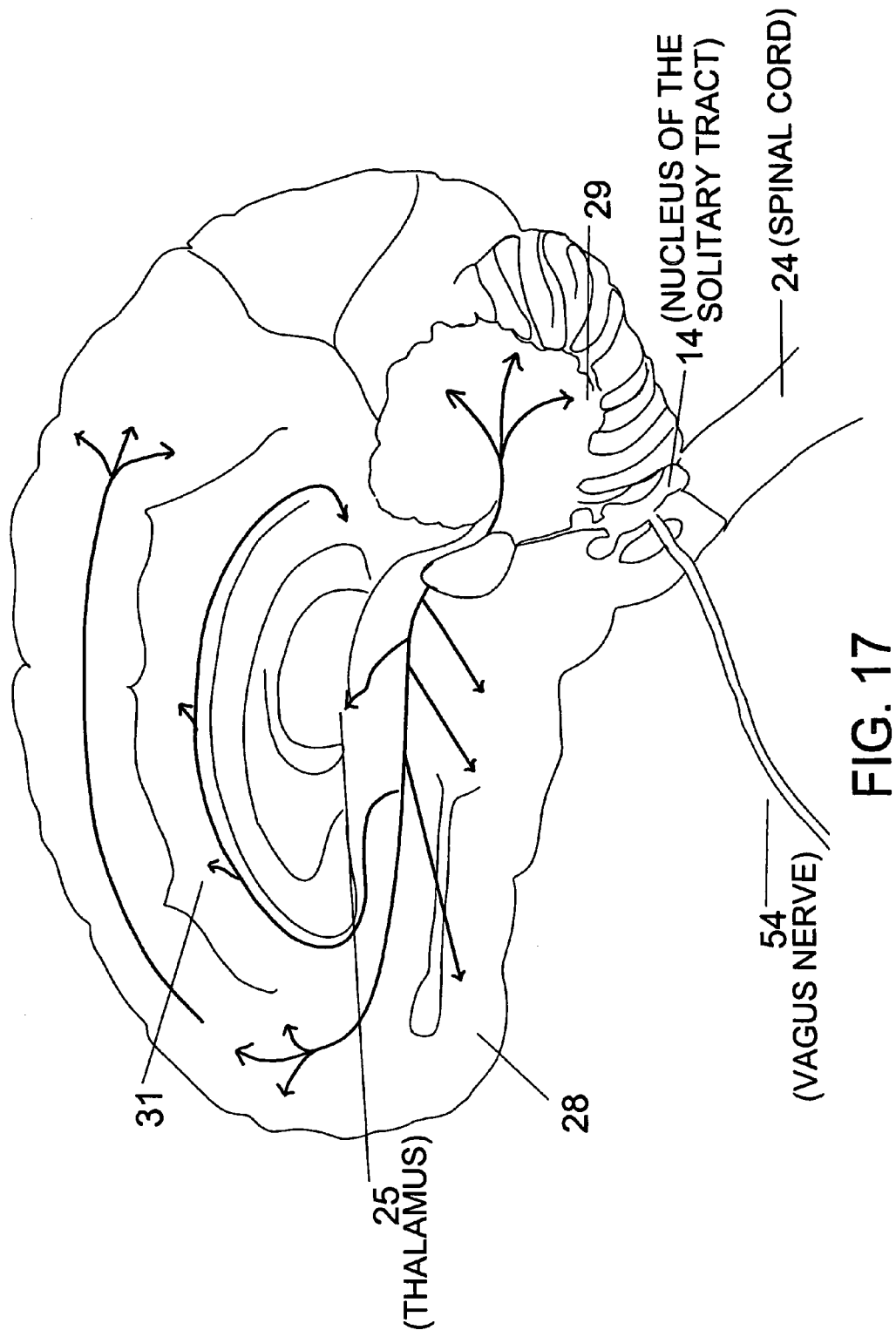
FIG. 17 is a schematic diagram of brain showing the relationship of the solitary tract nucleus to other centers of the brain.
Figure 47A:
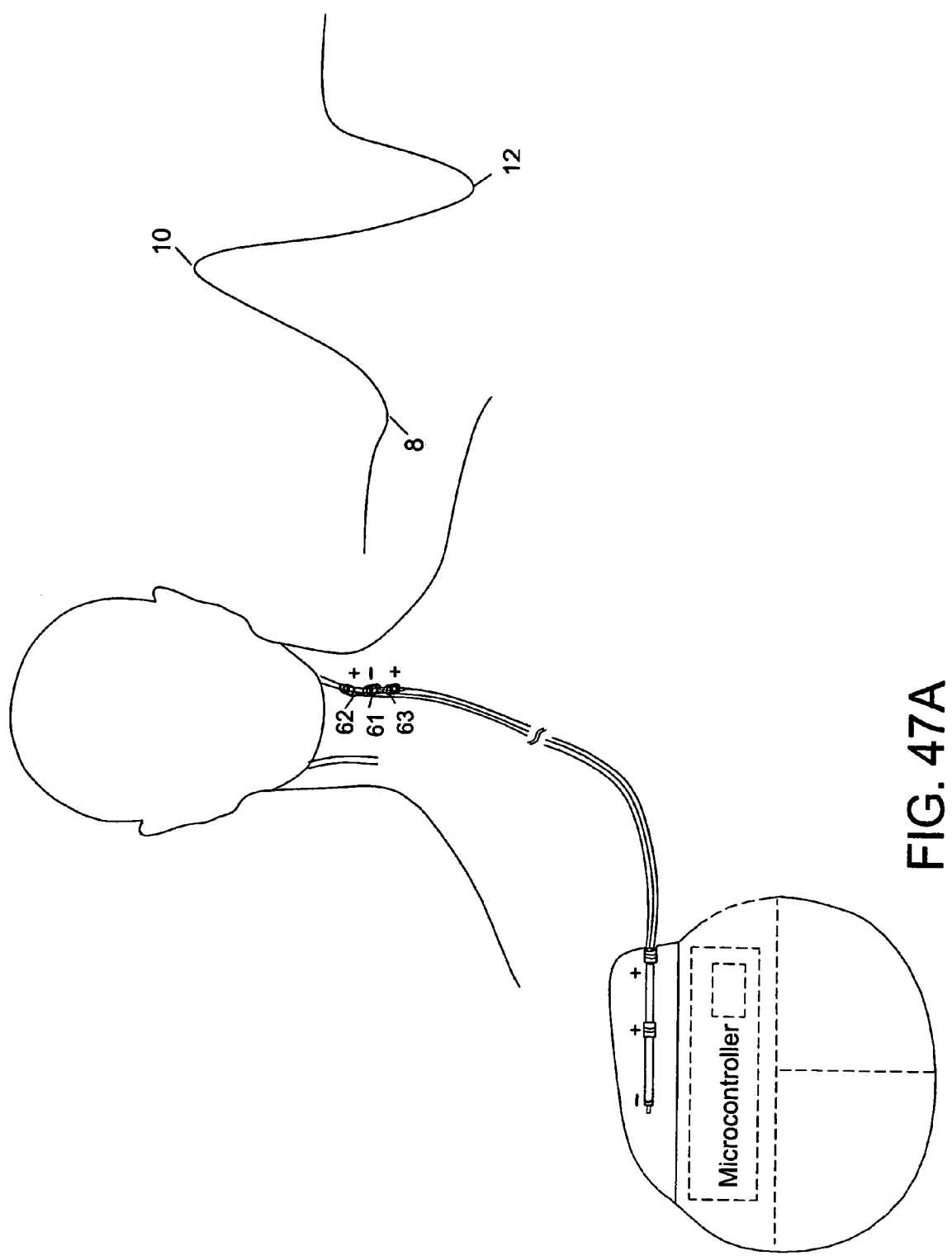
FIG. 47A depicts an implantable system with tripolar lead for selective unidirectional blocking of vagus nerve stimulation
Figure 47B:
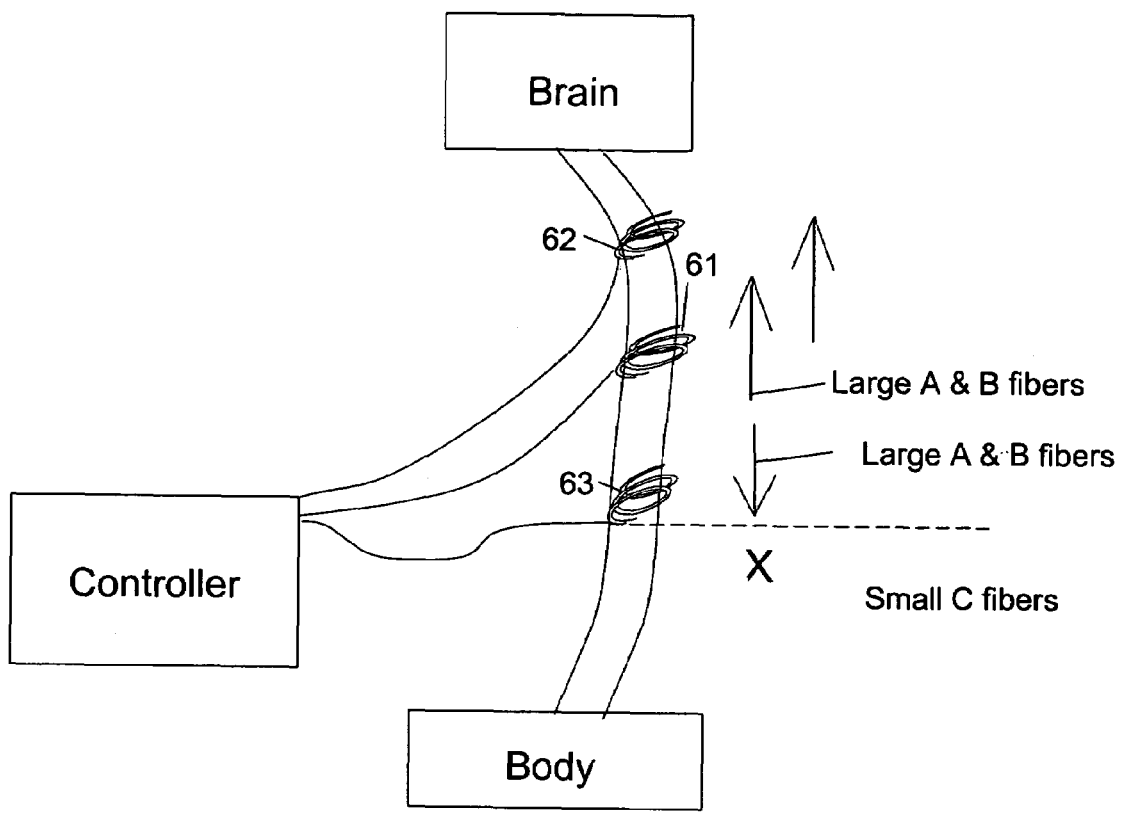
FIG. 47B depicts selective efferent blocking in the large diameter A and B fibers.
Figure 47C:
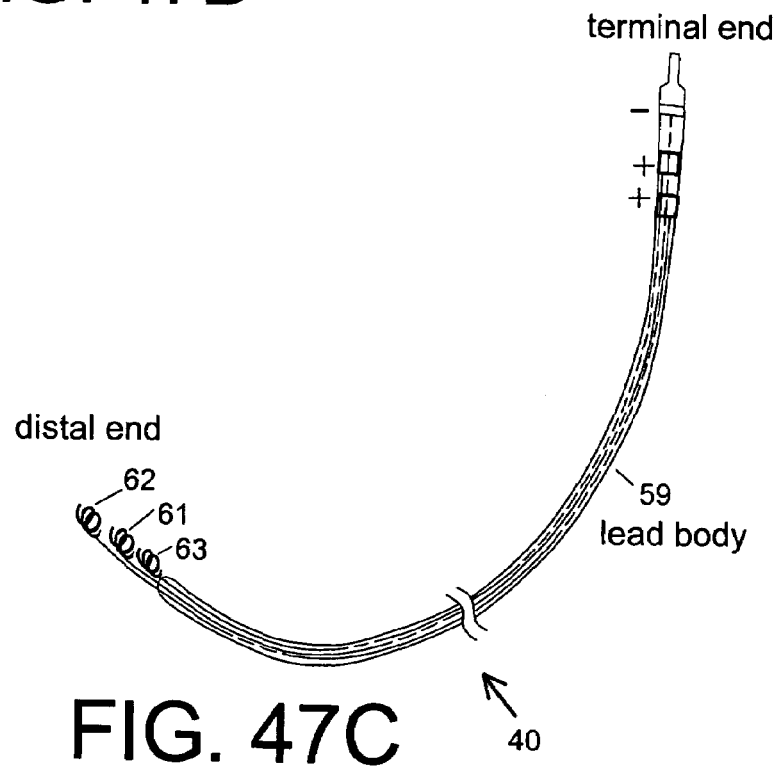
FIG. 47C is a schematic diagram of the implantable lead with three electrodes.

Since a key concept of this invention is to deliver afferent stimulation, in one aspect efferent stimulation of selected types of fibers may be substantially blocked, utilizing the "greenwave" effect. In such a case, as shown in conjunction with FIGS. 47A and 47B, a tripolar lead is utilized. As depicted on the top right portion of FIG. 47A, a depolarization peak 10 on the vagus nerve bundle corresponding to electrode 61 (cathode) and the two hyper-polarization peaks 8, 12 corresponding to electrodes 62, 63 (anodes). With the microcontroller controlling the tripolar device, the size and timing of the hyper-polarizations 8, 12 can be controlled. As was shown previously in FIGS. 2 and 10A, since the speed of conduction is different between the larger diameter A and B fibers and the smaller diameter c-fibers, by appropriately timing the pulses, collision blocks can be created for conduction via the large diameter A and B fibers in the efferent direction. This is depicted schematically in FIG. 47B. A lead with tripolar electrodes for stimulation/blocking is shown in conjunction with FIG. 47C. Alternatively, separate leads may be utilized for stimulation and blocking, and the pulse generator may be adapted for two or three leads, as is well known in the art for dual chamber cardiac pacemakers or implantable defibrillators.

Therefore in the method and system of this invention, stimulation without block may be provided. Additionally, stimulation with selective block may be provided. Blocking of nerve impulses, unidirectional blocking, and selective blocking of nerve impulses is well known in the scientific literature. Some of the general literature is listed below and is incorporated herein by reference. (a) "Generation of unidirectionally propagating action potentials using a monopolar electrode cuff", *Annals of Biomedical Engineering,* volume 14, pp. 437-450, By Ira J. Ungar et al. (b) "An asymmetric two electrode cuff for generation of unidirectionally propagated action potentials", *IEEE Transactions on Biomedical Engineering,* volume BME-33, No. 6, June 1986, By James D. Sweeney, et al. (c) A spiral nerve cuff electrode for peripheral nerve stimulation, *IEEE Transactions on Biomedical Engineering,* volume 35, No. 11, November 1988, By Gregory G. Naples. et al. (d) "A nerve cuff technique for selective excitation of peripheral nerve trunk regions, *IEEE Transactions on Biomedical Engineering,* volume 37, No. 7, July 1990, By James D. Sweeney, et al. (e) "Generation of unidirectionally propagated action potentials in a peripheral nerve by brief stimuli", *Science,* volume 206 pp. 1311-1312, Dec. 14, 1979, By Van Den Honert et al. (f) "A technique for collision block of perpheral nerve: Frequency dependence" *IEEE Transactions on Biomedical Engineering,* MP-12, volume 28, pp. 379-382, 1981, By Van Den Honert et al. (g) "A nerve cuff design for the selective activation and blocking of myelinated nerve fibers" *Ann. Conf. of the IEEE Engineering in Medicine and Biology Soc.,* volume 13, No. 2, p 906, 1991, By D. M Fitzpatrick et al. (h) "Orderly recruitment of motoneurons in an acute rabbit model", *"Ann. Conf. of the IEEE Engineering in Medicine and Biology Soc.,* volume 20, No. 5, page 2564, 1998, By N. J. M. Rijkhof, et al. (i) "Orderly stimulation of skeletal muscle motor units with tripolar nerve cuff electrode", *IEEE Transactions on Biomedical Engineering,* volume 36, No. 8, pp. 836, 1989, By R. Bratta. (j) M. Devor, "Pain Networks", Handbook of Brand Theory and Neural Networks, Ed. M. A. Arbib, MIT Press, page 698, 1998.

Blocking can be generally divided into 3 categories: (a) DC or anodal block, (b) Wedenski Block, and (c) Collision block. In anodal block there is a steady potential which is applied to the nerve causing a reversible and selective block. In Wedenski Block the nerve is stimulated at a high rate causing the rapid depletion of the neurotransmitter. In collision blocking, unidirectional action potentials are generated anti-dromically. The maximal frequency for complete block is the reciprocal of the refractory period plus the transit time, i.e. typically less than a few hundred hertz. The use of any of these blocking techniques can be applied for the practice of this invention, and all are considered within the scope of this invention.

Since one of the objects of this invention is to decrease side effects such as hoarsness in the throat, or any cardiac side effects, blocking electrodes may be strategically placed at the relevant branches of vagus nerve.

Figure 47D:
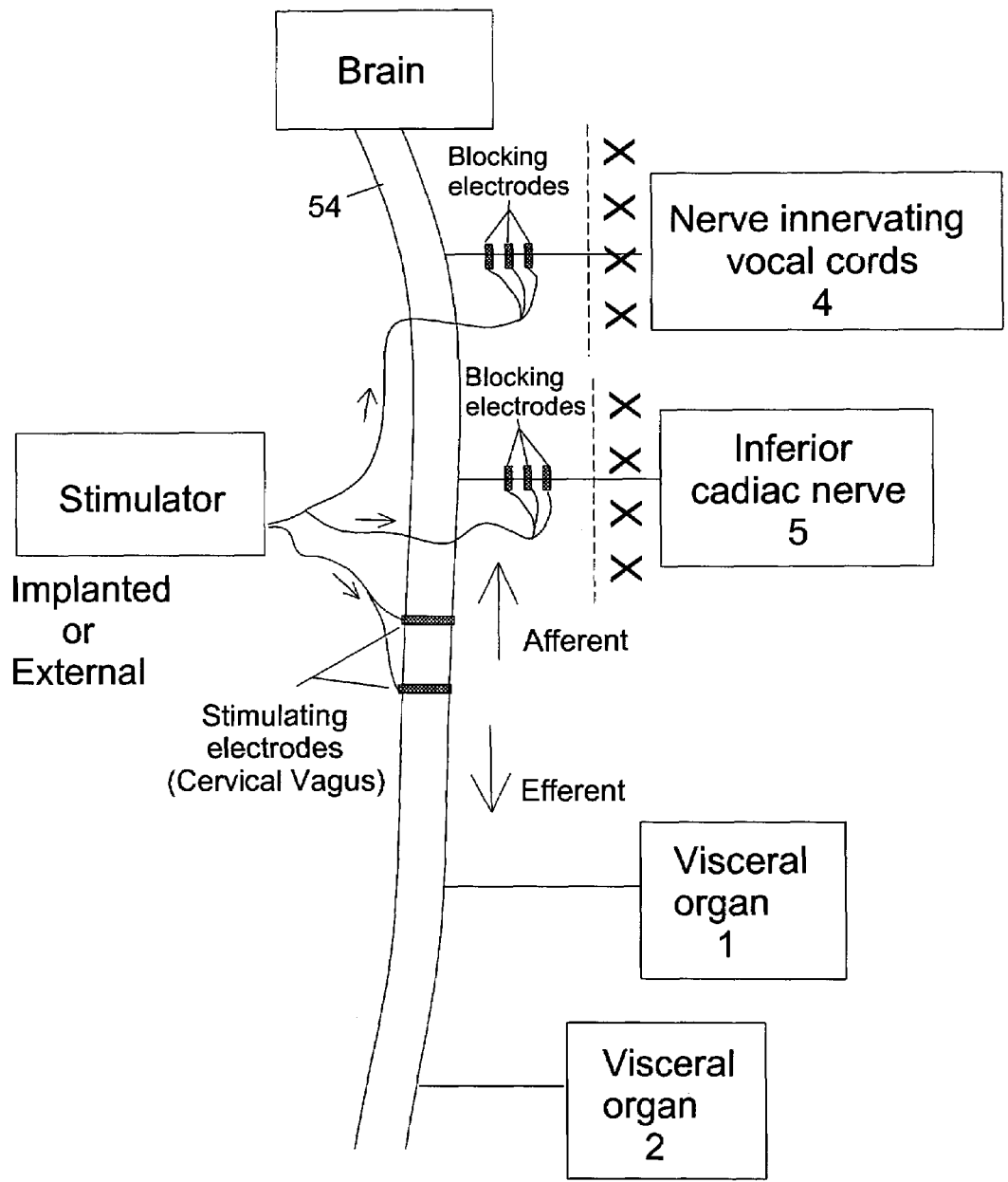
FIG. 47D is a diagram depicting electrical stimulation with conduction in the afferent direction and blocking in the efferent direction.
Figure 47F:
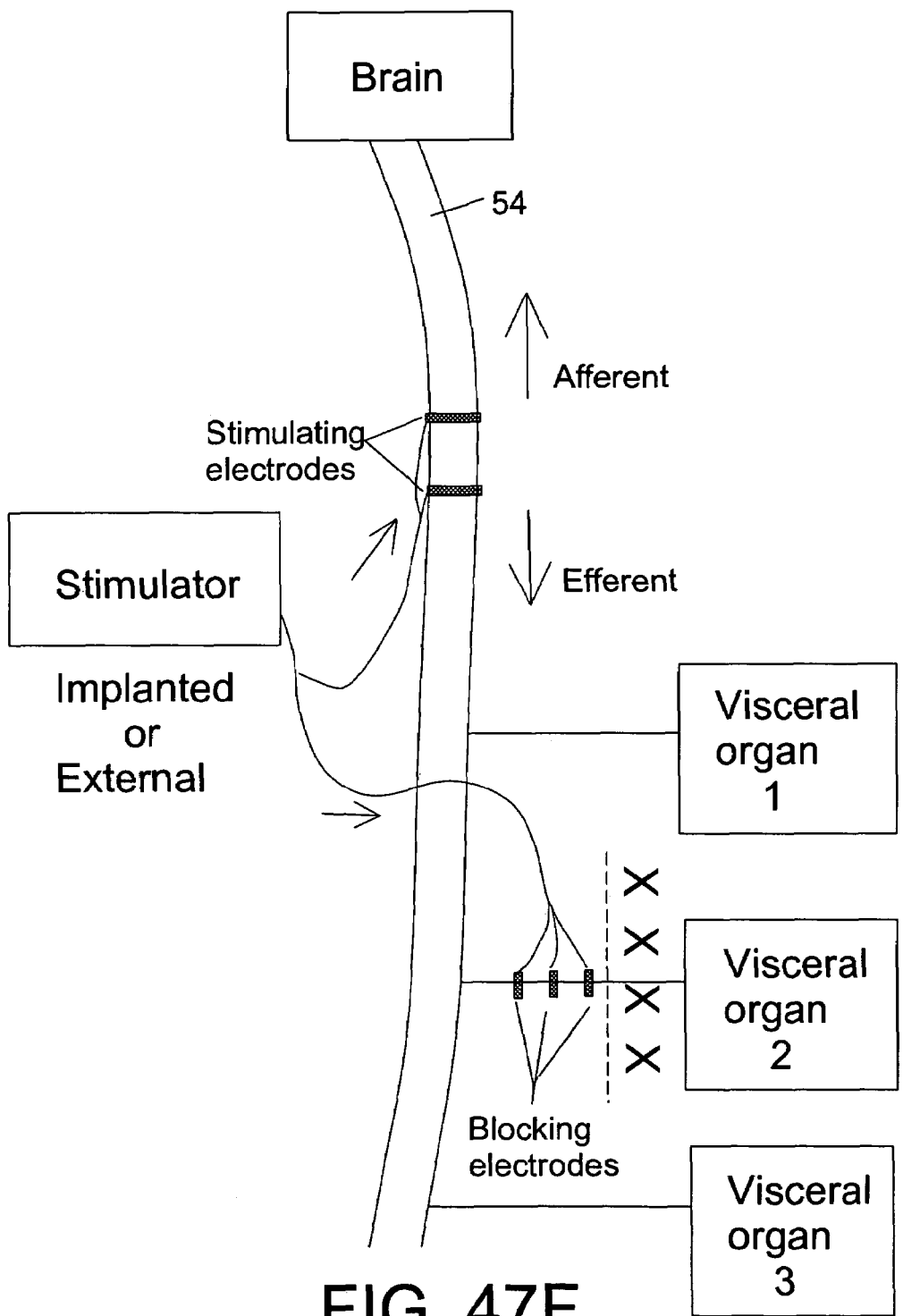
FIG. 47F is a diagram depicting electrical stimulation with conduction in the efferent direction and selective organ blocking in the afferent direction.

As shown in conjunction with FIG. 47D, the stimulating electrodes are placed on cervical vagus, and the blocking electrodes are placed on a branch to vocal cords 4. With the blocking electrodes positioned between the vocal cords and the stimulating electrodes, and the controller supplying blocking pulses to the blocking electrode, the side effects pertaining to vocal response can be eliminated or significantly diminished. Advantageously, more aggressive therapy can be provided, leading to even better efficacy. Similarly, as also depicted in FIG. 47D, the blocking electrode may be placed on the inferior cardiac nerve 5, whereby the blocking electrode would be positioned between the heart and stimulating electrode. Again, with the controller delivering blocking pulses to the blocking electrode, the cardiac side effects would be significantly diminished or virtually eliminated.

Shown in conjunction with FIG. 47E is simplified depiction of efferent block. This time with the blocking electrode placed distal to the stimulating electrode, and the controller supplying blocking pulses to the blocking electrodes, the efferent pulses can be blocked. Advantageously, the side effects related to cardiopulmonary system, gastrointestinal system and pancreobiliary system can be greatly diminished. It will be apparent to one skilled in the art that, as shown in conjunction with 47F, selective efferent block can also be performed.

Figure 48:
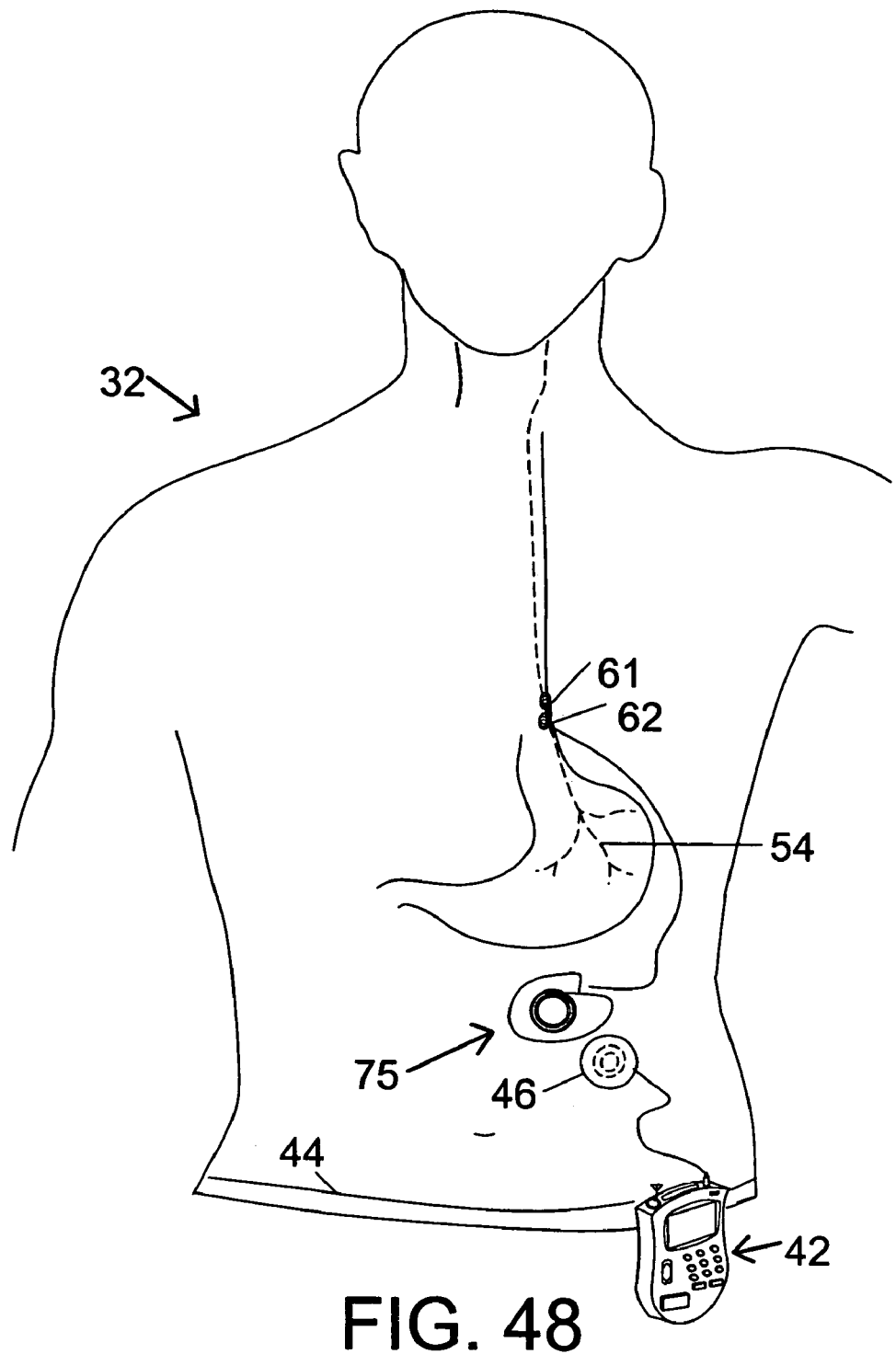
FIG. 48 depicts unilateral stimulation of vagus nerve at near the diaphram level.

In one aspect of the invention, the pulsed electrical stimulation to the vagus nerve(s) may be provided anywhere along the length of the vagus nerve(s). As was shown earlier in conjunction with FIG. 20, the pulsed electrical stimulation may be at the cervical level. Alternatively, shown in conjunction with FIG. 48, the stimulation to the vagus nerve(s) may be around the diaphramatic level. Either above the diaphragm or below the diaphragm.

The programming of the implanted pulse generator (IPG) 391 is shown in conjunction with FIGS. 49A and 49B. With the magnetic Reed Switch 389 (FIG. 38) in the closed position, a coil in the head of the programmer 85, communicates with a telemetry coil 399 of the implanted pulse generator 391. Bi-directional inductive telemetry is used to exchange data with the implanted unit 391 by means of the external programming unit 85.

Figure 50A:
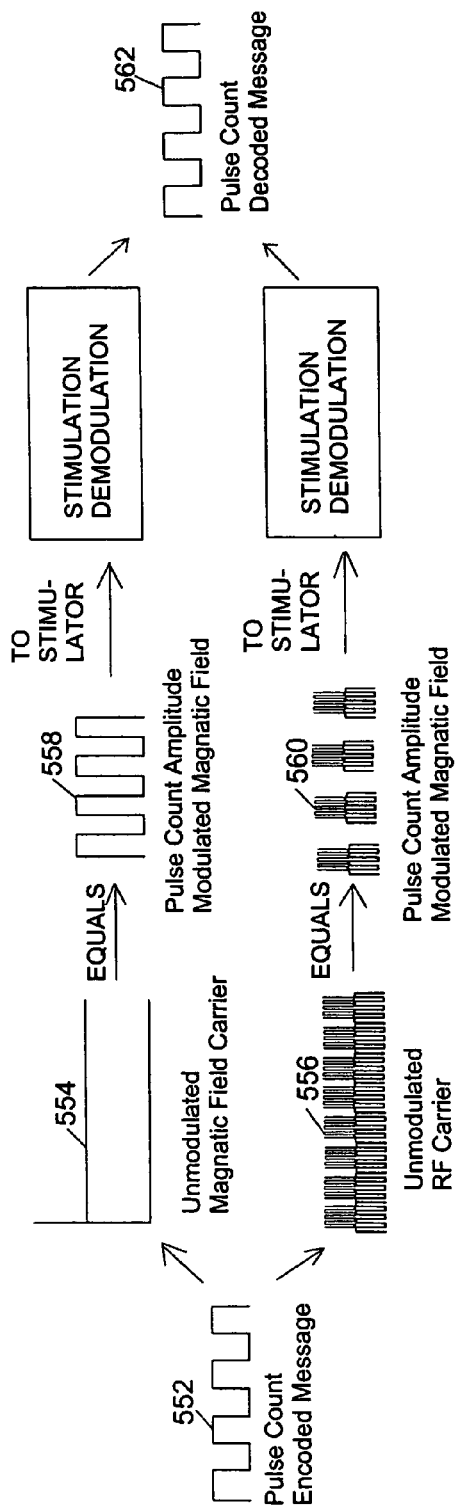
FIGS. 50A and 50B show diagrammatically encoding and decoding of programming pulses.
Figure 50B:
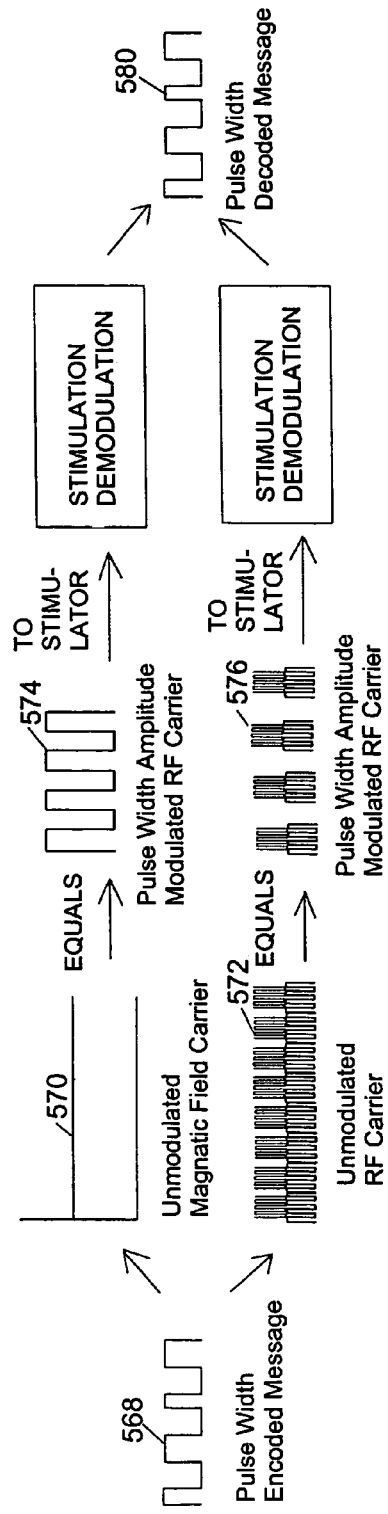

The transmission of programming information involves manipulation of the carrier signal in a manner that is recognizable by the pulse generator 391 as a valid set of instructions. The process of modulation serves as a means of encoding the programming instruction in a language that is interpretable by the implanted pulse generator 391. Modulation of signal amplitude, pulse width, and time between pulses are all used in the programming system, as will be appreciated by those skilled in the art. FIG. 50A shows an example of pulse count modulation, and FIG. 50B shows an example of pulse width modulation, that can be used for encoding.

Figure 51:
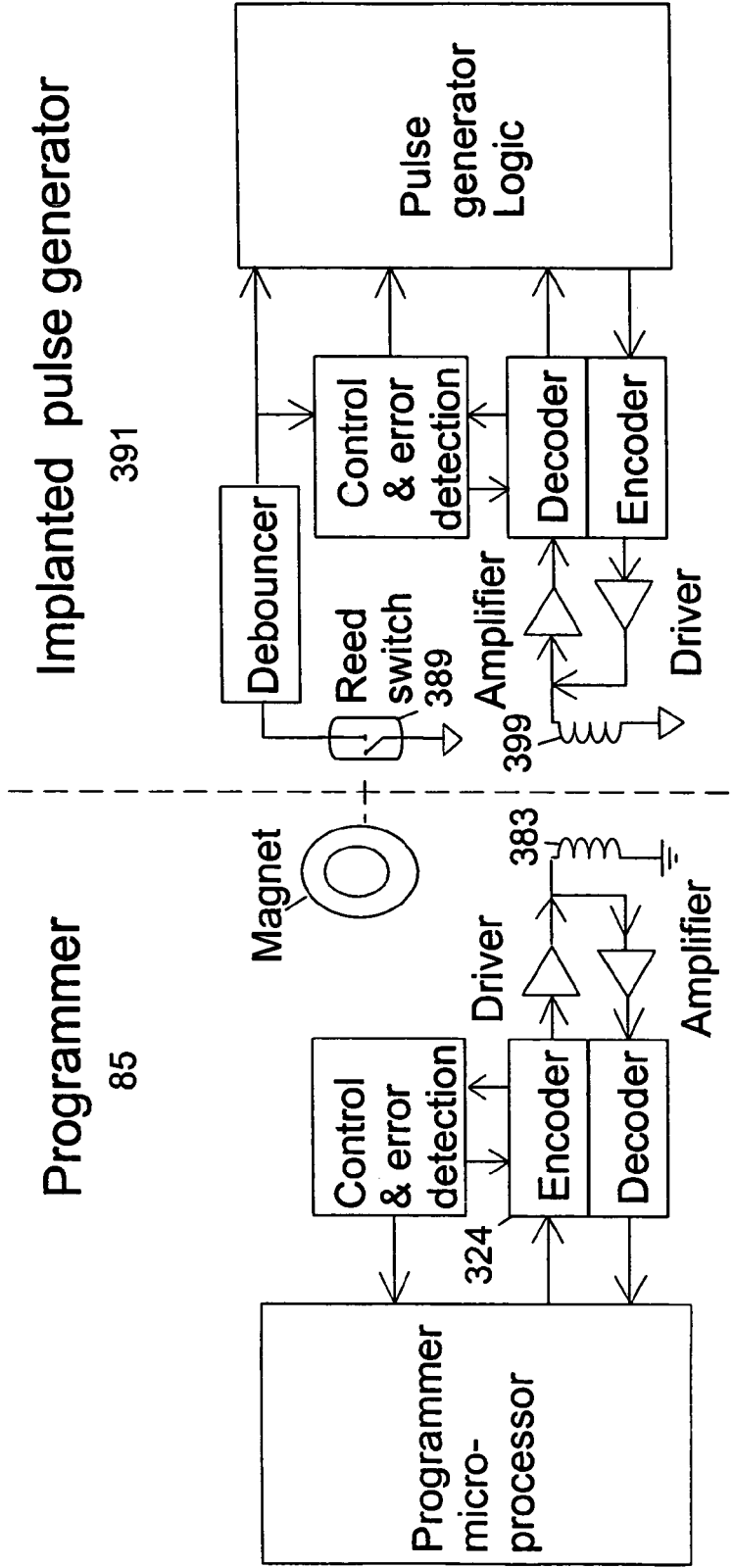
FIG. 51 is a simplified overall block diagram of implanted pulse generator (IPG) programmer.

FIG. 51 shows a simplified overall block diagram of the implanted pulse generator (IPG) 391 programming and telemetry interface. The left half of FIG. 51 is programmer 85 which communicates programming and telemetry information with the IPG 391. The sections of the IPG 391 associated with programming and telemetry are shown on the right half of FIG. 51. In this case, the programming sequence is initiated by bringing a permanent magnet in the proximity of the IPG 391 which closes a reed switch 389 in the IPG 391. Information is then encoded into a special error-correcting pulse sequence and transmitted electromagnetically through a set of coils. The received message is decoded, checked for errors, and passed on to the unit's logic circuitry. The IPG 391 of this embodiment includes the capability of bidirectional communication.

The reed switch 389 is a magnetically-sensitive mechanical switch, which consists of two thin strips of metal (the "reed") which are ferromagnetic. The reeds normally spring apart when no magnetic field is present. When a field is applied, the reeds come together to form a closed circuit because doing so creates a path of least reluctance. The programming head of the programmer contains a high-field-strength ceramic magnet.

When the switch closes, it activates the programming hardware, and initiates an interrupt of the IPG central processor. Closing the reed switch 389 also presents the logic used to encode and decode programming and telemetry signals. A nonmaskable interrupt (NMI) is sent to the IPG processor, which then executes special programming software. Since the NMI is an edge-triggered signal and the reed switch is vulnerable to mechanical bounce, a debouncing circuit is used to avoid multiple interrupts. The overall current consumption of the IPG increases during programming because of the debouncing circuit and other communication circuits.

A coil 399 is used as an antenna for both reception and transmission. Another set of coils 383 is placed in the programming head, a relatively small sized unit connected to the programmer 85. All coils are tuned to the same resonant frequency. The interface is half-duplex with one unit transmitting at a time.

Figure 52:
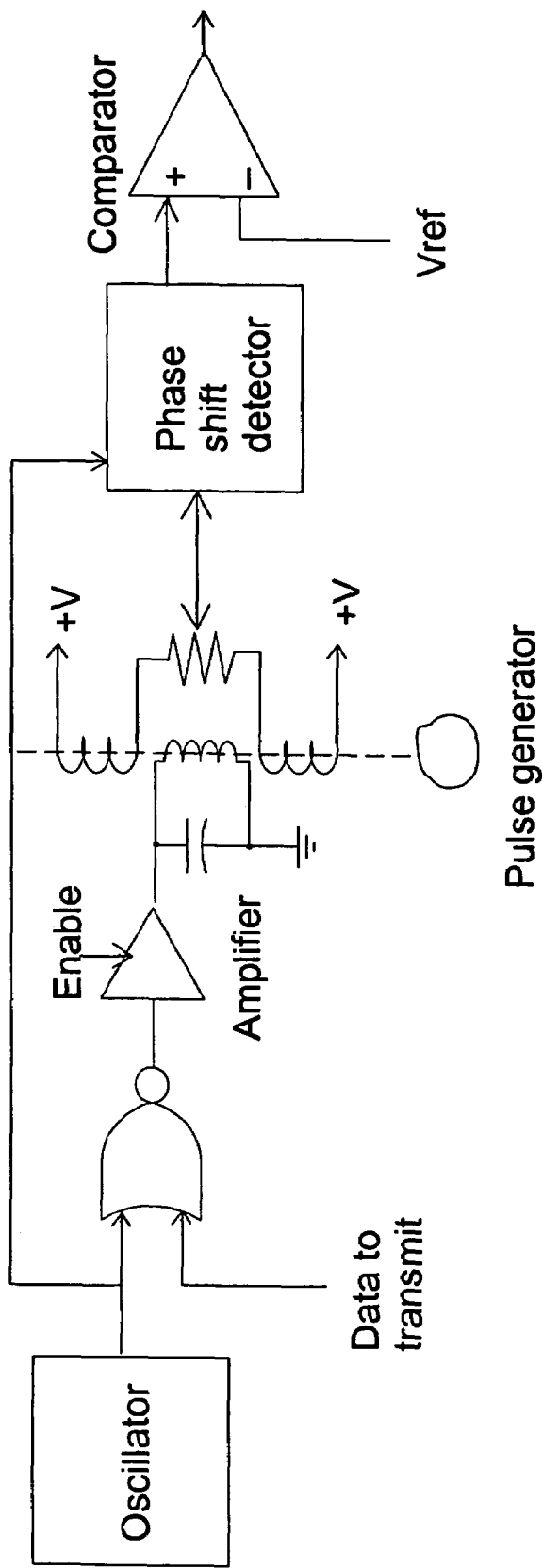
FIG. 52 shows a programmer head positioning circuit.

Since the relative positions of the programming head 87 and IPG 391 determine the coupling of the coils, this embodiment utilizes a special circuit which has been devised to aid the positioning of the programming head, and is shown in FIG. 52. It operates on similar principles to the linear variable differential transformer. An oscillator tuned to the resonant frequency of the pacemaker coil 399 drives the center coil of a three-coil set in the programmer head. The phase difference between the original oscillator signal and the resulting signal from the two outer coils is measured using a phase shift detector. It is proportional to the distance between the implanted pulse generator and the programmer head. The phase shift, as a voltage, is compared to a reference voltage and is then used to control an indicator such as an LED. An enable signal allows switching the circuit on and off.

Figure 53:
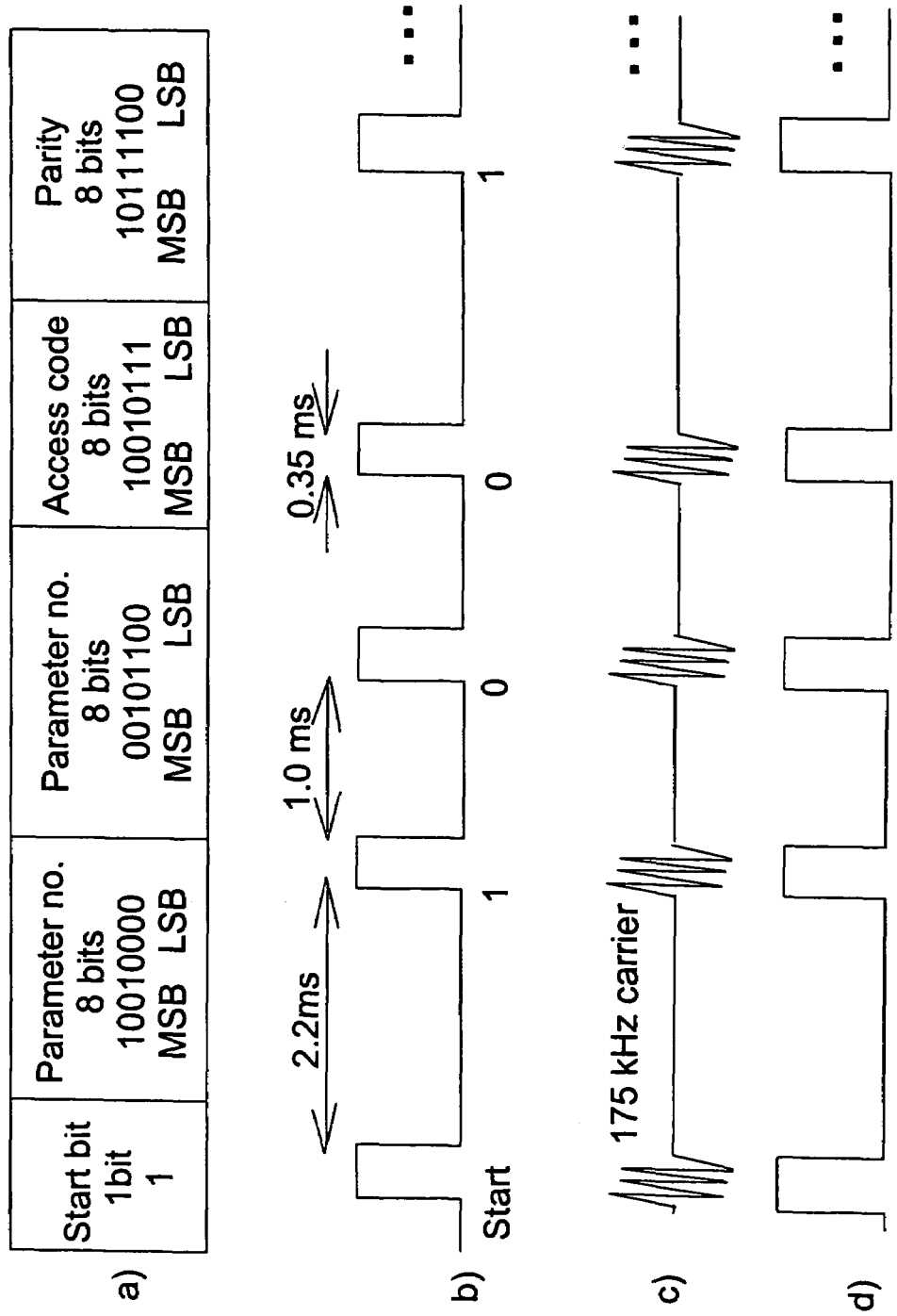
FIG. 53 depicts typical encoding and modulation of programming messages.
Figure 54:
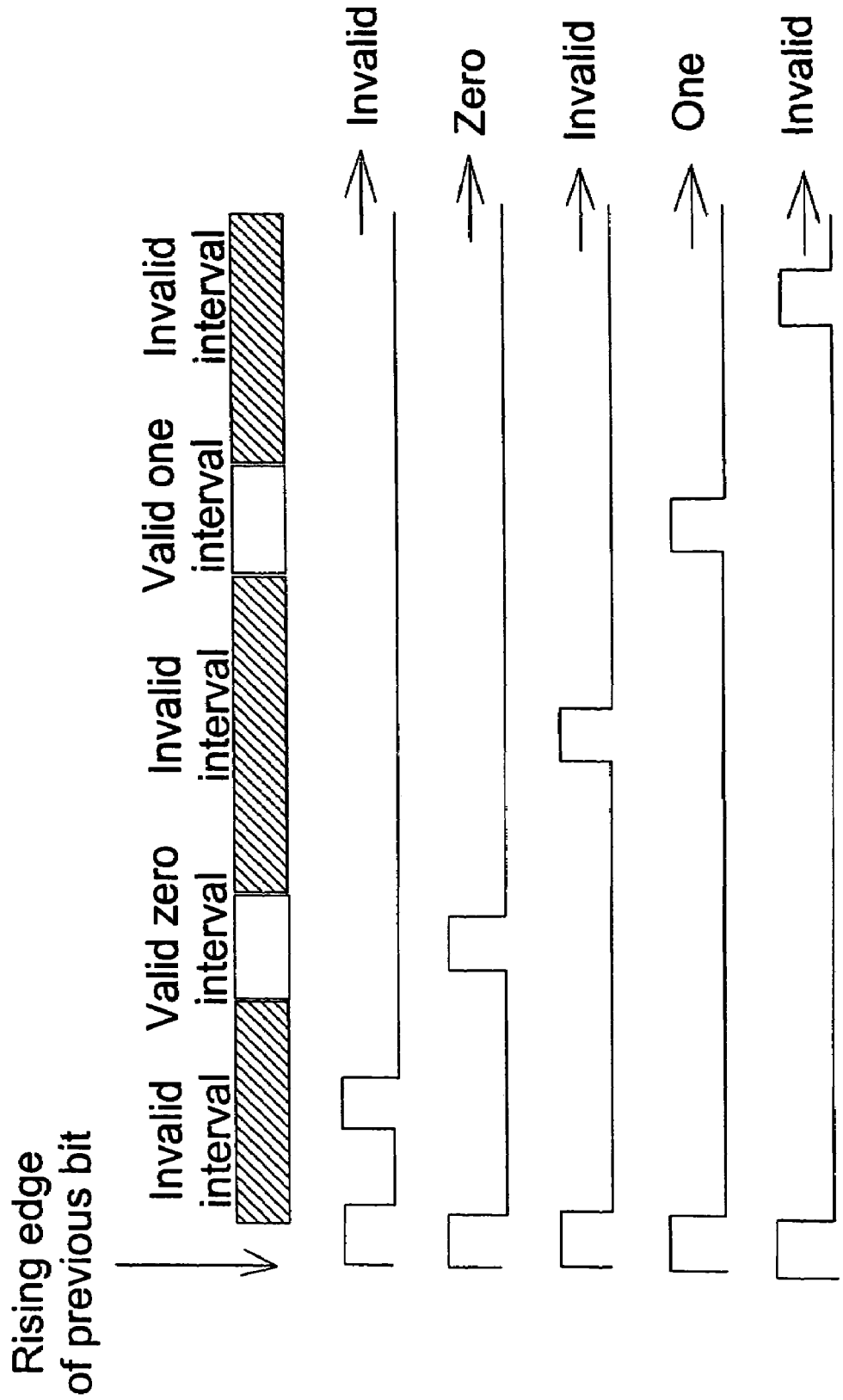
FIG. 54 shows decoding one bit of the signal from FIG. 53.

Actual programming is shown in conjunction with FIGS. 53 and 54. Programming and telemetry messages comprise many bits; however, the coil interface can only transmit one bit at a time. In addition, the signal is modulated to the resonant frequency of the coils, and must be transmitted in a relatively short period of time, and must provide detection of erroneous data.

A programming message is comprised of five parts FIG. 53(a). The start bit indicates the beginning of the message and is used to synchronize the timing of the rest of the message. The parameter number specifies which parameter (e.g., mode, pulse width, delay) is to be programmed. In the example, in FIG. 53(a) the number 10010000 specifies the pulse rate to be specified. The parameter value represents the value that the parameter should be set to. This value may be an index into a table of possible values; for example, the value 00101100 represents a pulse stimulus rate of 80 pulses/min. The access code is a fixed number based on the stimulus generator model which must be matched exactly for the message to succeed. It acts as a security mechanism against use of the wrong programmer, errors in the message, or spurious programming from environmental noise. It can also potentially allow more than one programmable implant in the patient. Finally, the parity field is the bitwise exclusive-OR of the parameter number and value fields. It is one of several error-detection mechanisms.

All of the bits are then encoded as a sequence of pulses of 0.35-ms duration FIG. 53(b). The start bit is a single pulse. The remaining bits are delayed from their previous bit according to their bit value. If the bit is a zero, the delay is short (1.0); if it is a one, the delay is long (2.2 ms). This technique of pulse position coding, makes detection of errors easier.

The serial pulse sequence is then amplitude modulated for transmission FIG. 53(c). The carrier frequency is the resonant frequency of the coils. This signal is transmitted from one set of coils to the other and then demodulated back into a pulse sequence FIG. 53(d).

FIG. 54 shows how each bit of the pulse sequence is decoded from the demodulated signal. As soon as each bit is received, a timer begins timing the delay to the next pulse. If the pulse occurs within a specific early interval, it is counted as a zero bit (FIG. 54(b)). If it otherwise occurs with a later interval, it is considered to be a one bit (FIG. 54(d)). Pulses that come too early, too late, or between the two intervals are considered to be errors and the entire message is discarded (FIG. 54(a, c, e)). Each bit begins the timing of the bit that follows it. The start bit is used only to time the first bit.

Telemetry data may be either analog or digital. Digital signals are first converted into a serial bit stream using an encoding such as shown in FIG. 54(b). The serial stream or the analog data is then frequency modulated for transmission.

An advantage of this and other encodings is that they provide multiple forms of error detection. The coils and receiver circuitry are tuned to the modulation frequency, eliminating noise at other frequencies. Pulse-position coding can detect errors by accepting pulses only within narrowly-intervals. The access code acts as a security key to prevent programming by spurious noise or other equipment. Finally, the parity field and other checksums provides a final verification that the message is valid. At any time, if an error is detected, the entire message is discarded.

Another more sophisticated type of pulse position modulation may be used to increase the bit transmission rate. In this, the position of a pulse within a frame is encoded into one of a finite number of values, e.g. 16. A special synchronizing bit is transmitted to signal the start of the frame. Typically, the frame contains a code which specifies the type or data contained in the remainder of the frame.

FIG. 55 shows a diagram of receiving and decoding circuitry for programming data. The IPG coil, in parallel with capacitor creates a tuned circuit for receiving data. The signal is band-pass filtered 602 and envelope detected 604 to create the pulsed signal in FIG. 53(d). After decoding, the parameter value is placed in a RAM at the location specified by the parameter number. The IPG can have two copies of the RAM—a permanent set and a temporary set—which makes it easy for the physician to set the IPG to a temporary configuration and later reprogram it back to the usual settings.

FIG. 56 shows the basic circuit used to receive telemetry data. Again, a coil and capacitor create a resonant circuit tuned to the carrier frequency. The signal is further band-pass filtered 614 and then frequency-demodulated using a phase-locked loop 618.

Figure 57:
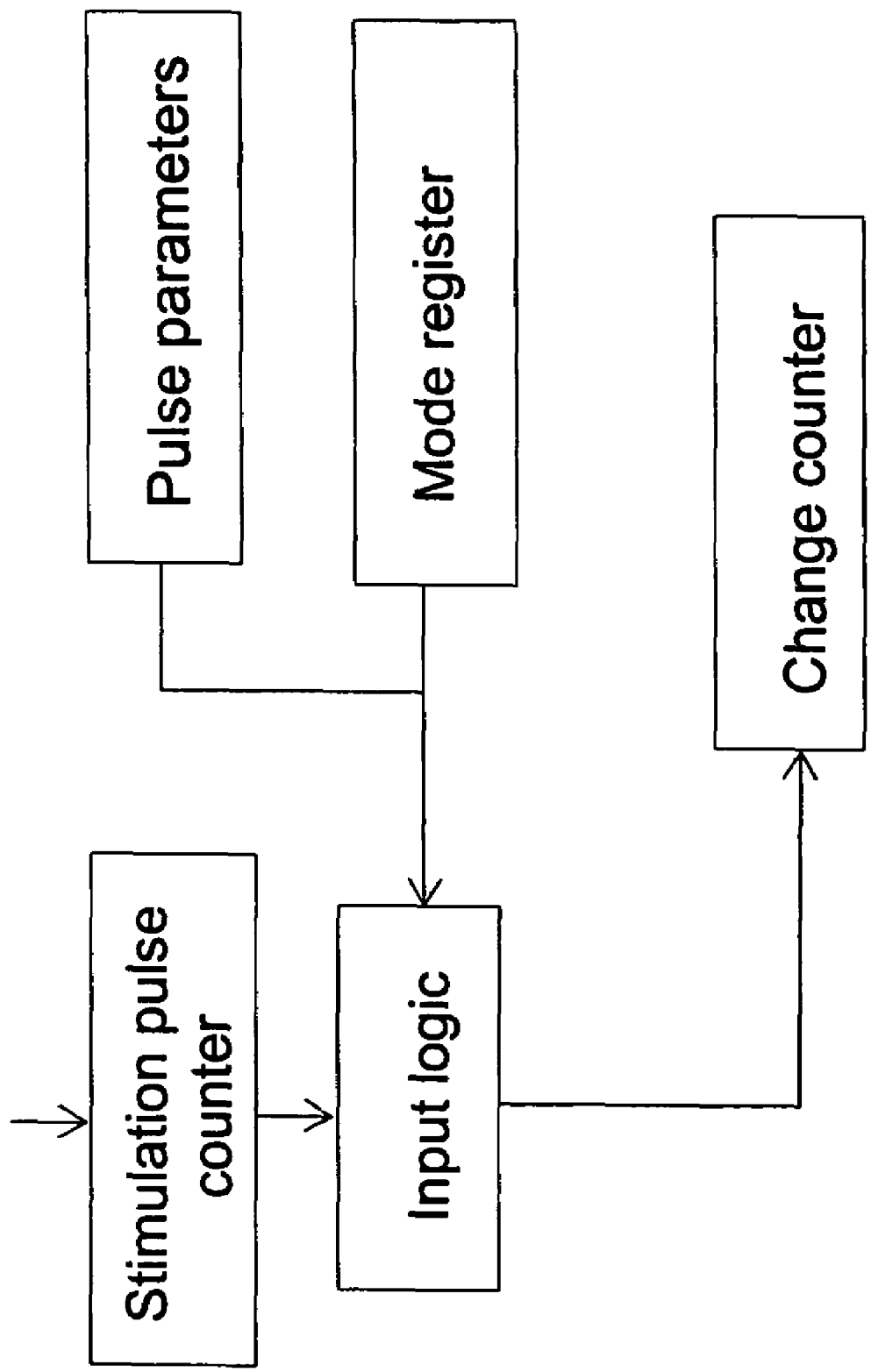
FIG. 57 is a block diagram of a battery status test circuit.

This embodiment also comprises an optional battery status test circuit. Shown in conjunction with FIG. 57, the charge delivered by the battery is estimated by keeping track of the number of pulses delivered by the IPG 391. An internal charge counter is updated during each test mode to read the total charge delivered. This information about battery status is read from the IPG 391 via telemetry.

Combination Implantable Device Comprising both a Stimulus-Receiver and a Programmable Implantable Pulse Generator (IPG)

In one embodiment, the implantable device may comprise both a stimulus-receiver and a programmable implantable pulse generator (IPG) in one device. This embodiment also comprises fixed pre-determined/pre-packaged programs. Examples of LOW, LOW-MED, MED, and HIGH stimulation states were given in the previous section, under "Programmer-less Implantable Pulse Generator (IPG)". These pre-packaged/pre-determined programs comprise unique combinations of pulse amplitude, pulse width, pulse frequency, ON-time and OFF-time.

Figure 58:
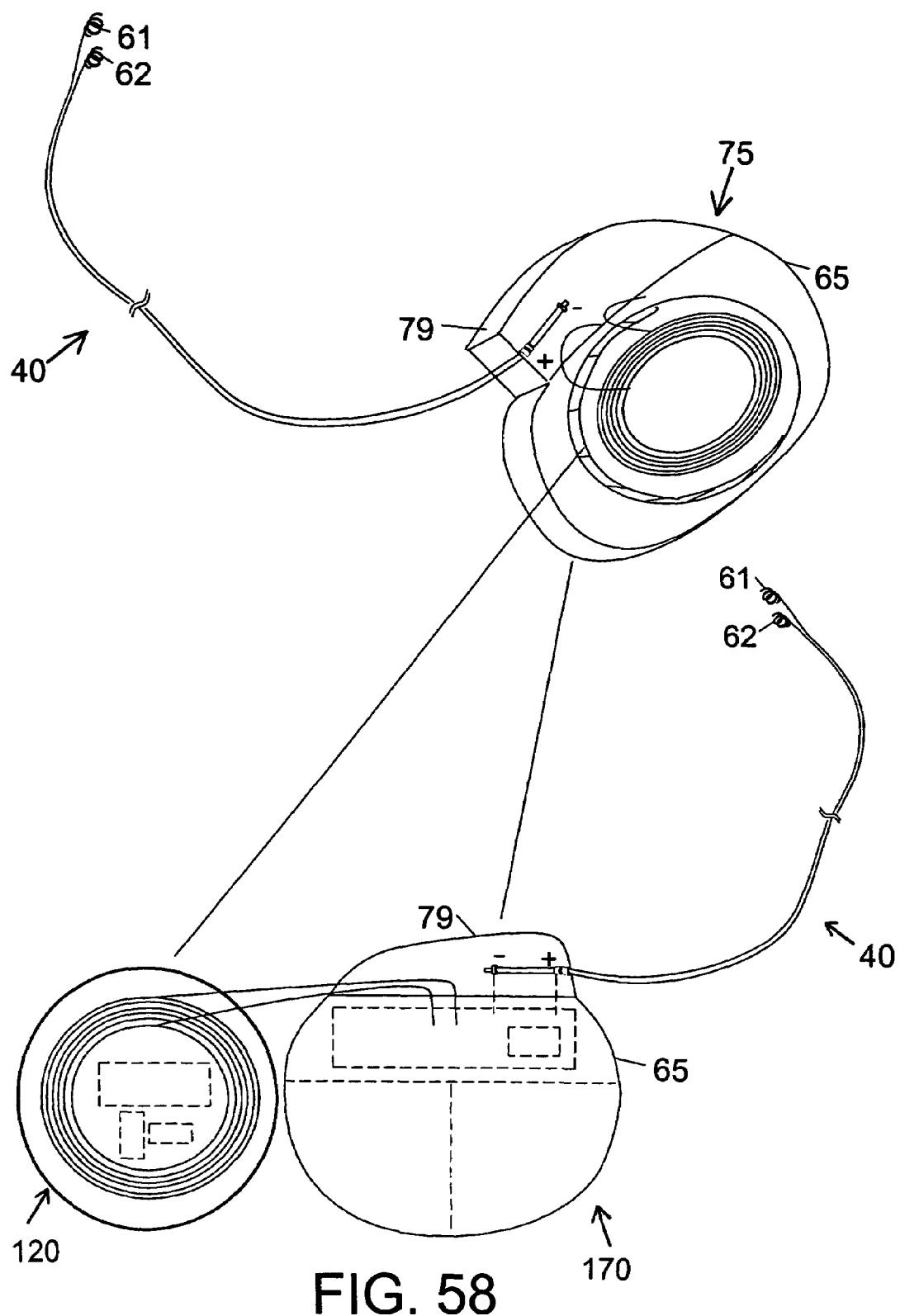
FIG. 58 is a diagram showing the two modules of the implanted pulse generator (IPG).

FIG. 58 shows a close up view of the packaging of the implanted stimulator 75 of this embodiment, showing the two subassemblies 120, 170. The two subassemblies are the stimulus-receiver module 120 and the battery operated pulse generator module 170. The electrical components of the stimulus-receiver module 120 may be substantially in the, titanium case along with other circuitry, except for a coil. The coil may be outside the titanium case as shown in FIG. 58, or the coil 48C may be externalized at the header portion 79 of the implanted device, and may be wrapped around the titanium can. In this case, the coil is encased in the same material as the header 79, as shown in FIGS. 59A-59D. FIG. 59A depicts a bipolar configuration with two separate feed-throughs, 56, 58. FIG. 59B depicts a unipolar configuration with one separate feed-through 66. FIG. 59C, and 59D depict the same configuration except the feed-throughs are common with the feed-throughs 66A for the lead.

Figure 60:
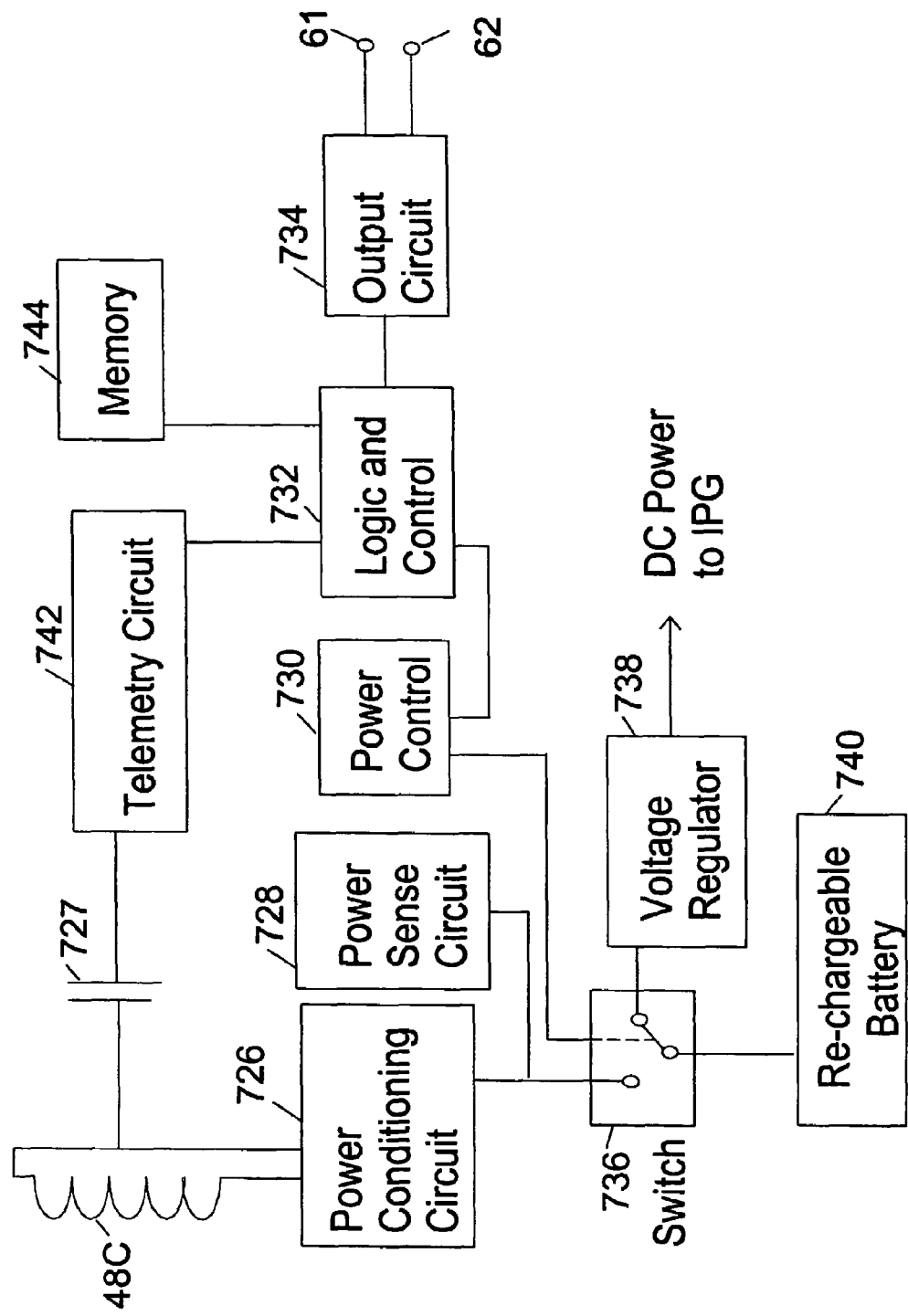
FIG. 60 shows a block diagram of an implantable stimulator which can be used as a stimulus-receiver or an implanted pulse generator with rechargeable battery.

FIG. 60 is a simplified overall block diagram of the embodiment where the implanted stimulator 75 is a combination device, which may be used as a stimulus-receiver (SR) in conjunction with an external stimulator, or the same implanted device may be used as a traditional programmable implanted pulse generator (IPG). The coil 48C which is external to the titanium case may be used both as a secondary of a stimulus-receiver, or may also be used as the forward and back telemetry coil.

In this embodiment, as disclosed in FIG. 60, the IPG circuitry within the titanium case is used for all stimulation pulses whether the energy source is the internal battery 740 or an external power source. The external device serves as a source of energy, and as a programmer that sends telemetry to the IPG. For programming, the energy is sent as high frequency sine waves with superimposed telemetry wave driving the external coil 46C. Once received by the implanted coil 48C, the telemetry is passed through coupling capacitor 727 to the IPG's telemetry circuit 742. For pulse delivery using external power source, the stimulus-receiver portion will receive the energy coupled to the implanted coil 48C and, using the power conditioning circuit 726, rectify it to produce DC, filter and regulate the DC, and couple it to the IPG's voltage regulator 738 section so that the IPG can run from the externally supplied energy rather than the implanted battery 740.

The system provides a power sense circuit 728 that senses the presence of external power communicated with the power control 730 when adequate and stable power is available from an external source. The power control circuit controls a switch 736 that selects either battery power 740 or conditioned external power from 726. The logic and control section 732 and memory 744 includes the IPG's microcontroller, pre-programmed instructions, and stored changeable parameters. Using input for the telemetry circuit 742 and power control 730, this section controls the output circuit 734 that generates the output pulses.

Figure 61:
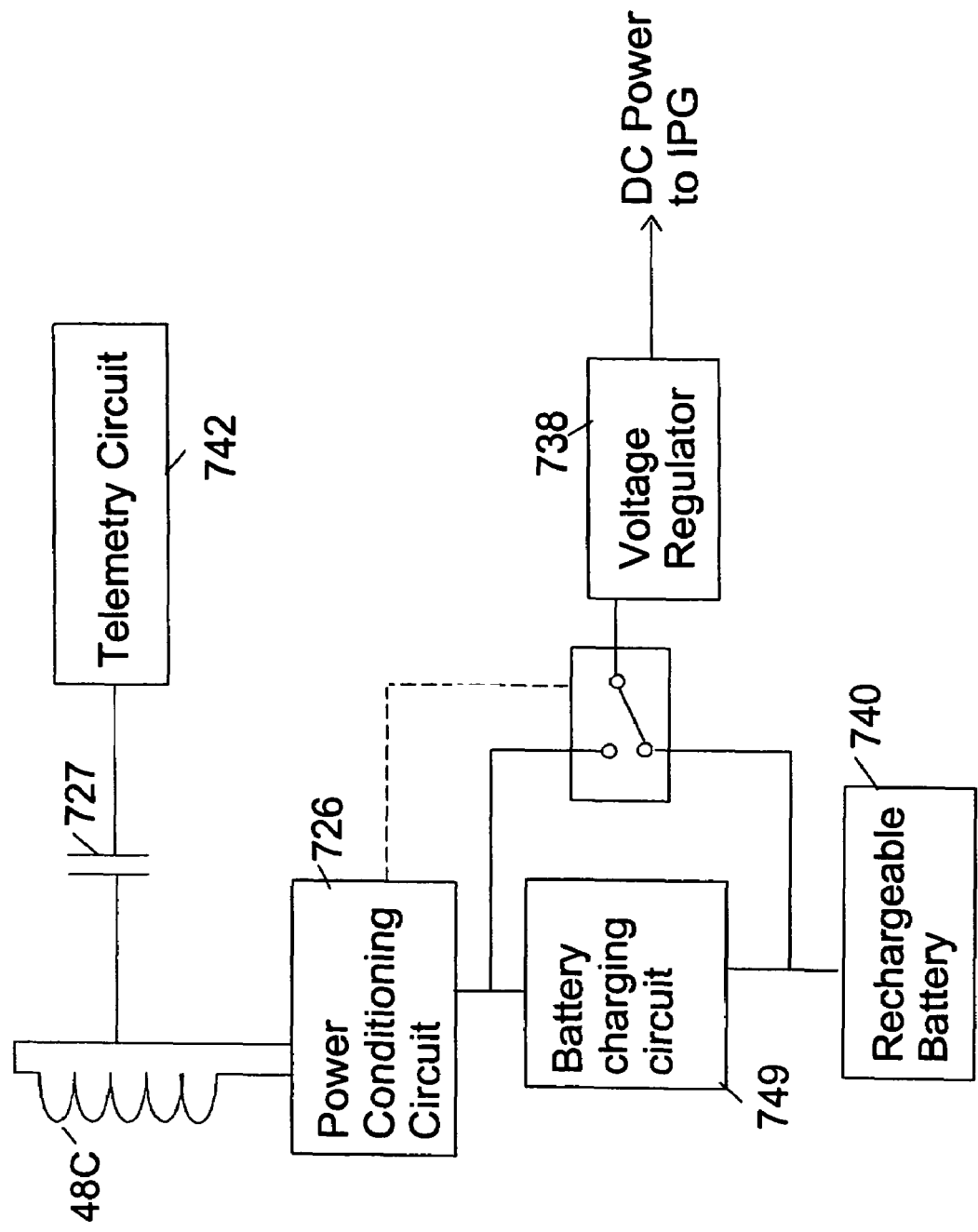
FIG. 61 is a block diagram highlighting battery charging circuit of the implantable stimulator of FIG. 60.

It will be clear to one skilled in the art that this embodiment of the invention can also be practiced with a rechargeable battery. This version is shown in conjunction with FIG. 61. The circuitry in the two versions are similar except for the battery charging circuitry 749. This circuit is energized when external power is available. It senses the charge state of the battery and provides appropriate charge current to safely recharge the battery without overcharging.

Figure 62:
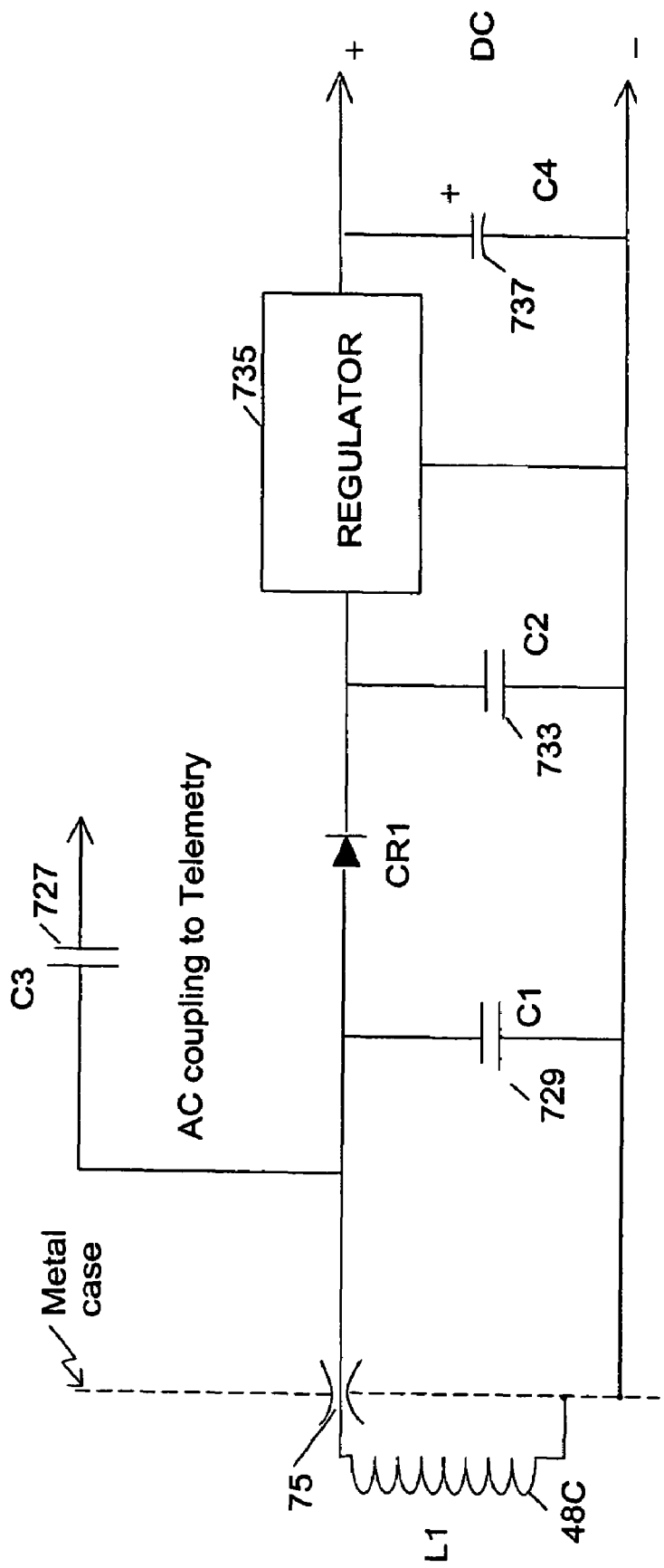
FIG. 62 is a schematic diagram highlighting stimulus-receiver portion of implanted stimulator of one embodiment.

The stimulus-receiver portion of the circuitry is shown in conjunction with FIG. 62. Capacitor C1 (729) makes the combination of C1 and L1 sensitive to the resonant frequency and less sensitive to other frequencies, and energy from an external (primary) coil 46C is inductively transferred to the implanted unit via the secondary coil 48C. The AC signal is rectified to DC via diode 731, and filtered via capacitor 733. A regulator 735 sets the output voltage and limits it to a value just above the maximum IPG cell voltage. The output capacitor C4 (737), typically a tantalum capacitor with a value of 100 micro-Farads or greater, stores charge so that the circuit can supply the IPG with high values of current for a short time duration with minimal voltage change during a pulse while the current draw from the external source remains relatively constant. Also shown in conjunction with FIG. 62, a capacitor C3 (727) couples signals for forward and back telemetry.

FIGS. 63A and 63B show alternate connection of the receiving coil. In FIG. 63A, each end of the coil is connected to the circuit through a hermetic feedthrough filter. In this instance, the DC output is floating with respect to the IPG's case. In FIG. 63B, one end of the coil is connected to the exterior of the IPG's case. The circuit is completed by connecting the capacitor 729 and bridge rectifier 739 to the interior of the IPG's case The advantage of this arrangement is that it requires one less hermetic feedthrough filter, thus reducing the cost and improving the reliability of the IPG. Hermetic feedthrough filters are expensive and a possible failure point. However, the case connection may complicit the output circuitry or limit its versatility. When using a bipolar-electrode, care must be taken to prevent an unwanted return path for the pulse to the IPG's case. This is not a concern for unipolar pulses using a single conductor electrode because it relies on the IPG's case a return for the pulse current.

In the unipolar configuration, advantageously a bigger tissue area is stimulated since the difference between the tip (cathode) and case (anode) is larger. Stimulation using both configuration is considered within the scope of this invention.

Figure 64:
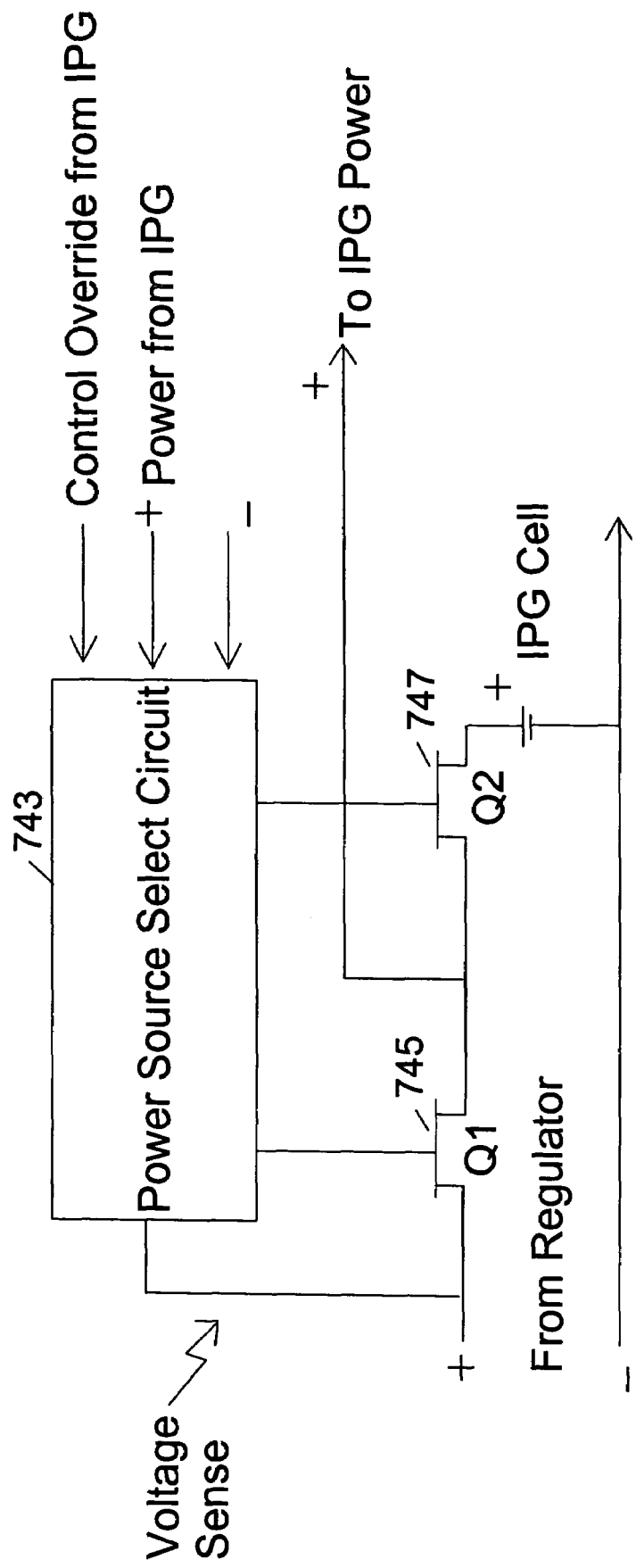
FIG. 64 depicts power source select circuit.

The power source select circuit is highlighted in conjunction with FIG. 64. In this embodiment, the IPG provides stimulation pulses according to the stimulation programs stored in the memory 744 of the implanted stimulator, with power being supplied by the implanted battery 740. When stimulation energy from an external stimulator is inductively received via secondary coil 48C, the power source select circuit (shown in block 743) switches power via transistor Q1 745 and transistor Q2 743. Transistor Q1 and Q2 are preferably low loss MOS transistor used as switches, even though other types of transistors may be used.

Implantable Pulse Generator (IPG) Comprising a Rechargable Battery

Figure 65A:
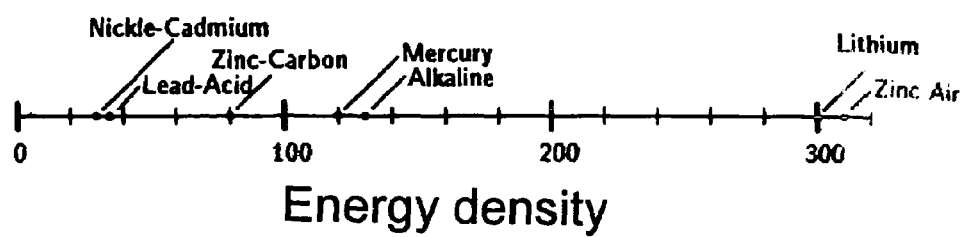
FIG. 65A shows energy density of different types of batteries.
Figure 65B:
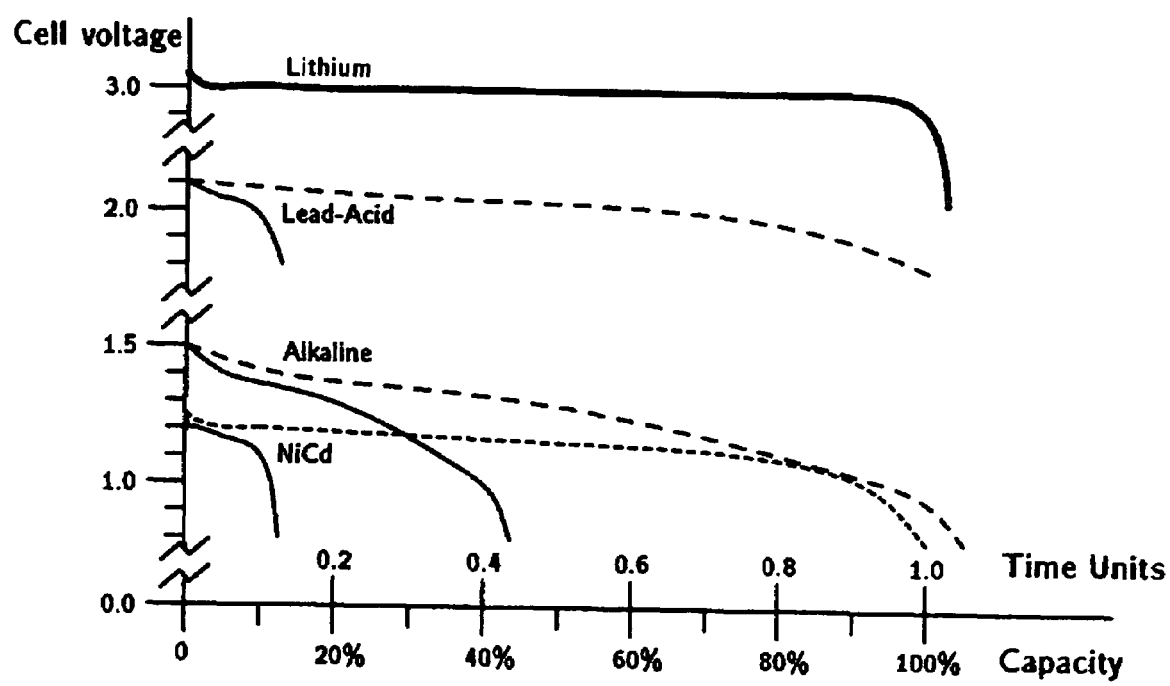
FIG. 65B shows discharge curves for different types of batteries.

In one embodiment, an implantable pulse generator with rechargeable power source can be used. Because of the rapidity of the pulses required for modulating nerve tissue 54 with stimulating and/or blocking pulses, there is a real need for power sources that will provide an acceptable service life under conditions of continuous delivery of high frequency pulses. FIG. 65A shows a graph of the energy density of several commonly used battery technologies. Lithium batteries have by far the highest energy density of commonly available batteries. Also, a lithium battery maintains a nearly constant voltage during discharge. This is shown in conjunction with FIG. 65B, which is normalized to the performance of the lithium battery. Lithium-ion batteries also have a long cycle life, and no memory effect. However, Lithium-ion batteries are not as tolerant to overcharging and over discharging. One of the most recent development in rechargable battery technology is the Lithium-ion polymer battery. Recently the major battery manufacturers (Sony, Panasonic, Sanyo) have announced plans for Lithium-ion polymer battery production.

In another embodiment, existing nerve stimulators and cardiac pacemakers can be modified to incorporate rechargeable batteries. Among the nerve stimulators that can be adopted with rechargeable batteries can for, example, be the vagus nerve stimulator manufactured by Cyberonics Inc. (Houston, Tex.). U.S. Pat. No. 4,702,254 (Zabara), U.S. Pat.

No. 5,023,807 (Zabara), and U.S. Pat. No. 4,867,164 (Zabara) on Neurocybernetic Prostheses, which can be practiced with rechargeable power source as disclosed in the next section. These patents are incorporated herein by reference.

This embodiment also comprises fixed pre-determined/pre-packaged programs. Examples of LOW, LOW-MED, MED, and HIGH stimulation states were given in the previous section, under "Programmer-less Implantable Pulse Generator (IPG)". These pre-packaged/pre-determined programs comprise unique combinations of pulse amplitude, pulse width, pulse frequency, ON-time and OFF-time.

Figure 66:
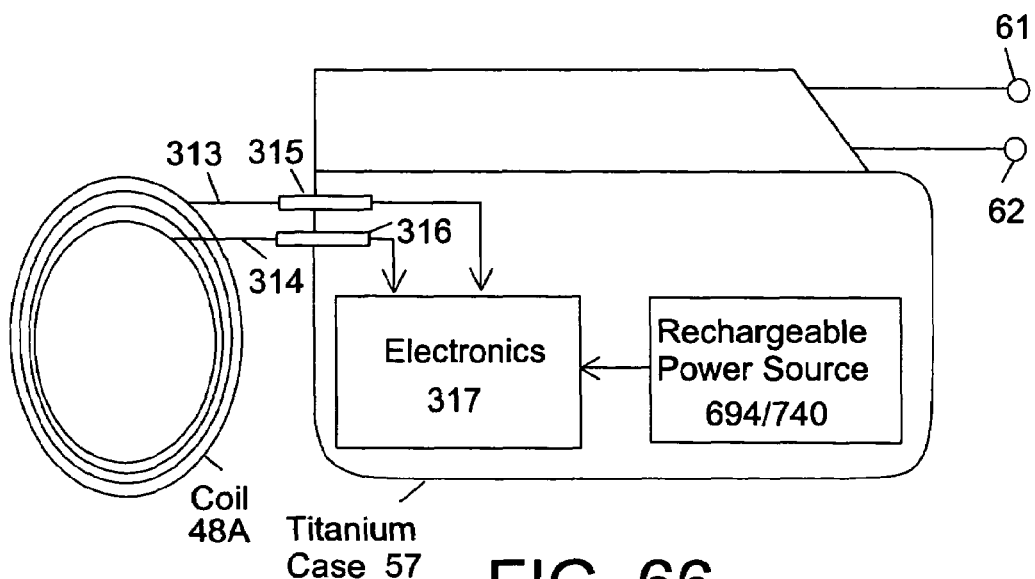
FIG. 66 depicts externalizing recharge and telemetry coil from the titanium case.

As shown in conjunction with FIG. 66, the coil is externalized from the titanium case 57. The RF pulses transmitted via coil 46 and received via subcutaneous coil 48A are rectified via a diode bridge. These DC pulses are processed and the resulting current applied to recharge the battery 694/740 in the implanted pulse generator. In one embodiment the coil 48C may be externalized at the header portion 79 of the implanted device, and may be wrapped around the titanium can, as was previously shown in FIGS. 59A-D.

Figure 67A:
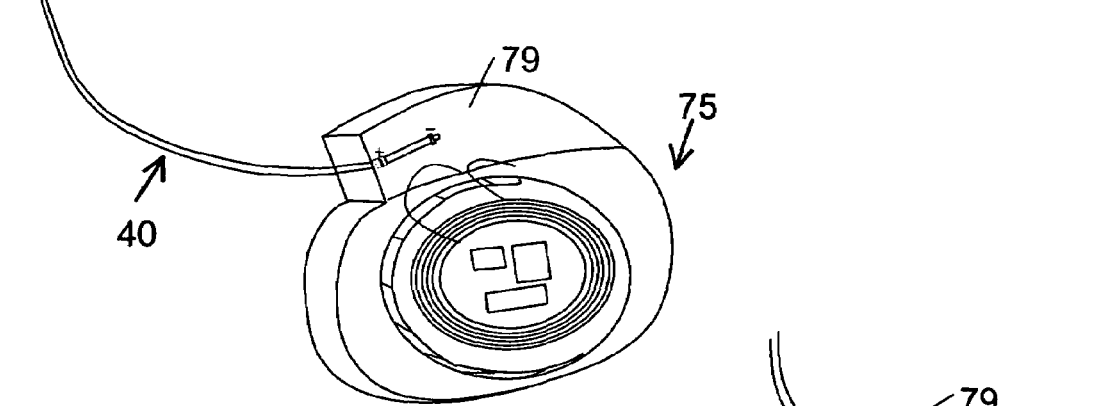
Figure 67B:
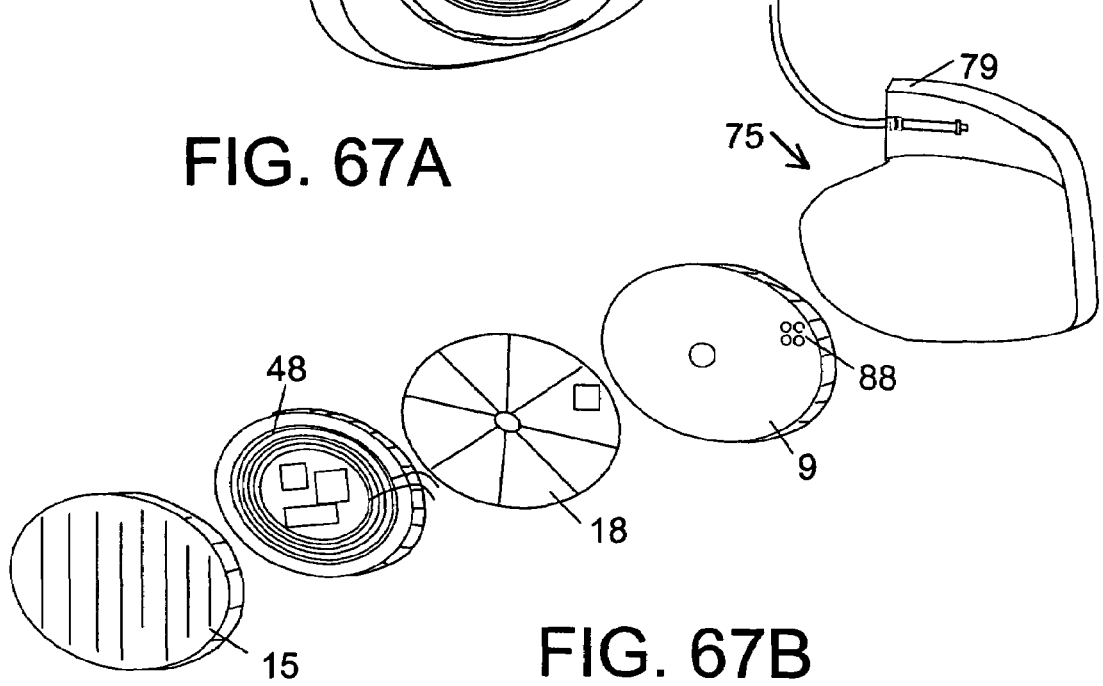

In one embodiment, the coil may also be positioned on the titanium case as shown in conjunction with FIGS. 67A and 67B. FIG. 67A shows a diagram of the finished implantable stimulator 391 R of one embodiment. FIG. 67B shows the pulse generator with some of the components used in assembly in an exploded view. These components include a coil cover 15, the secondary coil 48 and associated components, a magnetic shield 18, and a coil assembly carrier 19. The coil assembly carrier 9 has at least one positioning detail 88 located between the coil assembly and the feed through for positioning the electrical connection. The positioning detail 13 secures the electrical connection.

Figure 68:
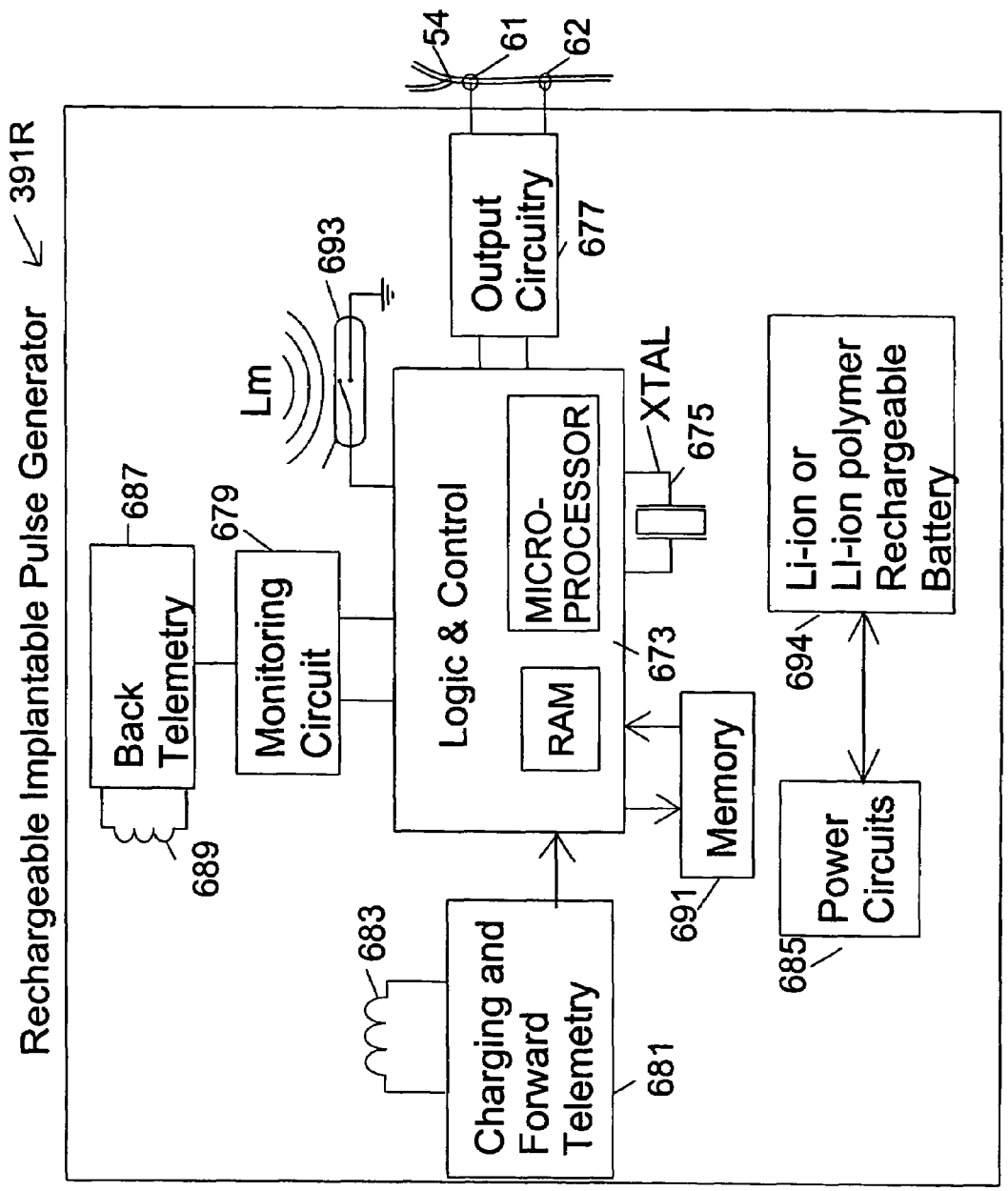
FIG. 68 shows in block diagram form an implantable rechargable pulse generator.

A schematic diagram of the implanted pulse generator (IPG 391R), with re-chargeable battery 694, is shown in conjunction with FIG. 68. The IPG 391R includes logic and control circuitry 673 connected to memory circuitry 691. The operating program and stimulation parameters are typically stored within the memory 691 via forward telemetry. Stimulation pulses are provided to the nerve tissue 54 via output circuitry 677 controlled by the microcontroller.

The operating power for the IPG 391R is derived from a rechargeable power source 694. The rechargeable power source 694 comprises a rechargeable lithium-ion or lithium-ion polymer battery. Recharging occurs inductively from an external charger to an implanted coil 48B underneath the skin 60. The rechargeable battery 694 may be recharged repeatedly as needed. Additionally, the IPG 391R is able to monitor and telemeter the status of its rechargable battery 691 each time a communication link is established with the external programmer 85.

Much of the circuitry included within the IPG 391R may be realized on a single application specific integrated circuit (ASIC). This allows the overall size of the IPG 391R to be quite small, and readily housed within a suitable hermetically-sealed case. The IPG case is preferably made from a titanium and is shaped in a rounded case.

Figure 69:
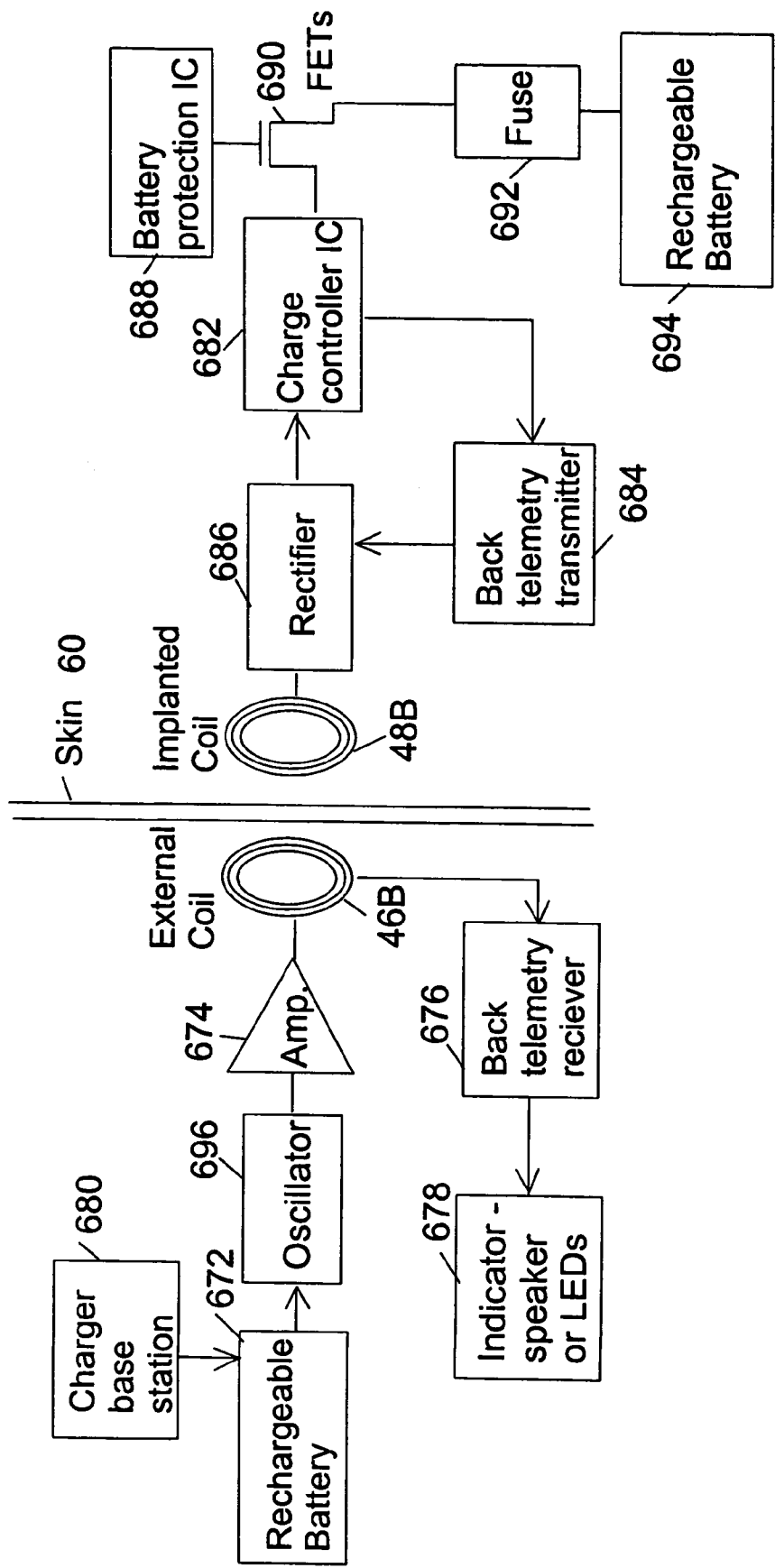
FIG. 69 depicts in block diagram form the implanted and external components of an implanted rechargable system.

Shown in conjunction with FIG. 69 are the recharging elements of this embodiment. The re-charging system uses a portable external charger to couple energy into the power source of the IPG 391R. The DC-to-AC conversion circuitry 696 of the re-charger receives energy from a battery 672 in the re-charger. A charger base station 680 and conventional AC power line may also be used. The AC signals amplified via power amplifier 674 are inductively coupled between an external coil 46B and an implanted coil 48B located subcutaneously with the implanted pulse generator (IPG) 391R.

The AC signal received via implanted coil 48B is rectified 686 to a DC signal which is used for recharging the rechargeable battery 694 of the IPG, through a charge controller IC 682. Additional circuitry within the IPG 391R includes, battery protection IC 688 which controls a FET switch 690 to make sure that the rechargeable battery 694 is charged at the proper rate, and is not overcharged. The battery protection IC 688 can be an off-the-shelf IC available from Motorola (part no. MC 33349N-3R1). This IC monitors the voltage and current of the implanted rechargeable battery 694 to ensure safe operation. If the battery voltage rises above a safe maximum voltage, the battery protection IC 688 opens charge enabling FET switches 690, and prevents further charging. A fuse 692 acts as an additional safeguard, and disconnects the battery 694 if the battery charging current exceeds a safe level. As also shown in FIG. 69, charge completion detection is achieved by a back-telemetry transmitter 684, which modulates the secondary load by changing the full-wave rectifier into a half-wave rectifier/voltage clamp. This modulation is in turn, sensed by the charger as a change in the coil voltage due to the change in the reflected impedance. When detected through a back telemetry receiver 676, either an audible alarm is generated or a LED is turned on.

Figure 70:
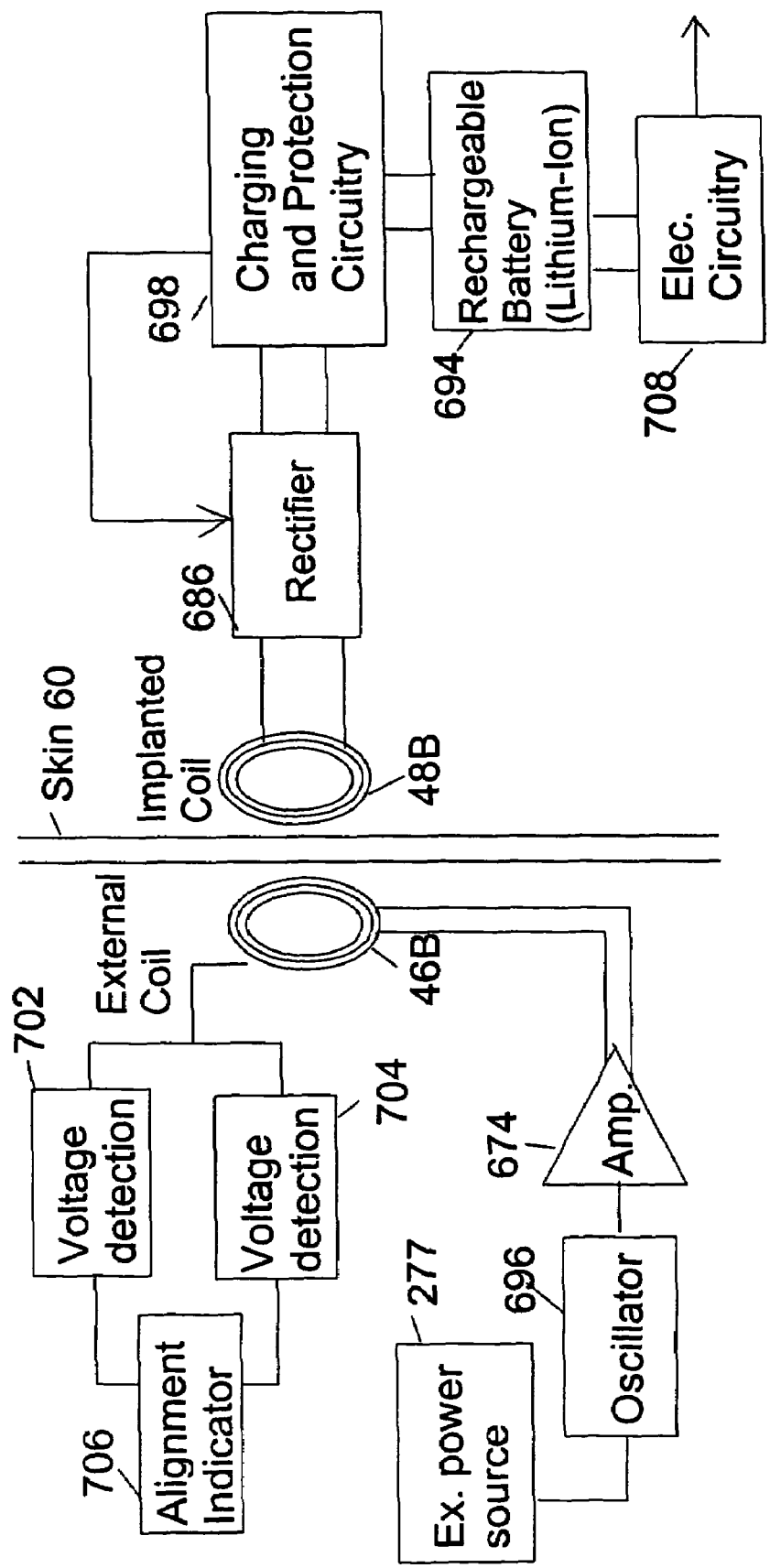
FIG. 70 depicts the alignment function of rechargable implantable pulse generator.

A simplified block diagram of charge completion and misalignment detection circuitry is shown in conjunction with FIG. 70. As shown, a switch regulator 686 operates as either a full-wave rectifier circuit or a half-wave rectifier circuit as controlled by a control signal (CS) generated by charging and protection circuitry 698. The energy induced in implanted coil 48B (from external coil 46B) passes through the switch rectifier 686 and charging and protection circuitry 698 to the implanted rechargeable battery 694. As the implanted battery 694 continues to be charged, the charging and protection circuitry 698 continuously monitors the charge current and battery voltage. When the charge current and battery voltage reach a predetermined level, the charging and protection circuitry 698 triggers a control signal. This control signal causes the switch rectifier 686 to switch to half-wave rectifier operation. When this change happens, the voltage sensed by voltage detector 702 causes the alignment indicator 706 to be activated. This indicator 706 may be an audible sound or a flashing LED type of indicator.

The indicator 706 may similarly be used as a misalignment indicator. In normal operation, when coils 46B (external) and 48B (implanted) are properly aligned, the voltage $V_s$ sensed by voltage detector 704 is at a minimum level because maximum energy transfer is taking place. If and when the coils 46B and 48B become misaligned, then less than a maximum energy transfer occurs, and the voltage $V_s$ sensed by detection circuit 704 increases significantly. If the voltage $V_s$ reaches a predetermined level, alignment indicator 706 is activated via an audible speaker and/or LEDs for visual feedback. After adjustment, when an optimum energy transfer condition is established, causing $V_s$ to decrease below the predetermined threshold level, the alignment indicator 706 is turned off.

Figure 71:
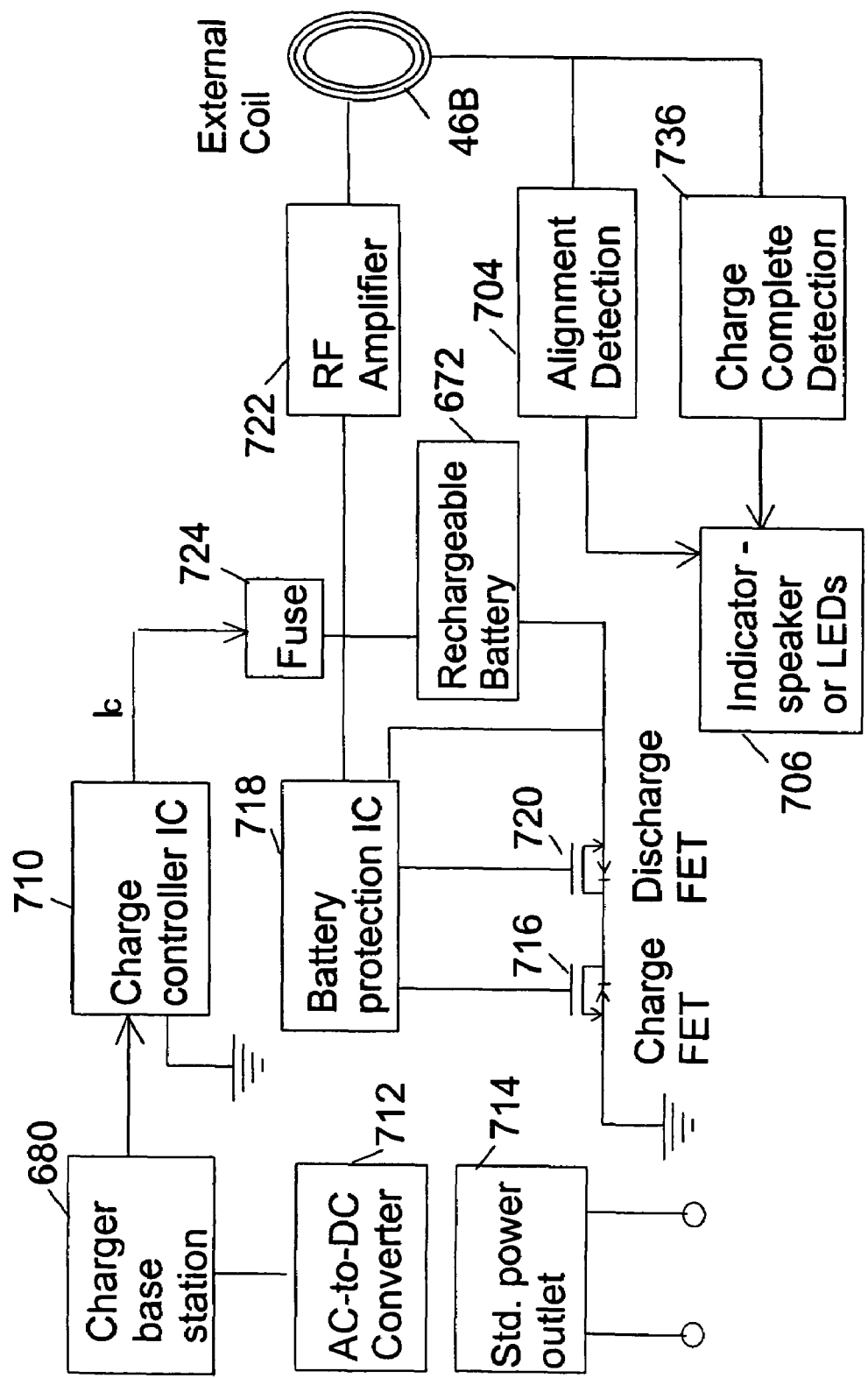
FIG. 71 is a block diagram of the external recharger.

The elements of the external recharger are shown as a block diagram in conjunction with FIG. 71. In this disclosure, the words charger and recharger are used interchangeably. The charger base station 680 receives its energy from a standard power outlet 714, which is then converted to 5 volts DC by a AC-to-DC transformer 712. When the re-charger is placed in a charger base station 680, the re-chargeable battery 672 of the re-charger is fully recharged in a few hours and is able to recharge the battery 694 of the IPG 391R. If the battery 672 of the external re-charger falls below a prescribed limit of 2.5 volt DC, the battery 672 is trickle charged until the voltage is above the prescribed limit, and then at that point resumes a normal charging process.

As also shown in FIG. 71, a battery protection circuit 718 monitors the voltage condition, and disconnects the battery 672 through one of the FET switches 716, 720 if a fault occurs until a normal condition returns. A fuse 724 will disconnect the battery 672 should the charging or discharging current exceed a prescribed amount.

In summary, in the method of the current invention for neuromodulation of cranial nerve such as the vagus nerve(s), to provide adjunct therapy for bulimia/eating disorders can be practiced with any of the several pulse generator systems disclosed including, a) an implanted stimulus-receiver with an external stimulator;

b) an implanted stimulus-receiver comprising a high value capacitor for storing charge, used in conjunction with an external stimulator;

c) a programmer-less implantable pulse generator (IPG) which is operable with a magnet;

d) a microstimulator;

e) a programmable implantable pulse generator;

f) a combination implantable device comprising both a stimulus-receiver and a programmable IPG; and g) an IPG comprising a rechargeable battery.

Neuromodulation of vagus nerve(s) with any of these systems is considered within the scope of this invention.

In one embodiment, the external stimulator and/or the programmer has a telecommunications module, as described in a co-pending application, and summarized here for reader convenience. The telecommunications module has two-way communications capabilities.

Figure 73:
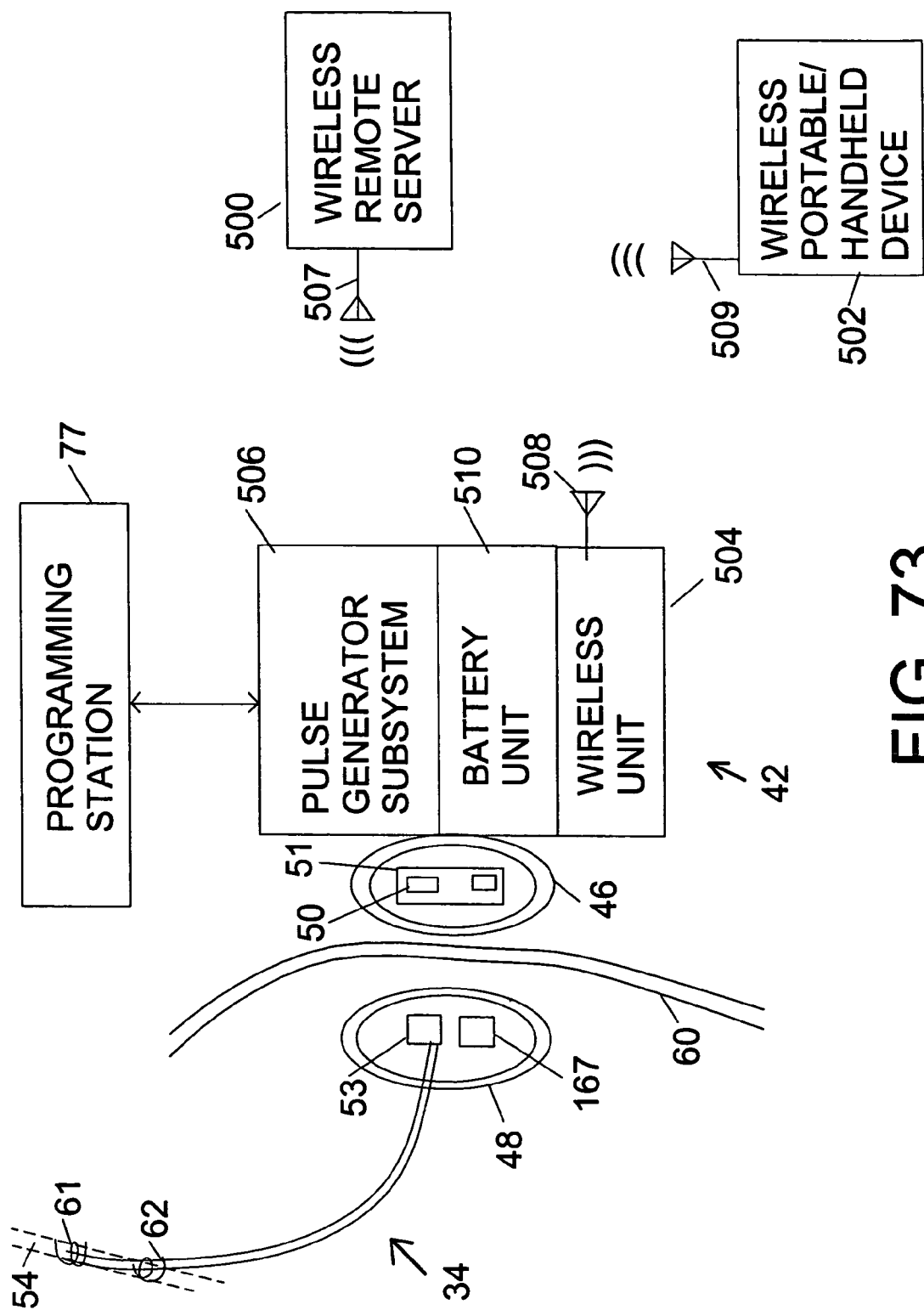
FIG. 73 is an overall schematic diagram of the external stimulator, showing wireless communication.

FIGS. 72 and 73 depict communication between an external stimulator 42 and a remote hand-held computer 502. A desktop or laptop computer can be a server 500 which is situated remotely, perhaps at a physician's office or a hospital. The stimulation parameter data can be viewed at this facility or reviewed remotely by medical personnel on a hand-held personal data assistant (PDA) 502, such as a "palm-pilot" from PALM corp. (Santa Clara, Calif.), a "Visor" from Handspring Corp. (Mountain view, Calif.) or on a personal computer (PC). The physician or appropriate medical personnel, is able to interrogate the external stimulator 42 device and know what the device is currently programmed to, as well as, get a graphical display of the pulse train. The wireless communication with the remote server 500 and hand-held PDA 502 would be supported in all geographical locations within and outside the. United States (US) that provides cell phone voice and data communication service.

In one aspect of the invention, the telecommunications component can use Wireless Application Protocol (WAP). The Wireless Application Protocol (WAP), which is a set of communication protocols standardizing Internet access for wireless devices. While previously, manufacturers used different technologies to get Internet on hand-held devices, with WAP devices and services interoperate. WAP also promotes convergence of wireless data and the Internet. The WAP programming model is heavily based on the existing Internet programming model, and is shown schematically in FIG. 74. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops.

Figure 74:
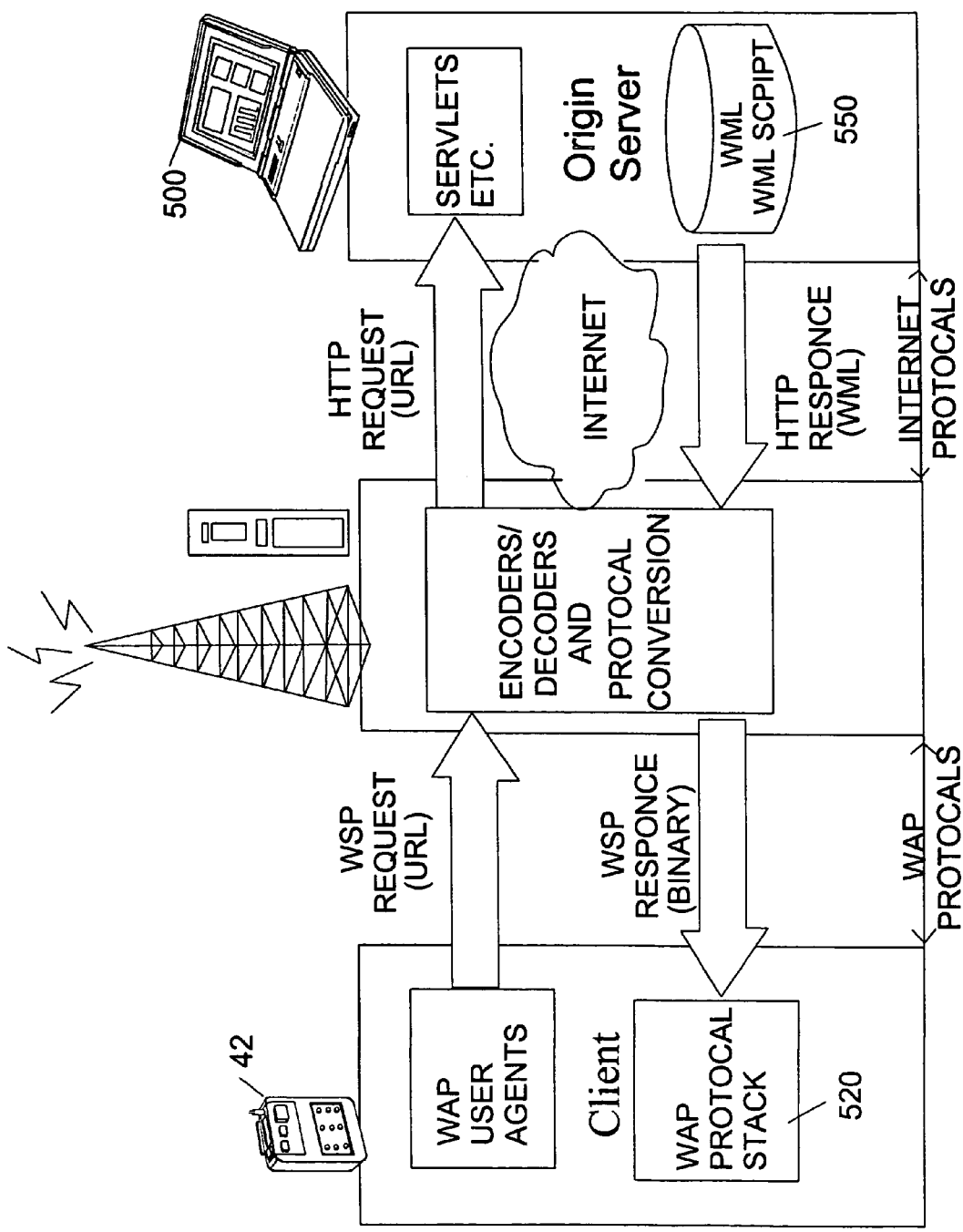
FIG. 74 is a schematic diagram showing application of Wireless Application Protocol (WAP).

The key components of the WAP technology, as shown in FIG. 74, includes 1) Wireless Mark-up Language (WML) 550 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/WMLScript content. 4) A lightweight protocol stack 520 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support-header caching, thereby economizing on bandwidth requirements. WSP also compensates for high latency by allowing requests and responses to be handled asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications and greater details have been publicized, and well known to those skilled in the art.

In this embodiment, two modes of communication are possible. In the first, the server initiates an upload of the actual parameters being applied to the patient, receives these from the stimulator, and stores these in its memory, accessible to the authorized user as a dedicated content driven web page. The physician or authorized user can make alterations to the actual parameters, as available on the server, and then initiate a communication session with the stimulator device to download these parameters.

Figure 75:
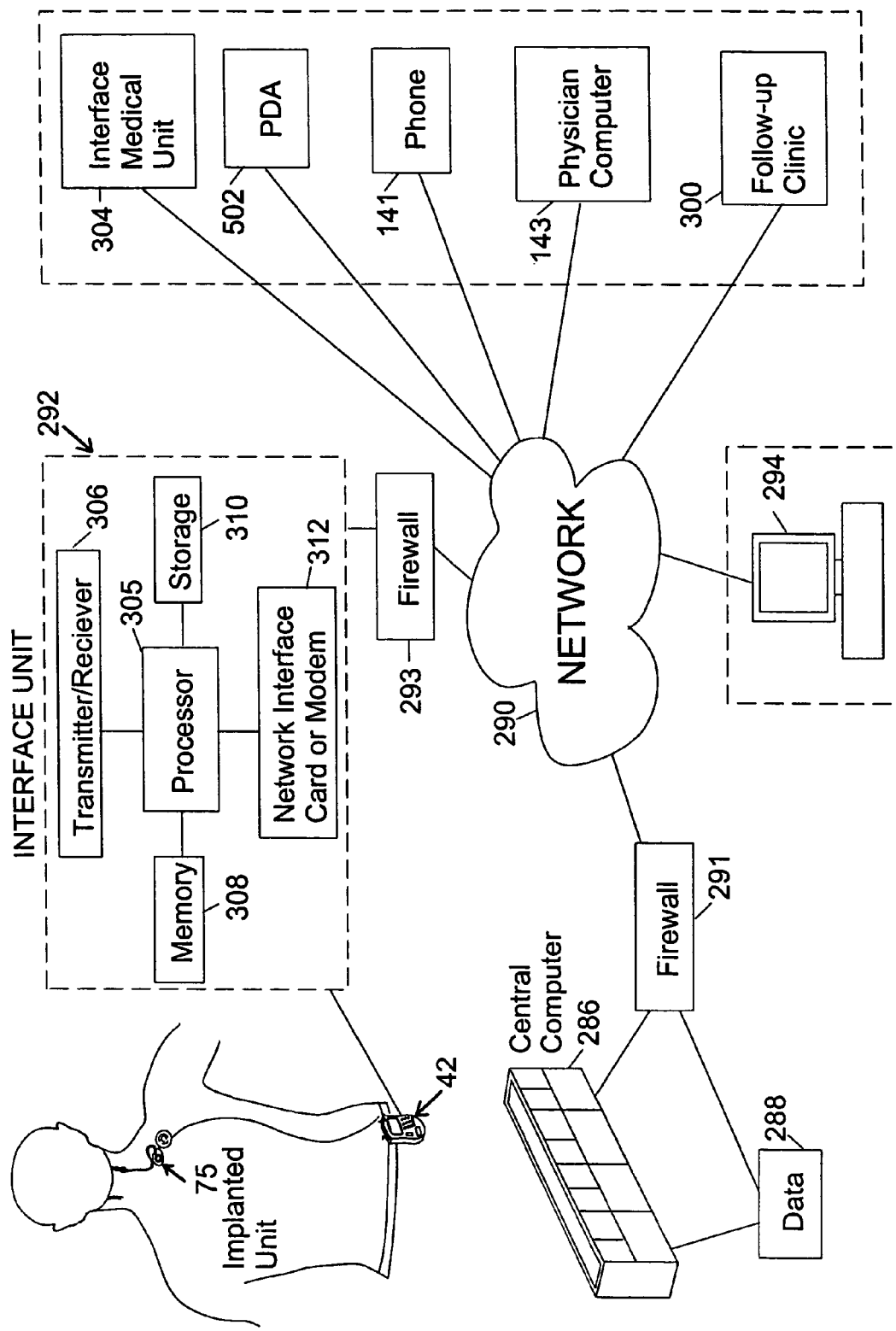
FIG. 75 is a simplified block diagram of the networking interface board.

Shown in conjunction with FIG. 75, in one embodiment, the external stimulator 42 and/or the programmer 85 may also be networked to a central collaboration computer 286 as well as other devices such as a remote computer 294, PDA 502, phone 141, physician computer 143. The interface unit 292 in this embodiment communicates with the central collaborative network 290 via land-lines such as cable modem or wirelessly via the internet. A central computer 286 which has sufficient computing power and storage capability to collect and process large amounts of data, contains information regarding device history and serial number, and is in communication with the network 290. Communication over collaboration network 290 may be effected by way of a TCP/IP connection, particularly one using the internet, as well as a PSTN, DSL, cable modem, LAN, WAN or a direct dial-up connection.

The standard components of interface unit shown in block 292 are processor 305, storage 310, memory 308, transmitter/receiver 306, and a communication device such as network interface card or modem 312. In the preferred embodiment these components are embedded in the external stimulator 42 and can also be embedded in the programmer 85. These can be connected to the network 290 through appropriate security measures (Firewall) 293.

Another type of remote unit that may be accessed via central collaborative network 290 is remote computer 294.

This remote computer 294 may be used by an appropriate attending physician to instruct or interact with interface unit 292, for example, instructing interface unit 292 to send instruction downloaded from central computer 286 to remote implanted unit.

Figure 76A:
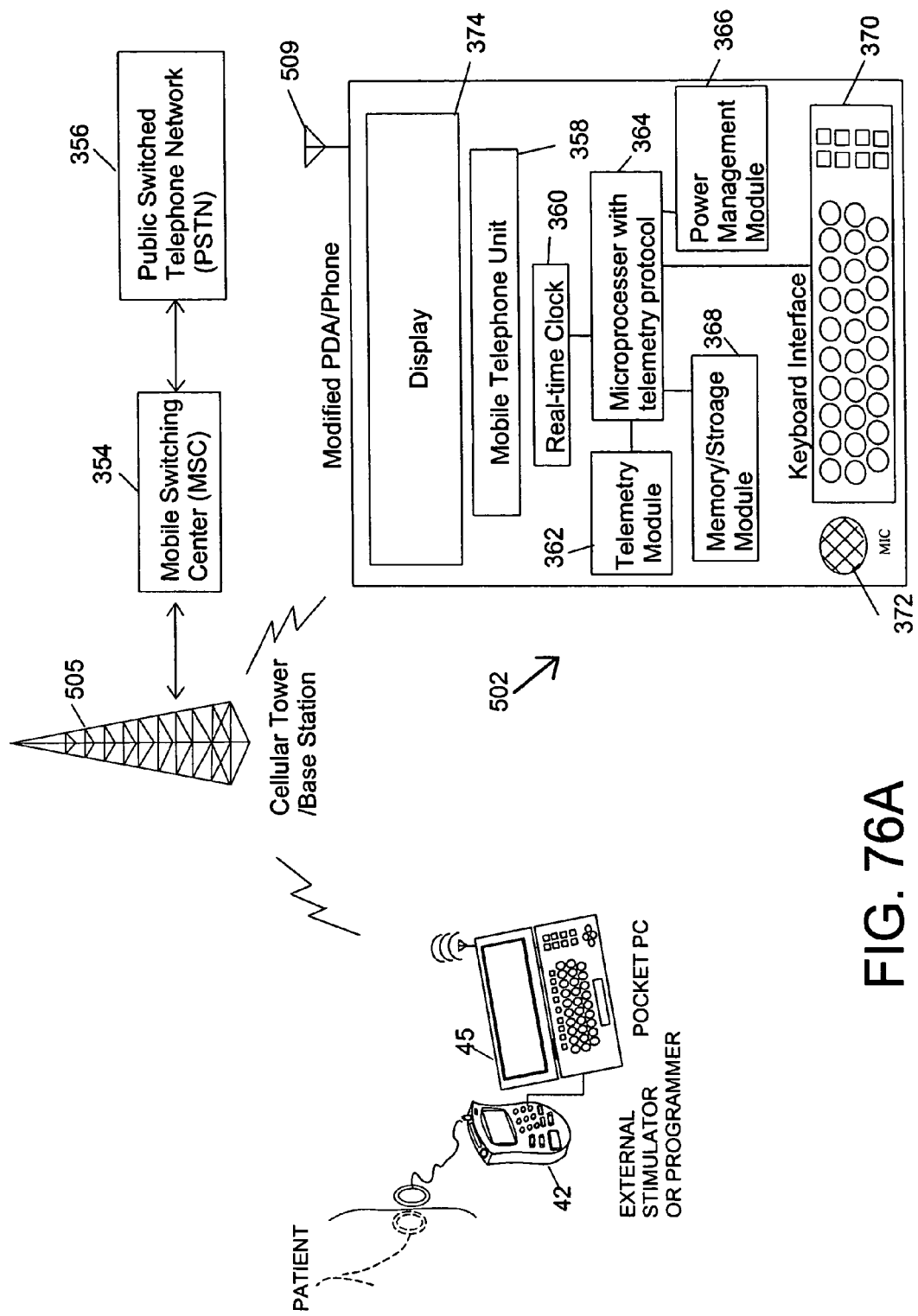
FIGS. 76A and 76B is a simplified diagram showing communication of modified PDA/phone with an external stimulator via a cellular tower/base station.
Figure 76B:
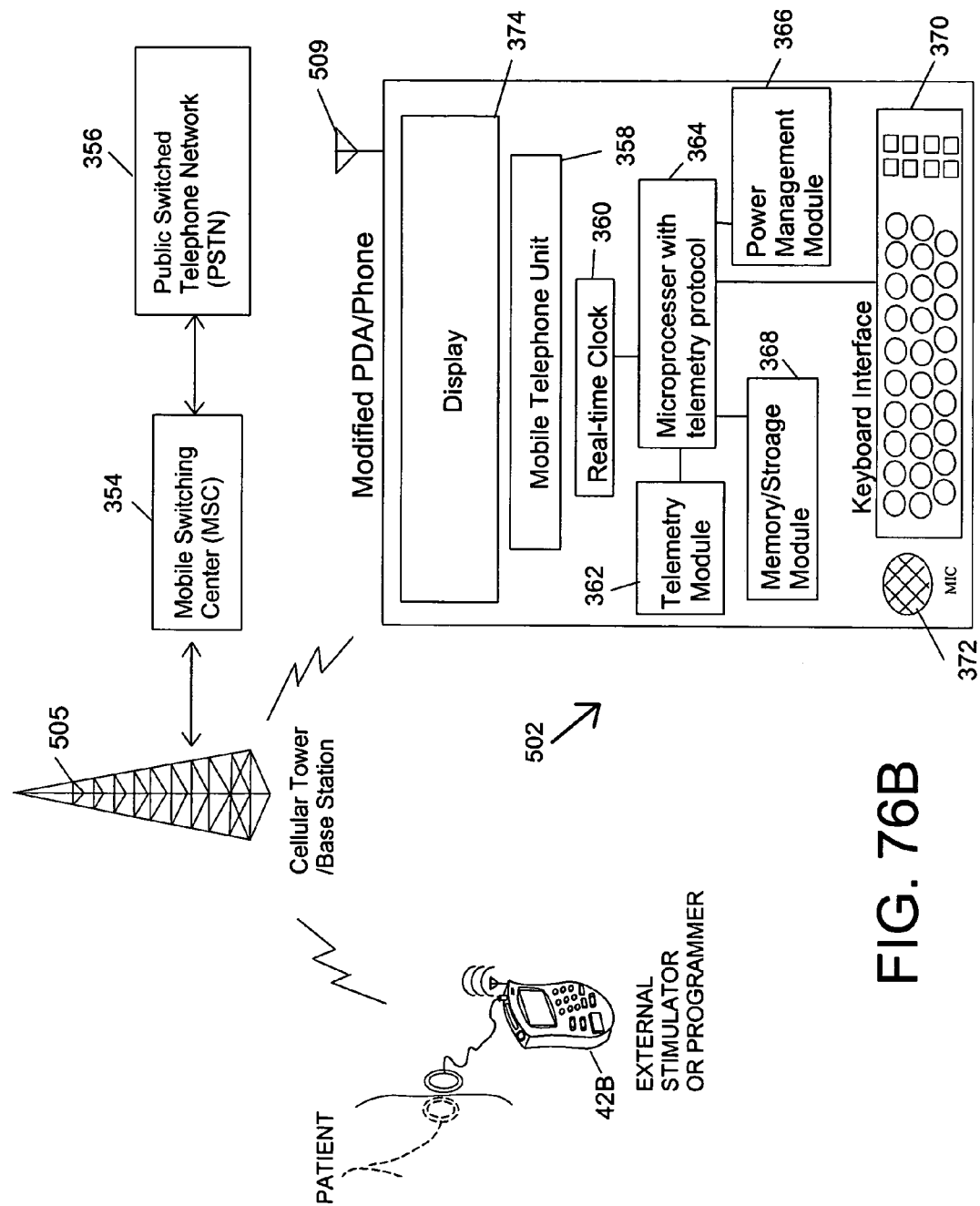

Shown in conjunction with FIGS. 76A and 76B the physician's remote communication's module is a Modified PDA/Phone 502 in this embodiment. The Modified PDA/Phone 502 is a microprocessor based device as shown in a simplified block diagram in FIGS. 76A and 76B. The PDA/Phone 502 is configured to accept PCM/CIA cards specially configured to fulfill the role of communication module 292 of the present invention. The Modified PDA/Phone 502 may operate under any of the useful software including Microsoft Window's based, Linux, Palm OS, Java OS, SYMBIAN, or the like.

The telemetry module 362 comprises an RF telemetry antenna 142 coupled to a telemetry transceiver and antenna driver circuit board which includes a telemetry transmitter and telemetry receiver. The telemetry transmitter and receiver are coupled to control circuitry and registers, operated under the control of microprocessor 364. Similarly, within stimulator a telemetry antenna 142 is coupled to a telemetry transceiver comprising RF telemetry transmitter and receiver circuit. This circuit is coupled to control circuitry and registers operated under the control of microcomputer circuit.

With reference to the telecommunications aspects of the invention, the communication and data exchange between Modified PDA/Phone 502 and external stimulator 42 operates on commercially available frequency bands. The 2.4-to-2.4853 GHz bands or 5.15 and 5.825 GHz, are the two unlicensed areas of the spectrum, and set aside for industrial, scientific, and medical (ISM) uses. Most of the technology today including this invention, use either the 2.4 or 5 GHz radio bands and spread-spectrum technology.

The telecommunications technology, especially the wireless internet technology, which this invention utilizes in one embodiment, is constantly improving and evolving at a rapid pace, due to advances in RF and chip technology as well as software development. Therefore, one of the intents of this invention is to utilize "state of the art" technology available for data communication between Modified PDA/Phone 502 and external stimulator 42. The intent of this invention is to use 3G technology for wireless communication and data exchange, even though in some cases 2.5G is being used currently.

For the system of the current invention, the use of any of the "3G" technologies for communication for the Modified PDA/Phone 502, is considered within the scope of the invention. Further, it will be evident to one of ordinary skill in the art that as future 4G systems, which will include new technologies such as improved modulation and smart antennas, can be easily incorporated into the system and method of current invention, and are also considered within the scope of the invention.

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

We claim:

1. A method of treating or alleviating the symptoms of eating disorders by stimulating and/or blocking the vagus nerve(s) or branches thereof with pre-determined electric pulses, comprising the steps of:

a) selecting a patient with an eating disorder;

b) providing an external stimulus generator with a wireless communication system that is operable to provide pulse stimulation programming as well as power to an implanted stimulator;

c) implanting an implantable stimulator in said patient and electrically connecting at least one implantable stimulator electrode to a vagus nerve or branch thereof, said implantable stimulator comprising a pulse generator module and a stimulus receiver module, said pulse generator module including a microprocessor and pre-programmed instructions for controlling electrical output to the implantable stimulator electrode, said stimulus receiver module including a coil that receives both said pulse stimulation programming and said power from said external stimulus generator whereby said pulse stimulation programming is supplied to said pulse generator module and power is supplied to said implantable stimulator; a battery connected by a switch to the implantable stimulator for supplying power thereto, a sensor to detect the presence of external power from said external stimulus generator so as to cause said switch to switch from connection to said battery to connection to said stimulus receiver module power supply while adequate external power is sensed and maintained;

d) selectively applying pulses to the patient to treat said eating disorder using said implantable stimulator generator alone or operated by said external pulse generator signal.

2. The method of claim 1, wherein said nerve blocking comprises at least one from a group consisting of: DC or anodal block, Wedenski block, and Collision block.

3. The method of claim 1, wherein said stimulating and/or blocking pre-determined electric pulses are provided for a therapy that has cumulative effect.

4. The method of claim 1, wherein said treating or alleviating the symptoms of eating disorders is based on selective stimulation of left vagus nerve, without the effect of EEG desynchronization.

5. The method of claim 1, wherein said stimulation and/or blocking is an open loop method.

6. The method of claim 1, wherein said stimulus-receiver comprises a high value capacitor for storing electric charge.

7. The method of claim 1, wherein said implantable stimulator further comprises a microstimulator.

8. The method of claim 1, wherein said implantable stimulator battery is a rechargeable battery.

9. The method of claim 1, wherein said pre-determined electric pulses can be provided anywhere along the length of said vagus nerve(s) or its branches, at one or multiple sites.

10. The method of claim 1, wherein said implantable stimulator further comprises at least two predetermined pre-packaged programs stored in a memory, wherein said predetermined/pre-packaged programs define parameters or pulse amplitude, pulse width, pulse frequency, on-time and off-time sequences.

11. The method of claim 1, wherein said pre-determined electrical pulses can be modified.

12. The method of claim 1, wherein said implantable stimulator further comprises a telemetry means for remote device interrogation and programming, over a wide area network.

13. The method of claim 1, wherein said at least one implantable stimulator electrode is from a group consisting of spiral electrodes, cuff electrodes, steroid eluting electrodes, wrap-around electrodes, and hydrogel electrodes.

14. The method of claim 1, wherein said pre-determined electric pulses further comprise pulse amplitudes between 0.1 volt-15 volts; pulse widths between 20 micro-seconds-5 milli-seconds; stimulation frequencies between 5 Hz and 200 Hz, and blocking frequencies between 0 and 750 Hz.

* * * * *